US012633400B2

(12) United States Patent
Zahora et al.

(10) Patent No.: US 12,633,400 B2
(45) Date of Patent: May 19, 2026

(54) SYSTEMS AND METHODS FOR MEDICAL CLAIMS ANALYTICS AND PROCESSING SUPPORT

(71) Applicant: ZOLL Medical Corporation, Chelmsford, MA (US)

(72) Inventors: Kevin M. Zahora, Liberty Township, OH (US); Tyler L. Williams, Sarasota, FL (US); Charles E. Fuller, III, Westminster, CO (US); Frederick Forester, San Diego, CA (US); Jessica P. Deschane, Thornton, CO (US); Paul D. Canino, Miller Place, NY (US); Mario Sanchez, Jr., Longmont, CO (US); Kristin N. Whitt, Dayton, OH (US)

(73) Assignee: ZOLL Medical Corporation, Chelmsford, MA (US)

( * ) Notice: Subject to any disclaimer, the term of this patent is extended or adjusted under 35 U.S.C. 154(b) by 98 days.

(21) Appl. No.: 18/128,581

(22) Filed: Mar. 30, 2023

(65) Prior Publication Data

US 2023/0317260 A1 Oct. 5, 2023

Related U.S. Application Data

(60) Provisional application No. 63/325,729, filed on Mar. 31, 2022.

(51) Int. Cl.
*G16H 40/20* (2018.01)
*G16H 50/70* (2018.01)

(52) U.S. Cl.
CPC ............. *G16H 40/20* (2018.01); *G16H 50/70* (2018.01)

(58) Field of Classification Search
CPC .......... G16H 50/20; G06N 20/00; G06N 7/01; G06Q 10/10; G06Q 40/08
(Continued)

(56) References Cited

U.S. PATENT DOCUMENTS

| | | | |
|---|---|---|---|
| 7,734,481 | B1 | 6/2010 | Hutton et al. |
| 7,739,132 | B2 | 6/2010 | Denny, Jr. et al. |

(Continued)

FOREIGN PATENT DOCUMENTS

| | | |
|---|---|---|
| CA | 2792070 | 4/2013 |
| CA | 3126644 | 4/2013 |

(Continued)

OTHER PUBLICATIONS

Nyce, Charles, Predictive Analytics White Paper, American Institute for CPCU/Insurance Institute of America, Oct. 2007.
(Continued)

*Primary Examiner* — Dilek B Cobanoglu
(74) *Attorney, Agent, or Firm* — Mintz, Levin, Cohn, Ferris, Glovsky and Popeo, P.C.

(57) ABSTRACT

In an illustrative embodiment, a system for providing automation and virtual assistance to medical claims processing includes a predictive analytics platform configured to receive patient information for a medical claim from a claims processing system, cross-reference the patient information with stored data to identify a patient record, apply the patient information to machine learning classifier(s) to estimate a likelihood of match between the patient information and the patient record, provide patient record information to the claims system, receive claims data from the claims system, access, from a data universe, requirements corresponding to a payer corresponding to the medical claim, the requirements having been generated through training machine learning classifier(s) with claims data correspond-
(Continued)

ing to claims denied by the payer, verify the claims data in view of the requirements, and provide an indication of missing claims information and/or invalid claims information to the claims system.

24 Claims, 27 Drawing Sheets

(58) Field of Classification Search
USPC ......................................................... 705/2, 3
See application file for complete search history.

(56) References Cited

U.S. PATENT DOCUMENTS

| | | | |
|---|---|---|---|
| 7,778,850 B2 | 8/2010 | Wester | |
| 7,797,165 B1 | 9/2010 | Beery et al. | |
| 7,873,528 B2 | 1/2011 | Bregante et al. | |
| 8,204,762 B2 | 6/2012 | Wester | |
| 8,229,770 B2 | 7/2012 | Bregante et al. | |
| 8,306,829 B2 | 11/2012 | Starkey et al. | |
| 8,326,656 B2 | 12/2012 | Beery et al. | |
| 8,407,066 B2 | 3/2013 | Gentry et al. | |
| 8,433,586 B2 | 4/2013 | Wester | |
| 8,566,117 B1 | 10/2013 | Troutt et al. | |
| 8,600,885 B2 | 12/2013 | Hoffman | |
| 8,645,162 B2 | 2/2014 | Boerger et al. | |
| 8,655,685 B2 | 2/2014 | Denny, Jr. et al. | |
| 8,719,057 B2 | 5/2014 | Denny, Jr. et al. | |
| 8,781,850 B2 | 7/2014 | Bazzani et al. | |
| 8,898,798 B2 | 11/2014 | Rogers et al. | |
| 8,943,565 B2 | 1/2015 | Magee et al. | |
| 9,324,111 B2 | 4/2016 | Long et al. | |
| 10,102,340 B2 | 10/2018 | Tanner, Jr. et al. | |
| 10,121,557 B2 | 11/2018 | Aldridge et al. | |
| 10,217,141 B2 | 2/2019 | Hoffman | |
| 10,354,211 B1 | 7/2019 | Pilkington et al. | |
| 10,380,320 B2 | 8/2019 | Farmer et al. | |
| 10,387,615 B2 | 8/2019 | Derer | |
| 10,410,305 B1 | 9/2019 | Pilkington et al. | |
| 10,430,428 B2 | 10/2019 | Ott et al. | |
| 10,510,046 B2 | 12/2019 | Whittier et al. | |
| 10,510,440 B1 | 12/2019 | Jose | |
| 10,598,508 B2 | 3/2020 | Gotschall et al. | |
| 10,719,581 B2 | 7/2020 | Lacy et al. | |
| 10,747,792 B2 | 8/2020 | Ouyang | |
| 10,810,218 B2 | 10/2020 | Ng et al. | |
| 10,942,040 B2 | 3/2021 | Gotschall et al. | |
| 10,970,785 B2 | 4/2021 | Gotschall et al. | |
| 10,991,457 B1 | 4/2021 | Hallemeier et al. | |
| 11,011,256 B2 | 5/2021 | Dunleavy | |
| 11,114,185 B1 | 9/2021 | Malec et al. | |
| 11,328,825 B1 | 5/2022 | Yu et al. | |
| 11,334,822 B2 | 5/2022 | Long et al. | |
| 11,347,829 B1 * | 5/2022 | Sclar | G06Q 40/08 |
| 11,410,246 B2 | 8/2022 | Bull | |
| 11,538,112 B1 * | 12/2022 | Singh | G06Q 10/10 |
| 11,574,364 B2 | 2/2023 | D'Abbene et al. | |
| 11,763,390 B2 | 9/2023 | Poteet et al. | |
| 11,783,922 B1 | 10/2023 | Tong et al. | |
| 2003/0036926 A1 | 2/2003 | Starkey et al. | |
| 2004/0133452 A1 | 7/2004 | Denny, Jr. et al. | |
| 2006/0184397 A1 | 8/2006 | Wester | |
| 2007/0011030 A1 | 1/2007 | Bregante et al. | |
| 2007/0011031 A1 | 1/2007 | Bregante et al. | |
| 2007/0011032 A1 | 1/2007 | Bregante et al. | |
| 2007/0271119 A1 | 11/2007 | Boerger et al. | |
| 2008/0275737 A1 | 11/2008 | Gentry et al. | |
| 2011/0004494 A1 | 1/2011 | Denny, Jr. et al. | |
| 2011/0066447 A1 | 3/2011 | Beery et al. | |
| 2011/0112859 A1 | 5/2011 | Bregante et al. | |
| 2011/0145021 A1 | 6/2011 | Denny, Jr. et al. | |
| 2011/0238451 A1 | 9/2011 | Bazzani et al. | |
| 2011/0301979 A1 | 12/2011 | Wester | |
| 2012/0253850 A1 | 10/2012 | Wester | |
| 2012/0259773 A1 | 10/2012 | Hoffman | |
| 2012/0284044 A1 | 11/2012 | Bregante et al. | |
| 2013/0054259 A1 | 2/2013 | Wojtusiak et al. | |
| 2013/0096952 A1 | 4/2013 | Beery et al. | |
| 2013/0097157 A1 | 4/2013 | Ng et al. | |
| 2013/0191895 A1 | 7/2013 | Magee et al. | |
| 2013/0218587 A1 | 8/2013 | Carter, Jr. et al. | |
| 2013/0238362 A1 | 9/2013 | Wester | |
| 2013/0246090 A1 | 9/2013 | Hoffman et al. | |
| 2013/0262148 A1 | 10/2013 | Weber et al. | |
| 2013/0262149 A1 | 10/2013 | Weber et al. | |
| 2013/0262150 A1 | 10/2013 | Weber et al. | |
| 2014/0046678 A1 | 2/2014 | Lacy et al. | |
| 2014/0089181 A1 | 3/2014 | Hoffman | |
| 2014/0095188 A1 | 4/2014 | Derer | |
| 2014/0149135 A1 | 5/2014 | Boerger et al. | |
| 2014/0200928 A1 | 7/2014 | Watanabe et al. | |
| 2014/0278511 A1 | 9/2014 | Fielding et al. | |
| 2014/0278525 A1 | 9/2014 | Curran | |
| 2014/0324485 A1 | 10/2014 | Bazzani et al. | |
| 2014/0379363 A1 | 12/2014 | Hart et al. | |
| 2015/0088535 A1 | 3/2015 | Smith et al. | |
| 2015/0100349 A1 | 4/2015 | Acy et al. | |
| 2015/0127364 A1 | 5/2015 | Long et al. | |
| 2015/0205846 A1 | 7/2015 | Aldridge et al. | |
| 2015/0302089 A1 | 10/2015 | Magee et al. | |
| 2015/0302528 A1 | 10/2015 | Piskiel | |
| 2016/0162993 A1 | 6/2016 | Weber et al. | |
| 2016/0162994 A1 | 6/2016 | Weber et al. | |
| 2016/0267230 A1 | 9/2016 | Ochs et al. | |
| 2016/0342750 A1 | 11/2016 | Alstad et al. | |
| 2016/0342751 A1 | 11/2016 | Alstad et al. | |
| 2017/0308652 A1 | 10/2017 | Ligon | |
| 2017/0351821 A1 | 12/2017 | Tanner, Jr. et al. | |
| 2018/0197160 A1 | 7/2018 | Hoffman et al. | |
| 2019/0074072 A1 | 3/2019 | Aldridge et al. | |
| 2019/0080416 A1 * | 3/2019 | Smith | G06N 20/00 |
| 2019/0304582 A1 | 10/2019 | Blumenthal et al. | |
| 2020/0089173 A1 * | 3/2020 | Hazard | G06N 7/01 |
| 2020/0273570 A1 | 8/2020 | Subramanian et al. | |
| 2020/0311823 A1 | 10/2020 | D'Abbene et al. | |
| 2021/0034613 A1 | 2/2021 | Ng et al. | |
| 2021/0295448 A1 | 9/2021 | McClain et al. | |
| 2021/0304265 A1 | 9/2021 | Yedlarajaiah et al. | |
| 2022/0051276 A1 | 2/2022 | Zelocchi | |
| 2022/0309592 A1 | 9/2022 | Zahora et al. | |
| 2022/0319678 A1 | 10/2022 | Harada et al. | |
| 2022/0319717 A1 * | 10/2022 | Henderson, Jr. | G16H 50/20 |
| 2023/0005616 A1 | 1/2023 | Zhang et al. | |
| 2023/0054258 A1 | 2/2023 | Peresie et al. | |
| 2023/0063220 A1 | 3/2023 | Hulvey et al. | |
| 2023/0069182 A1 | 3/2023 | Peresie et al. | |
| 2023/0316408 A1 | 10/2023 | Khan et al. | |

FOREIGN PATENT DOCUMENTS

| | | | | |
|---|---|---|---|---|
| CA | 2845532 | | 9/2014 | |
| CA | 2925118 | | 2/2015 | |
| CA | 2937454 | | 7/2015 | |
| CN | 105793886 | | 7/2016 | |
| CN | 106462859 | | 2/2017 | |
| CN | 108352035 | | 7/2018 | |
| DE | 102022128345 | A1 * | 5/2023 | G06N 3/042 |
| EP | 3050022 | | 8/2016 | |
| EP | 3097527 | | 11/2016 | |
| EP | 3298554 | | 3/2018 | |
| JP | 2016538610 | | 12/2016 | |
| JP | 2017509954 | | 4/2017 | |
| JP | 2018526704 | | 9/2018 | |
| MX | 2012011903 | | 8/2013 | |
| MX | 338656 | | 4/2016 | |
| WO | 2007002611 | | 1/2007 | |
| WO | 2011120003 | | 9/2011 | |
| WO | 2015047561 | | 4/2015 | |
| WO | 2015112202 | | 7/2015 | |
| WO | 2017082959 | | 5/2017 | |

(56)         References Cited

FOREIGN PATENT DOCUMENTS

WO      2017214181      12/2017
WO      2022006441       1/2022

OTHER PUBLICATIONS

Accounts Receivable (AR) Solution | ZOLL AR Boost, Uncover More Revenue and Shrink AR by Knowing Your Patients Financially, Web Capture Date Mar. 30, 2023. <www.zolldata.com/arboost>.

ZOLL AR Boost: Accounts Receivable Management, Web Capture Date Mar. 30, 2023. <www.zolldata.com/accounts-receivable-management>.

A Guide to Robotic Process Automation for Medical Billing, Publication Date Aug. 8, 2019, Web Capture Date Mar. 30, 2023. <https://www.imagineteam.com/blog/guide-to-robotic-process-automation-medical-billing>.

Kenneth et al. (2019) "Beyond One-Off Integrations: A Commercial, Substitutable, Reusable, Standards-Based, Electronic Health Record-Connected App", Journal of Medical Internet Research, 21(2):7 pages.

* cited by examiner

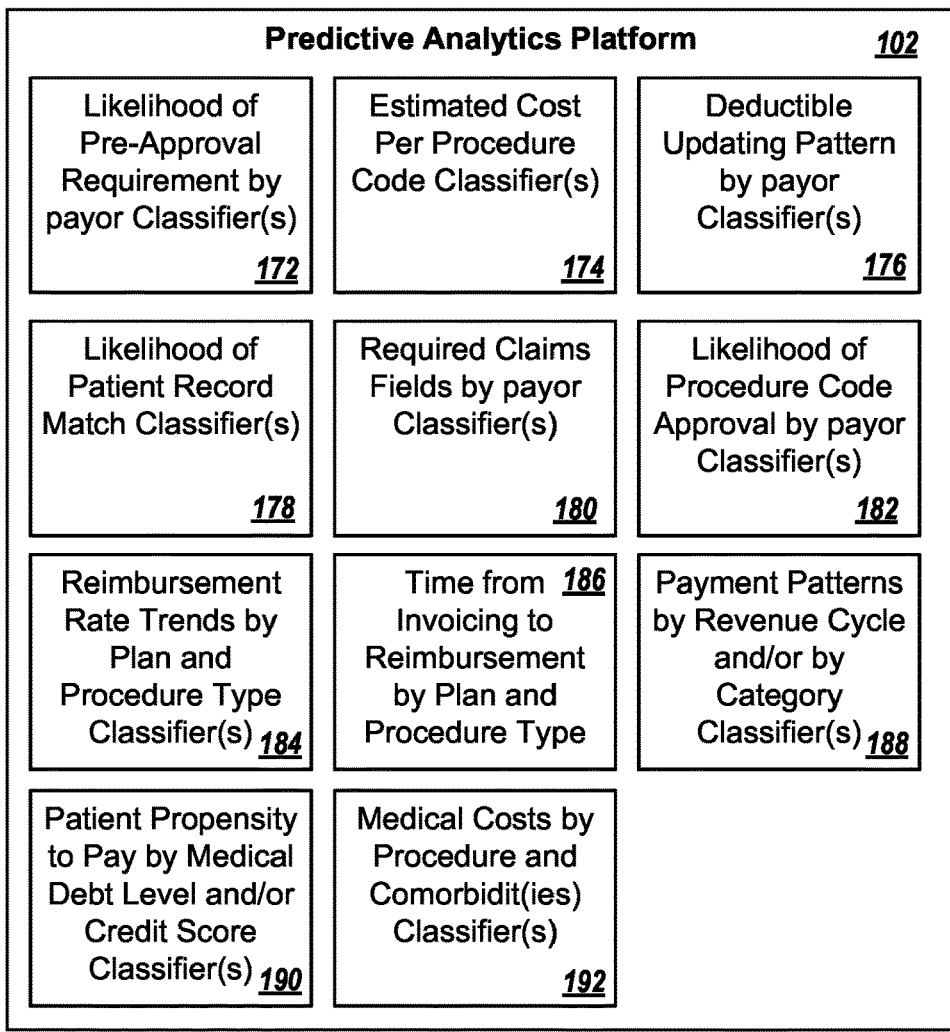

Predictive Analytics Platform _102_

| | | |
|---|---|---|
| Likelihood of Pre-Approval Requirement by payor Classifier(s) _172_ | Estimated Cost Per Procedure Code Classifier(s) _174_ | Deductible Updating Pattern by payor Classifier(s) _176_ |
| Likelihood of Patient Record Match Classifier(s) _178_ | Required Claims Fields by payor Classifier(s) _180_ | Likelihood of Procedure Code Approval by payor Classifier(s) _182_ |
| Reimbursement Rate Trends by Plan and Procedure Type Classifier(s) _184_ | Time from _186_ Invoicing to Reimbursement by Plan and Procedure Type | Payment Patterns by Revenue Cycle and/or by Category Classifier(s) _188_ |
| Patient Propensity to Pay by Medical Debt Level and/or Credit Score Classifier(s) _190_ | Medical Costs by Procedure and Comorbidit(ies) Classifier(s) _192_ | |

_160_

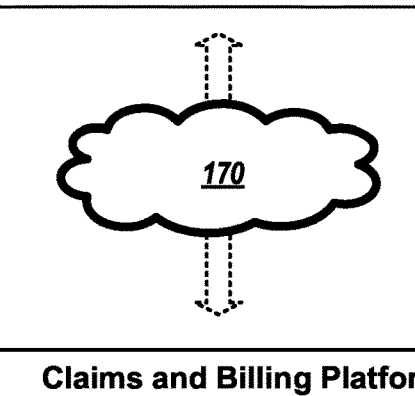

_170_

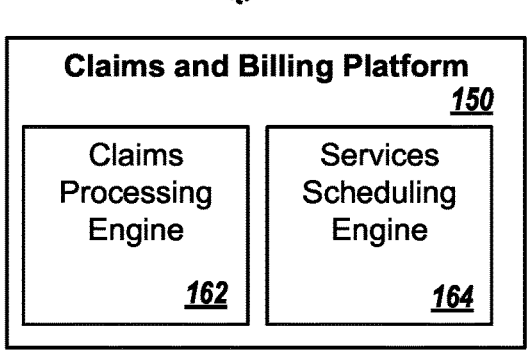

Claims and Billing Platform _150_

| | |
|---|---|
| Claims Processing Engine _162_ | Services Scheduling Engine _164_ |

Deductible monitoring settings

☑ Automated deductible monitoring _622_

90    _624_

Dollar threshold:

170    _626_    170    _628_

Periodic deductible monitoring is based on payer and plan information to streamline claims processing.    _630_

Save

620

Incomplete claims

| Incomplete 642 | Pick claims | Work oldest |

410

38  Verify account inconsistencies — Work ( 642a )
    Pending prior authorization ( 642b )
    Queued for deductible monitoring ( 642c )

High priority claims

3  Queued for submission - Manual submission 644a — Work

2360  Follow-up — Work

95  Denial 644c — Work

⚇ My claims viewed today

Claim assignments & reminders

| User 648 | Assigned claims 650 | Reminders due |
|---|---|---|
| ADMIN, BILLING | 3 | 0 |
| DOE, JANE | 6 | 0 |
| SMITH, ALVIN | 49 | 0 |
| BLACK, CHAD | 25 | 0 |
| NG, CHRISTINE | 1 | 0 |
| ZHU, FRANK | 41 | 0 |
| PETERSON, PETE | 18 | 0 |

Claims by status

| Status 652 | Claims | Assigned | Unassigned ⚘ |
|---|---|---|---|
| › Appealed | 9 | 4 | 5 |
| › Canceled | 305 | 1 | 304 |
| › Closed | 629 | 46 | 583 |
| › Credit posted | 2 | 2 | 0 |
| ⌄ Denied 652e | 95 | 68 | 27 |
|     Denial unresolved | 95 | 68 | 27 |
| › Follow-up | 2104 | 44 | 2060 |
| › Incomplete | 726 | 354 | 372 |
| › Queued for submission 652h | 20 | 1 | 19 |
| › Submitted 652i | 157 | 2 | 155 |
| › Suspended | 1137 | 8 | 1129 |

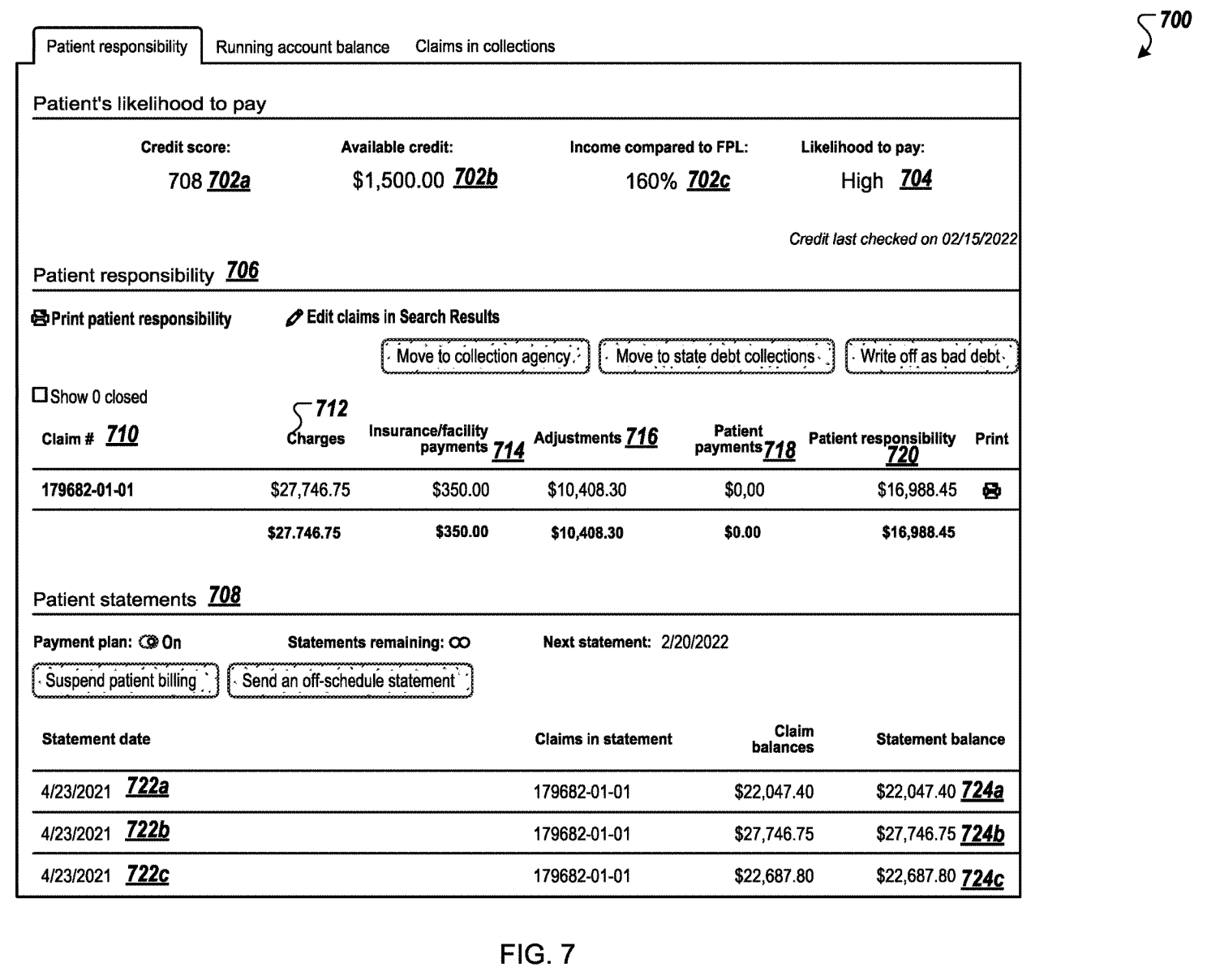

Patient responsibility | Running account balance | Claims in collections

Patient's likelihood to pay

| Credit score: | Available credit: | Income compared to FPL: | Likelihood to pay: |
|---|---|---|---|
| 708 _702a_ | $1,500.00 _702b_ | 160% _702c_ | High _704_ |

Credit last checked on 02/15/2022

Patient responsibility _706_

✎ Edit claims in Search Results

🖨 Print patient responsibility

· Move to collection agency · | · Move to state debt collections · | · Write off as bad debt ·

☐ Show 0 closed

_712_

| Claim # _710_ | Charges | Insurance/facility payments _714_ | Adjustments _716_ | Patient payments _718_ | Patient responsibility _720_ | Print |
|---|---|---|---|---|---|---|
| 179682-01-01 | $27,746.75 | $350.00 | $10,408.30 | $0.00 | $16,988.45 | 🖨 |
|  | $27,746.75 | $350.00 | $10,408.30 | $0.00 | $16,988.45 |  |

Patient statements _708_

Payment plan: ⦿ On    Statements remaining: ∞    Next statement: 2/20/2022

· Suspend patient billing · | · Send an off-schedule statement ·

| Statement date | Claims in statement | Claim balances | Statement balance |
|---|---|---|---|
| 4/23/2021 _722a_ | 179682-01-01 | $22,047.40 | $22,047.40 _724a_ |
| 4/23/2021 _722b_ | 179682-01-01 | $27,746.75 | $27,746.75 _724b_ |
| 4/23/2021 _722c_ | 179682-01-01 | $22,687.80 | $22,687.80 _724c_ |

FIG. 7

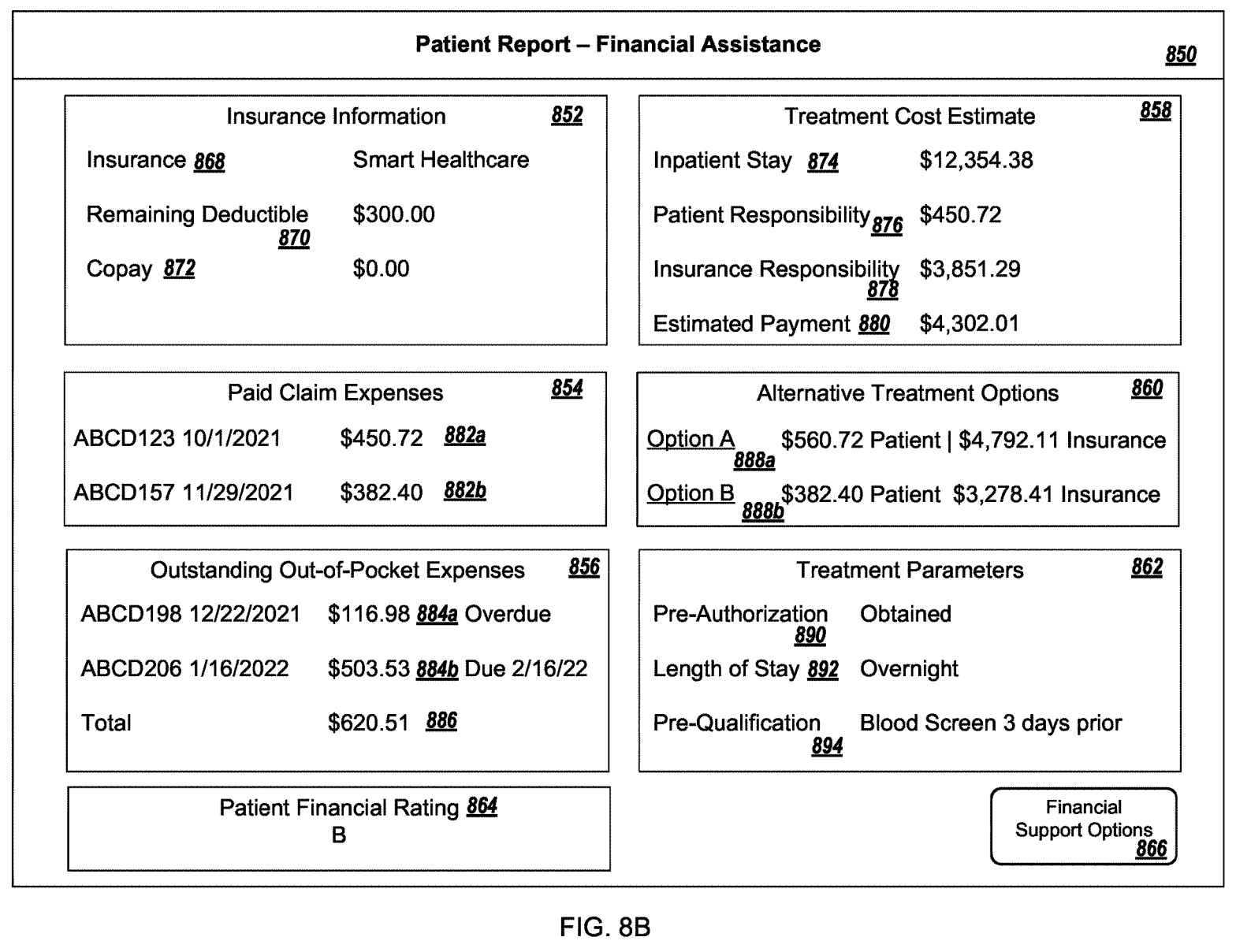

Patient Report – Financial Assistance    _850_

Insurance Information    _852_

Insurance _868_    Smart Healthcare

Remaining Deductible    $300.00
_870_

Copay _872_    $0.00

Paid Claim Expenses    _854_

ABCD123 10/1/2021    $450.72    _882a_

ABCD157 11/29/2021    $382.40    _882b_

Outstanding Out-of-Pocket Expenses    _856_

ABCD198 12/22/2021    $116.98 _884a_ Overdue

ABCD206 1/16/2022    $503.53 _884b_ Due 2/16/22

Total    $620.51    _886_

Patient Financial Rating _864_
B

Treatment Cost Estimate    _858_

Inpatient Stay _874_    $12,354.38

Patient Responsibility_876_    $450.72

Insurance Responsibility    $3,851.29
_878_

Estimated Payment _880_    $4,302.01

Alternative Treatment Options    _860_

Option A    $560.72 Patient | $4,792.11 Insurance
_888a_

Option B    $382.40 Patient  $3,278.41 Insurance
_888b_

Treatment Parameters    _862_

Pre-Authorization    Obtained
_890_

Length of Stay _892_    Overnight

Pre-Qualification    Blood Screen 3 days prior
_894_

Financial
Support Options
_866_

FIG. 8B

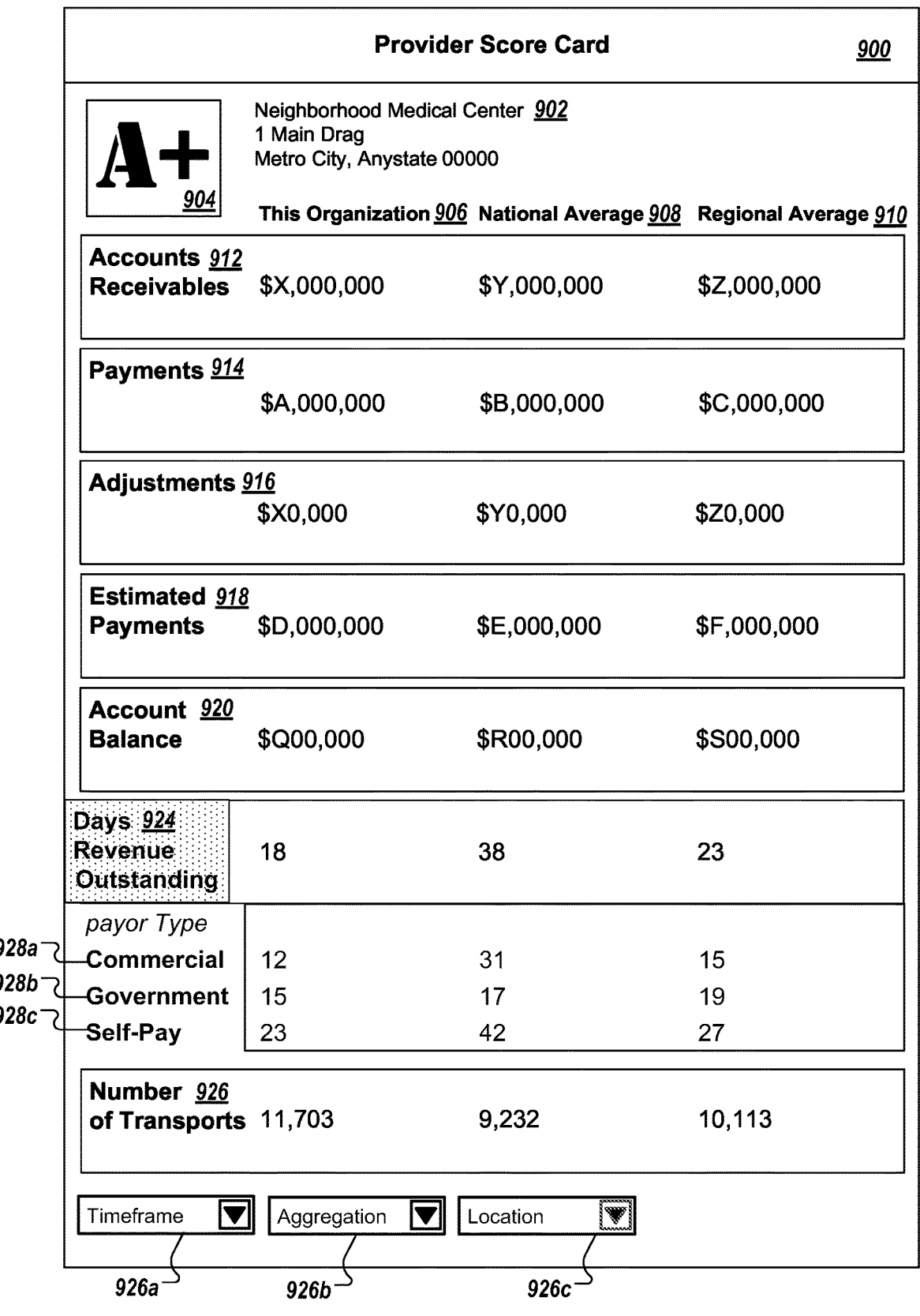

| Provider Score Card | | | 900 |
| --- | --- | --- | --- |

A+ 904

Neighborhood Medical Center 902
1 Main Drag
Metro City, Anystate 00000

| | This Organization 906 | National Average 908 | Regional Average 910 |
| --- | --- | --- | --- |
| Accounts 912 Receivables | $X,000,000 | $Y,000,000 | $Z,000,000 |
| Payments 914 | $A,000,000 | $B,000,000 | $C,000,000 |
| Adjustments 916 | $X0,000 | $Y0,000 | $Z0,000 |
| Estimated 918 Payments | $D,000,000 | $E,000,000 | $F,000,000 |
| Account 920 Balance | $Q00,000 | $R00,000 | $S00,000 |
| Days 924 Revenue Outstanding | 18 | 38 | 23 |
| *payor Type* | | | |
| Commercial 928a | 12 | 31 | 15 |
| Government 928b | 15 | 17 | 19 |
| Self-Pay 928c | 23 | 42 | 27 |
| Number 926 of Transports | 11,703 | 9,232 | 10,113 |

| Timeframe ▼ | Aggregation ▼ | Location ▼ |
| --- | --- | --- |
| 926a | 926b | 926c |

FIG. 9

Projected Revenue Report _1000_

Total Average Claim Payment _1002_

| Claim Count | Average Claim Payment | Total Payments |
|---|---|---|
| _1008_ 8 | _1010_ $1,258.53 | _1012_ $10,068.22 |

Average Claim Payment by Payor _1004_

| Payor Description | Claim Count _1014_ | Average Claim Payment _1016_ | Total Payments _1018_ |
|---|---|---|---|
| Payor 1 _1020a_ | 1 | $1,100.00 | $1,100.00 |
| Payor 2 _1020b_ | 4 | $1,829.15 | $7,316.59 |
| Payor 3 _1020c_ | 2 | $625.40 | $1,250.80 |
| Payor 4 _1020d_ | 1 | $400.83 | $400.83 |

Average Claim Payment by Payor and Policy _1006_

| Payor Description | Policy Description _1022_ | Claim Count _1024_ | Average Claim Payment _1026_ | Total Payments _1028_ |
|---|---|---|---|---|
| Payor 1 _1020a_ | Commercial | 1 | $1,100.00 | $1,100.00 |
| Payor 2 _1020b_ | Commercial | 4 | $1,829.15 | $7,316.59 |
| Payor 3 _1020c_ | Facility | 2 | $625.40 | $1,250.80 |
| Payor 4 _1020d_ | Medicare | 1 | $400.83 | $400.83 |

FIG. 10

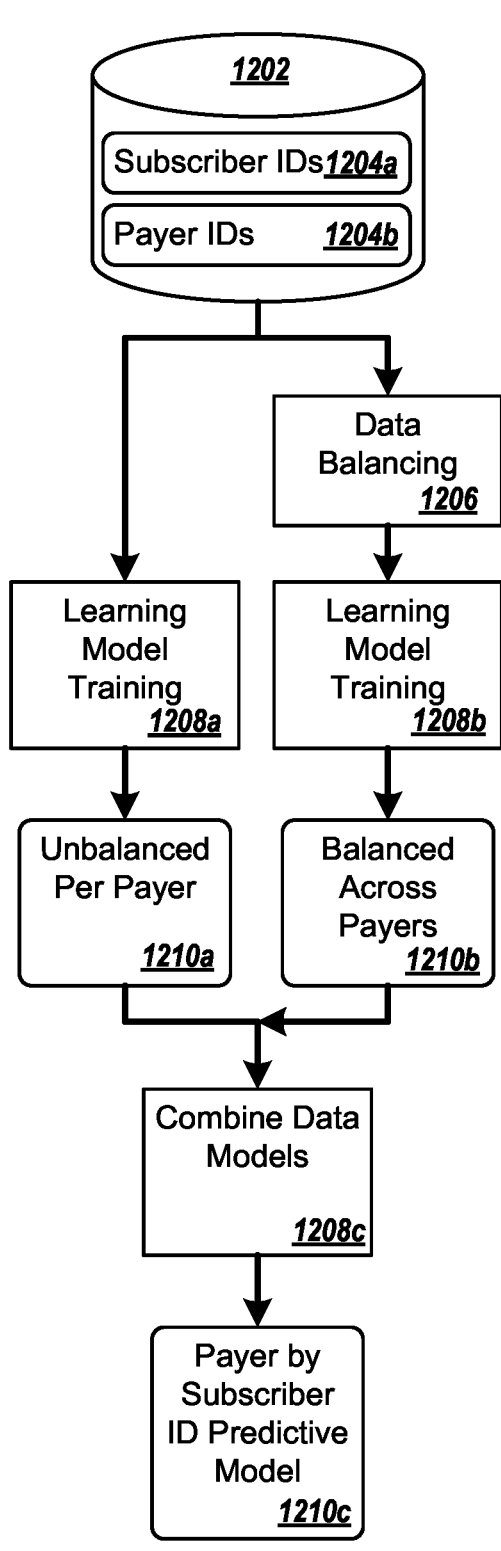
FIG. 12

SYSTEMS AND METHODS FOR MEDICAL CLAIMS ANALYTICS AND PROCESSING SUPPORT

RELATED APPLICATIONS

This application claims priority to U.S. Provisional Patent Application Ser. No. 63/325,729, entitled "Systems and Methods for Medical Claims Analytics and Processing Support," filed Mar. 31, 2022. All above identified applications are hereby incorporated by reference in their entireties.

BACKGROUND

Payers of health services and products, such as health insurance companies, federal and state health coverage providers including Medicare and Medicaid, and liability insurance companies provide payment coverage to a wide variety of medical providers. The medical providers include traditional brick and mortar service providers such as, in some examples, hospitals, physician practices, emergency rooms, urgent care facilities, and surgical centers. Further, medical providers can include mobile providers such as emergency medical services (EMS) providers, ambulance companies, and medical evacuation providers. Medical providers can include specialty care providers such as dental care providers, chiropractors, and physical therapists. Further, medical providers include prescription medical device companies such as contact lens retailers, wheelchair companies, and prosthetic device manufacturers. As technological solutions expand, more and more wearable prescription medical device companies are included within the span of health product coverage, including, in some examples, wearable glucose monitors, wearable nerve stimulation devices, and the ZOLL LifeVest® wearable cardioverter defibrillator. Each of the medical providers seek reimbursement from payers for services and products provided to patients, and each of the medical providers maintains records related to patients and payer remittance.

Rather than submitting reimbursement directly to each medical provider, payers are often billed via a billing company or a medical provider administration platform used by the medical provider for managing the claims and patient invoicing. The billing company or medical provider administration platform, for example, may streamline the complexities of claims processing and records keeping on behalf of the medical provider.

Medical claims submission and processing involves many complex steps to move from initiating claims preparation to receiving payment and involves numerous entities and databases. Claim verification, for example, oftentimes involves confirmation of patient information as well as payer information. In another example, determining the correct billing amount can involve numerous factors, such as patient co-pay amount, patient deductible, multiple insurers and/or liability insurance, and location where the medical services were rendered.

SUMMARY OF ILLUSTRATIVE EMBODIMENTS

In one aspect, the present disclosure relates to a system for providing automation and virtual assistance to medical claims processing, the system including a networked storage region including non-transitory computer readable media storing patient data corresponding to a number of patients, and payer data corresponding to a number of payers, and a predictive analytics computing platform including hardware logic and/or software logic configured for execution on processing circuitry, where the predictive analytics computing platform is configured to receive, from a claims processing system, claims data corresponding to a medical claim for a first patient, access, from the predictive analytics platform, a set of requirements corresponding to at least one first payer of the number of payers to which the medical claim is directed, where the set of requirements was generated at least in part through training at least one machine learning classifier with claims data corresponding to a subset of the number of patients having coverage provided by one or more payers of the at least one first payer, verify the claims data in view of the set of requirements, and provide predictive analytic output to the claims processing system responsive to verifying the claims data, the predictive analytic output including an indication of at least one of missing claims information or invalid claims information for the medical claim for the first patient.

In some embodiments, the predictive analytics platform includes a portal configured to receive the predictive analytic output, where the portal is configured to interoperate with a data resource access interface for claims and billing via an integration platform. The portal and the data resource access interface may interoperate via a Substitutable Medical Applications and Reusable Technologies (SMART®) on Fast Healthcare Interoperability Resources (FHIR®) integration platform. The integration platform may be configured to enable a user to access the claims and billing system and the predictive analytic output with a single sign-on operation by the user.

In some embodiments, the predictive analytics computing platform is configured to access the patient data corresponding to the number of patients and the payer data corresponding to the number of payers via a data exchange interface with an integration platform configured provide a Health Level 7 (HL7®) standard integration. The predictive analytics computing platform may be configured to access the patient data corresponding to the number of patients and the payer data corresponding to the number of payers via at least one application programming interface (API).

In some embodiments, the predictive analytics computing platform may be configured to receive, from a claims processing system, patient information corresponding to the medical claim, where the patient information includes at least one item of demographic data, cross-reference the patient information with the stored patient data to identify a patient record, apply at least a portion of the patient information to a machine learning classifier to estimate a likelihood of an individual identified by the patient information matching a patient identified by the patient record, and provide the predictive analytic output to the claims processing system, the predictive analytic output including at least an identifier corresponding to the patient record and an indication of the likelihood of matching. Providing the indication of the likelihood of matching includes indicating match or no match. Providing the indication of the likelihood of matching may include identifying at least one mismatching data element between the patient information and the patient record.

In some embodiments, receiving the claims data includes receiving the claims data from an electronic medical record. Receiving the claims data may include receiving the claims data responsive to data entry of at least a portion of the claims data by a user of the claims processing system. Receiving the claims data may include iteratively receiving at least portions of the claims data responsive to corresponding portions of data entry one or more of a number of fields of a medical claim form and iteratively verifying the at least portions of the claims data. Iteratively verifying the at least portions of the claims data may include identifying, based upon data entry in a given field of the number of fields, another field of the number of fields requiring information corresponding to the data entry in the given field. Based on the indication of the at least one of the missing claims information or the invalid claims information, the claims processing system may provide a prompting message to the user regarding the missing claims information and/or invalid claims information.

In some embodiments, verifying the claims data includes determining a likelihood of acceptance of the one or more procedure codes by the at least one payer. Determining the likelihood of acceptance of the one or more procedure codes may include cross-referencing the one or more procedure codes with a set of procedure codes accepted by the at least one payer. Determining the likelihood of acceptance of the one or more procedure codes may include executing at least one machine learning classifier to obtain a likelihood of approval of the one or more procedure codes. The predictive analytics computing platform may be configured to, when determining the likelihood of acceptance of a given procedure code of the one or more procedure codes is low, identify an alternative procedure code to given procedure code. The claims processing system may provide a prompting message to the user presenting, at a user interface, the alternative procedure code for acceptance by a user.

In some embodiments, the set of requirements was generated at least in part through training at least one machine learning classifier with a plurality of claims denied by the at least one first payer.

In some embodiments, verifying the claims data includes confirming receipt of information corresponding to a set of required data fields of a number of fields of a medical claim form. Confirming receipt of information corresponding to the set of required data fields may include executing at least one machine learning classifier trained to identify information corresponding to the set of required fields.

In some embodiments, the predictive analytics computing platform is configured to identify, using the claims data, at least one second payer for paying the medical claim. The predictive analytics computing platform may be configured to confirm patient eligibility for coverage via a payer account corresponding to at least a portion of the claims data.

In some embodiments, verifying the claims data includes determining pre-approval status corresponding to at least one procedure code of one or more procedure codes of the claims data. The pre-approval status may correspond to at least one of needed, not needed, pending, or obtained. Responsive to the pre-approval status of a given procedure code of the at least one procedure code i) corresponding to needed and ii) not corresponding to pending or obtained, the predictive analytics computing platform may be configured to request, from the at least one first payer via a network, pre-approval for the given procedure code. Determining the pre-approval status may include executing at least one machine learning classifier trained to determine a likelihood of pre-approval requirement based on the at least one first payer and the one or more procedure codes.

In some embodiments, the predictive analytics computing platform is configured to determine, responsive to a request from the claims processing system, a deductible status corresponding to a deductible value of at least one payer account corresponding to at least a portion of the claims data. Determining the deductible status may include determining whether the deductible value is below a threshold amount. Determining the deductible status may include determining an unpaid deductible amount corresponding to one or more open invoices and updating the deductible value by the unpaid deductible amount. Determining the deductible status may include accessing, via a network, the deductible value from a computing system of at least one payer corresponding to the at least one payer account. Determining the deductible status may include executing at least one machine learning classifier trained to determine a deductible update pattern based at least in part on at least one payer corresponding to the at least one payer account, and, based on the deductible update pattern indicating a stored deductible value has likely been updated, accessing, via a network, the deductible value from a computing system of the at least one payer. The predictive analytics computing platform may be configured to automatically identify the at least one first payer based on a subscriber identifier from the first patient.

In one aspect, the present disclosure relates to a method for generating a combined financial and clinical patient report, the method including obtaining, by processing circuitry, one or more procedure codes and patient information, accessing, by the processing circuitry using the patient information, a patient account and at least one patient medical record, identifying, by the processing circuitry via the patient account, a set of demographic information of the patient, and at least one payer providing coverage for medical services identified by the one or more procedure codes, identifying, by the processing circuitry via the at least one patient medical record, medical history information including at least one of i) one or more conditions of the patient, ii) one or more allergies of the patient, or iii) one or more medications of the patient, and preparing, by the processing circuitry for review at a graphical user interface, a report including the demographic information, the at least one payer, and at least a portion of the medical history information.

In some embodiments, the method includes calculating, by the processing circuitry using the one or more procedure codes and the at least one payer, a treatment cost estimate, where the treatment cost estimate includes a payer responsible amount and a patient responsible amount. The report may include one or more of a total cost of the treatment cost estimate, the payer responsible amount, or the patient responsible amount.

In some embodiments, the method includes identifying, by the processing circuitry based at least in part on the at least one payer, a copay amount, where calculating the patient responsible amount of the treatment cost estimate includes including the copay amount in the patient responsible amount. The report may include the copay amount. Calculating the treatment cost estimate may include executing at least one machine learning classifier trained to estimate costs based on procedure codes and payer information. The method may include determining at least one of a chronic condition, a physiological metric, or a diagnosis of the patient, where calculating the treatment cost estimate includes applying the at least one of the chronic condition, the physiological metric, or the diagnosis to one or more machine learning classifiers of the at least one machine learning classifier, where the one or more machine learning classifiers were trained to estimate costs based on procedure codes, payer information, and one or more chronic conditions, physiological metrics, or diagnoses.

In some embodiments, the method includes determining, by the processing circuitry based on the at least one payer, a remaining deductible amount. Determining the remaining deductible amount may include executing at least one machine learning classifier trained to determine a deductible update pattern based at least in part on the payer, reviewing a recency of the current deductible amount in view of the deductible update pattern, and, when the deductible update pattern is indicative of an updated deductible value being likely available, requesting, via a network, the updated deductible value from the at least one payer. Calculating the treatment cost estimate may include calculating the patient responsible amount in view of the remaining deductible amount. Determining the remaining deductible amount may include accessing a current deductible amount, searching for unpaid invoices corresponding to a patient identified by the patient information, calculating an outstanding deductible payment associated with any unpaid invoices, and subtracting the outstanding deductible payment from the current deductible amount. The report may include a listing of the any unpaid invoices. The method may include determining, by the processing circuitry based at least in part on the any unpaid invoices, a financial rating of the patient, where the report further includes the financial rating. Determining the financial rating may include searching for paid invoices corresponding to the patient, and determining the financial rating further based in part on the paid invoices. The report may include a listing of at least a portion of the paid invoices. Determining the financial rating may include obtaining a credit score for the patient, where the credit score was produced by a credit report agency, and determining the financial rating further based in part on the credit score. The financial rating may be presented on a letter grade scale. The report may include the remaining deductible.

In some embodiments, the method includes confirming, by the processing circuitry using the payer account information, patient eligibility for coverage via a payer account corresponding to the payer account information. The method may include executing, by the processing circuitry, at least one machine learning classifier trained to determine a likelihood of pre-approval requirement based on the at least one payer and the one or more procedure codes. The method may include requesting, by the processing circuitry from the payer via a network, pre-approval for the given procedure code.

In some embodiments, preparing the report includes preparing the report for review by emergency medical personnel. The method may include identifying, by the processing circuitry from the at least one patient medical record based at least in part on the one or more procedure codes, at least one diagnosis relevant to a treatment corresponding to the one or more procedure codes, where the report includes the at least one diagnosis.

In some embodiments, the method includes obtaining, by the processing circuitry, an indication of emergency medical intervention for the patient, where preparing the report includes preparing the report responsive to the indication. The one or more procedure codes may correspond to the emergency medical intervention.

In some embodiments, preparing the report includes preparing the report for review by the patient. Preparing the report may include preparing at least one interactive control where the control, when selected by the patient, provides the patient with editing access to at least a portion of the demographic information. Preparing the report may include identifying, within the report, at least one new information element. Identifying the at least one new information element may include preparing a message including identification of the at least one new information element.

In one aspect, the present disclosure relates to a system for generating a provider score card report presenting financial metrics comparisons between a subject service provider and peer service providers, the system including a networked storage region including non-transitory computer readable media storing provider data corresponding to a number of service providers, and remittance data corresponding to a number of medical claims, and a predictive analytics computing platform including hardware logic and/or software logic configured for execution on processing circuitry, where the predictive analytics computing platform is configured to obtain identification of a subject service provider, access a number of characteristics of the subject service provider, identify, based on at least a subset of the number of characteristics, a set of peer service providers sharing commonalities with the subject service provider among the subset of the number of characteristics, where the number of characteristics includes one or more of a geographic region, a service type, a size, or a tax classification, calculate, based at least in part on the remittance data for the subject service provider, a number of financial metrics corresponding to a set of financial measures, where the set of financial measures includes one or more of accounts receivables, payments, adjustments, account balance, or days revenue outstanding after provision of service, calculate, based at least in part on the remittance data across the set of peer service providers, a number of aggregate financial metrics corresponding to the set of financial measures, calculate, based at least in part on the remittance data for the subject service provider, a provider financial rating for the subject service provider, where the provider financial rating represents an objective rating in view financial status of other service providers, and prepare, for review at a graphical user interface, a report including the number of financial metrics, the number of aggregate financial metrics, and the provider financial rating.

In some embodiments, calculating the number of financial metrics includes calculating the financial metrics based on remittance data from a number of records from a number of time periods. Calculating the number of aggregate financial metrics includes calculating one or more of an average, a median, a count, a minimum, or a maximum.

In some embodiments, identifying the set of peer service providers includes identifying at least two sets of peer service providers, each set of service providers representing a different characteristic of the number of characteristics. Identifying the set of peer service providers may include identifying at least two sets of peer service providers, each set of service providers representing a different scope of one of the number of characteristics. A first set of the at least two sets of peer service providers may represent a wider geographic region, and a second set of the at least two sets of peer service providers may represent a narrower geographic region. Calculating the number of financial metrics may include calculating at least a first financial metric of the number of financial metrics across a set of dimensions, where the set of dimensions include one or more of a set of dates, a set of times, a payer type, a vehicle type, a clinical nature of transport, a level of service, a mode of care, a quality of care, a level of customer satisfaction, a set of locations, a claim submission type, or a fee basis type. The fee basis type may be one of contracted or non-contracted. The payer type may include a commercial payer and a government payer. The set of locations may include a set of operations base locations. The set of times may include months or years.

In some embodiments, calculating the provider financial rating is further based on one or more fiscal practices of the subject service provider. The one or more fiscal practices may include at least one of compliance, document practices, clean claims analysis, diagnostic coding analysis, timely filing practices, and claims pipeline. Calculating the provider financial rating may be further based on one or more provider business practices. The one or more provider business practices may include at least one of commercial payer contracts, facility contracts, debt setoff programs, and NEMSIS to reimbursement correlation.

In some embodiments, the provider financial rating is represented as a letter grade between A and F. The provider financial rating may be represented as a characterization. The characterization may be one of the following: poor, fair, good, very good, excellent, below average, average, or above average. Preparing the report may include preparing the report as an interactive report including at least one filter for filtering the financial metrics by one or more dimensions.

In one aspect, the present disclosure relates to a platform for distributing patient information in real-time among a number of medical systems, the platform including an information exchange service supporting transfer of data among a number of medical systems, a computer-aided dispatch (CAD) system of the number of medical systems, the CAD system including software logic configured for execution on processing circuitry and/or hardware logic, where the software logic and/or hardware logic is configured to perform CAD operations including identifying, in relation to a dispatch event involving an individual, dispatch information including location information identifying a location of the dispatch event, and demographic information identifying the individual, and transmitting, via the information exchange service, the dispatch information, a charting system of the number of medical systems, the charting system including software logic configured for execution on processing circuitry and/or hardware logic, where the software logic and/or hardware logic is configured to perform charting operations including obtaining, via the information exchange service, the dispatch information from the information exchange service, using at least a portion of the dispatch information related to patient demographics, preparing a clinical record, and transmitting, via the information exchange service, the clinical record, a predictive analytics system of the number of medical systems, the predictive analytics system including software logic configured for execution on processing circuitry and/or hardware logic, where the software logic and/or hardware logic is configured to perform analytics operations including obtaining, via the information exchange service, the portion of the dispatch information related to patient demographics, responsive to obtaining the portion of the dispatch information, accessing a data collection including a number of patient data records corresponding to a number of patients, automatically identifying, using the demographic information, a patient record in the data collection corresponding to the individual, generating a patient report including medical history information, where the patient report includes demographic information, at least one payer, and medical history information, and transmitting, via the information exchange service, the patient report. The patient report generated by the predictive analytics system may be distributed by the information exchange service to the hospital system and the charting system.

In some embodiments, the system includes a hospital system of the number of medical systems, the hospital system including software logic configured for execution on processing circuitry and/or hardware logic, where the software logic and/or hardware logic is configured to perform hospital operations including obtaining, via the information exchange service, the clinical record transmitted by the charting system, and generating an administrative record for admission of the individual. A hospital may include at least a portion of software logic and/or hardware logic of the hospital system. The patient report generated by the predictive analytics system may be distributed by the information exchange service to the hospital system. Hospital staff members may be provided access to review the patient report via the hospital system. A caregiver crew transferring the individual to the hospital in the medical transport vehicle may be provided access to review the patient report via the charting system. An EMS (Emergency Medical Services) version of the patient report provided for review by the caregiver crew may be different than a hospital version of the patient report provided for review by the hospital staff members. The hospital version of the patient report may include patient financial information excluded from the EMS version of the patient report. The hospital system may generate the administrative record in part using information provided by the predictive analytics system.

In some embodiments, the charting system prepares the clinical record in part using information provided by the predictive analytics system. The system may include a navigation system of the number of medical systems, the navigation system including software logic configured for execution on processing circuitry and/or hardware logic, where the software logic and/or hardware logic is configured to perform navigation operations including obtaining, via the information exchange service, at least the location information of the dispatch information from the information exchange service, generating a transportation record including navigation information representing transit to a location identified in the location information and to the hospital, and transmitting, via the information exchange service, the transportation record.

In some embodiments, the demographic information of the patient report includes at least one of an age, a gender, a height, a weight, or a body mass index (BMI) value. The at least one payer presented in the patient report may include payer details including at least one of a payer name, a plan name, a subscriber identifier, a deductible level, a remaining deductible amount, or a copay amount. The medical history information of the patient report may include one or more of at least one medication, at least one allergy, at least one chronic condition, or at least one vaccination.

In one aspect, the present disclosure relates to a method for providing automation and virtual assistance to medical claims processing, the method including obtaining, from an electronic medical record, claims data including a portion of a set of information for filling in a medical claim form for presentation to a payer, where the claims data includes patient information and payer account information, and entering an automated claim processing routine, where the automated claim processing routine includes accessing, using the patient information, a patient account, confirming, by processing circuitry, consistency between the patient information and patient data in the patient account, populating, by processing circuitry, the medical claim form using the claims data and the patient information, after populating the medical claim form, verifying, by the processing circuitry, contents of the medical claim form in view of a set of requirements, where at least a portion of the set of requirements is specific to the payer, confirming, by the processing circuitry using the payer account information, patient eligibility for coverage via a payer account corresponding to the payer account information, and queuing, by the processing circuitry, the medical claim form for submission. Upon lack of success in a) the confirming consistency between the patient information and the patient data, b) the verifying of the contents of the medical claim form, or c) the confirming of the patient eligibility for coverage, the automated claim processing routine may be exited, and the medical claim form may be added, by the processing circuitry, to a manual processing queue.

In some embodiments, obtaining the electronic medical record includes importing the electronic medical record via a network from a remote computing system. Accessing the patient account may include uniquely identifying the patient among a number of patient records based on the patient information. Confirming the consistency may include supplementing the patient information with one or more elements of the patient data. Confirming the consistency may include correcting one or more elements of the patient information based on the patient data. Confirming consistency between the patient information and the patient data includes executing a machine learning classifier to estimate a likelihood of a matching patient based on the patient information and the patient data.

In some embodiments, populating the medical claim form includes populating an electronic medical claim form for transmission to the payer over a network. Populating the medical claim form may include populating, at a user interface, a set of data fields corresponding to portions of the medical claim form for review by a user. The automated claim processing routine may include, after populating the set of data fields corresponding to the portions of the medical claim form at the user interface, receiving, by the processing circuitry via the user interface, one or more inputs from the user. The one or more inputs may include data entry in at least one field of the set of data fields. Verifying the contents of the medical claim form may include iteratively verifying the contents of the medical claim form responsive to the data entry in the at least one field. Iteratively verifying the contents of the medical claim form may include identifying, based upon data entry in a given field of the at least one field, another field of the set of data fields requiring information corresponding to the data entry in the given field. Iteratively verifying the contents of the medical claim form may include prompting, at the user interface, entry of additional information in the set of fields.

In some implementations, verifying the contents of the medical claim form in view of the set of requirements includes determining a likelihood of acceptance of the one or more procedure codes by the payer. Determining the likelihood of acceptance of the one or more procedure codes may include cross-referencing the one or more procedure codes with a set of procedure codes accepted by the payer. Determining the likelihood of acceptance of the one or more procedure codes may include executing at least one machine learning classifier to obtain a likelihood of approval of the one or more procedure codes. The automated claim processing routine may include, when determining the likelihood of acceptance of a given procedure code of the one or more procedure codes is low, identifying, by the processing circuitry, an alternative procedure code to given procedure code. The automated claim processing routine may include presenting, by the processing circuitry at a user interface, the alternative procedure code for acceptance by a user.

In some embodiments, verifying the contents of the medical claim form in view of the set of requirements includes confirming entry of information in a number of required fields of the set of data fields. The method may include executing, by the processing circuitry, at least one machine learning classifier trained to identify the number of required fields based at least in part on the payer. The automated claim processing routine may include presenting, by the processing circuitry at a user interface, a prompt for a user to complete data entry in one or more fields of the set of data fields.

In some embodiments, the automated claim processing routine includes determining, by the processing circuitry, a deductible status corresponding to a deductible value of the payer account. Determining the deductible status may include determining whether the deductible value is below a threshold amount. Determining the deductible status may include determining an unpaid deductible amount corresponding to one or more open invoices and updating the deductible value by the unpaid deductible amount. Determining the deductible status may include accessing, via a network, the deductible value from a computing system of the payer. Determining the deductible status may include executing at least one machine learning classifier trained to determine a deductible update pattern based at least in part on the payer, and, based on the deductible update pattern indicating a stored deductible value has likely been updated, accessing, via a network, the deductible value from a computing system of the payer. Upon determining the deductible status is indeterminate or above a threshold value, the automated claim processing routine may be exited, and the medical claim form may be added, by the processing circuitry, to an automated hold queue pending deductible processing. Adding the medical claim form to the automated hold queue may include setting, based at least in part on the payer, a deductible monitoring time period. The deductible monitoring time period may be further based in part on one or more of a geographical location, a day of the week, or a day of the month.

In some embodiments, queuing the medical claim form for submission includes queueing, responsive to receiving input via a user interface from a user accepting a set of medical claim form information as completed, the medical claim form for submission to the payer. Queuing the medical claim form for submission may include adding, based on payer preferences, the medical claim form to a manual submission queue for manual submission.

In some embodiments, adding the medical claim form to the manual processing queue includes including at least one reason for moving the medical claim form from the automated claim processing routine to the manual processing queue.

In some embodiments, the automated claim processing routine includes determining, by the processing circuitry, pre-approval status corresponding to at least one procedure code of one or more procedure codes of the medical claim form, where the pre-approval status corresponds to at least one of needed, not needed, pending, or obtained. Responsive to the pre-approval status of a given procedure code of the at least one procedure code i) corresponding to needed and ii) not corresponding to pending or obtained, the automated claim processing routine may include requesting, by the processing circuitry from the payer via a network, pre-approval for the given procedure code. Determining the pre-approval status may include executing at least one machine learning classifier trained to determine a likelihood of pre-approval requirement based on the payer and the one or more procedure codes. Responsive to the pre-approval status corresponding to pending, the automated claim processing routine may be exited, and the medical claim form may be added, by the processing circuitry, to an automated hold for pre-approval queue.

In one aspect, the present disclosure relates to a system for generating predictive analytics for patient medical records, the system including a networked storage region including non-transitory computer readable media storing data resources including patient data corresponding to a number of first patients, and payer data corresponding to a number of payers, and a predictive analytics computing platform communicatively coupled to the networked storage region and including hardware logic and/or software logic configured for execution on processing circuitry, where the predictive analytics computing platform is configured to receive at least one subscriber identifier associated with a second patient, analyze the at least one subscriber identifier based on machine learning derived from the patient data corresponding to the number of first patients and the payer data corresponding to the number of payers, based on the analysis of the at least one subscriber identifier, identify one or more payers associated the at least one subscriber identifier as one or more predicted payers associated with the at least one subscriber identifier, and generate predictive analytic output including the one or more predicted payers associated with the at least one subscriber identifier.

In some embodiments, analyzing the at least one subscriber identifier may include analyzing the at least one subscriber identifier in view of demographic information associated with a respective subscriber identifier. The demographic information may include at least one of a subscriber's geographic region, a geographic region of a subscriber's employer, a subscriber's age, or a subscriber's military status. Receiving the at least one subscriber identifier may include receiving the demographic information. Analyzing the at least one subscriber identifier based on the machine learning may include applying one or more machine learning classifiers to the at least one subscriber identifier, where each machine learning classifier of the one or more machine learning classifiers is trained using a number of subscriber identifiers, each subscriber identifier associated with a respective confirmed payer identifier of the number of payers. The number of subscriber identifiers may be associated with at least a subset of the number of first patients. Each machine learning classifier of the one or more machine learning classifiers may be trained using a demographic information portion of the patient data. The generated predictive analytic output may include a confidence level or rating associated with each payer of the one or more predicted payers as generated by the machine learning. Generating the predictive analytic output may include ranking the one or more predicted payers by the confidence level or rating associated with each payer. Receiving the at least one subscriber identifier may include receiving a set of subscriber identifiers. Generating the predictive analytic output may include generating a set of correlations including a respective correlation between each subscriber identifier of the set of subscriber identifiers and at least one respective payer of the one or more predicted payers identified for each subscriber identifier of the set of subscriber identifiers. The predictive analytic output may include, for each subscriber identifier of the at least one subscriber identifier, up to three predicted payers of the number of payers. The data resources may include provider data corresponding to a number of providers. The predictive analytics platform may be configured to receive medical expense information for a third patient, analyze the medical expense information for the third patient based on machine learning derived from one or more of the patient data corresponding to the number of first patients, the payer data corresponding to the number of payers, and the provider data corresponding to the number of providers, and, based on the analysis of the medical expense information, generate another predictive analytic output including prior authorization information for a payer associated with the third patient. The prior authorization information may include an indication that a payer associated with the third patient likely requires an authorization of a medical expense prior to an incurrence of that medical expense by the third patient. The indication may include contact information for requesting the authorization. The indication may include an indication of issuance of a request for the prior authorization; and the predictive analytics computing platform may be configured to issue the request for the prior authorization to the payer associated with the third patient. The second patient and the third patient may be a same patient and the payer associated with the third patient may be one of the one or more predicted payers. The predictive analytics computing platform may be configured to receive a request from a medical claims processing system for a deductible status for a payer account corresponding to a third patient, analyze the deductible status based on machine learning derived from one or more of the patient data corresponding to the number of first patients, the payer data corresponding to the number of payers, and the provider data corresponding to the number of providers, based on the analysis of the deductible status, generate predictive analytic output including a deductible update pattern based at least in part on a payer corresponding to the payer account corresponding to the third patient, and provide the deductible update pattern to the medical claims processing system. The predictive analytics platform may be configured to, based on the deductible update pattern indicating a stored deductible value has likely been updated, access, via a network, an updated deductible value from a computing system of the payer, and provide the updated deductible value to the medical claims processing system. The second patient and the third patient may be a same patient and the predictive analytics computing platform may be configured to identify the payer associated the payer account as at least one of the one or more predicted payers. The predictive analytic output may include an indication regarding a deductible status of at least one payer account corresponding to the at least one subscriber identifier and a first payer of the one or more predicted payers. The indication regarding the deductible status may include a deductible value of a first payer account of the at least one payer account. The predictive analytics computing platform may be configured to determine an unpaid deductible amount corresponding to one or more open invoices, and may update the deductible value by the unpaid deductible amount. The predictive analytics computing platform may be configured to receive one or more medical billing claims related to the at least one subscriber identifier, calculate an unpaid deductible amount corresponding to the one or more medical billing claim, and adjust the deductible value by the unpaid deductible amount. The predictive analytic computing platform may be configured to generate a set of claims data field requirements for medical billing claims submissions to at least one payer of the one or more predicted payers, where the set of requirements was generated at least in part through training at least one machine learning classifier with claims data corresponding to the number of payers, generate another predictive analytic output including the set of claims data field requirements, and provide the predictive analytic output to a medical claims and billing portal. The medical claims and billing portal may be configured to apply the set of requirements to claims data of an in-progress medical claim to verify the claims data. Verifying the claims data may include identifying at least one of missing claims information or invalid claims information. The predictive analytic output may include patient information associated with the subscriber identifier, where the patient information may include at least one item of patient demographic data. The predictive analytics computing platform may be configured to access the patient information from a computing system of a first payer of the one or more predicted payers. The system may include a medical claims and billing portal accessed by the user, where the medical claims and billing portal may be configured to compare at least a portion of the patient information with stored patient data to identify a patient record. The medical claims and billing portal may be configured to update the patient record based on the comparison. The predictive analytics computing platform may be communicatively coupled to the networked storage region via an integration platform. The integration platform may include at least one data communications integration that may be configured to convert one or more of the patient data, the payer data, and provider data corresponding to a number of providers to a common communications standard. The common communications standard may include at least one of a Health Level 7 (HL7®) Standard, a Fast Healthcare Interoperability Resources (FHIR®), or a Substitutable Medical Applications and Reusable Technologies (SMART®) on FHIR® standard. The networked storage region may include one or more data resource access interfaces configured to interact with a respective data resource provided by the networked storage region, and the integration platform may enable a user of a respective data resource access interface to access the respective data resource access interface and the predictive analytics output via a single sign-on interface provided at the respective data resource access interface. The integration platform may enable automatic data transfer of the predictive analytics output from the predictive analytics computing platform to the data resource access interface. The predictive analytics computing platform may be configured to provide the predictive analytics output at a claims and billing platform, and the integration platform may enable automatic data transfer of the predictive analytics output from the claims and billing platform to the data resource access interface. The single sign-on interface may enable the user to enter login credentials used to connect to both of the data resource access interface and a reporting portal of the predictive analytics computing platform. the predictive analytics computing platform may be communicatively coupled to the networked storage region via one or more application programming interfaces (APIs).

The foregoing general description of the illustrative implementations and the following detailed description thereof are merely exemplary aspects of the teachings of this disclosure and are not restrictive.

BRIEF DESCRIPTION OF THE DRAWINGS

The accompanying drawings, which are incorporated in and constitute a part of the specification, illustrate one or more embodiments and, together with the description, explain these embodiments. The accompanying drawings have not necessarily been drawn to scale. Any values dimensions illustrated in the accompanying graphs and figures are for illustration purposes only and may or may not represent actual or preferred values or dimensions. Where applicable, some or all features may not be illustrated to assist in the description of underlying features. In the drawings:

FIG. 1D is a block diagram of an example system for providing predictive analytics generated by a predictive analytics platform to a claims and billing platform;

FIG. 6A through FIG. 6C are screen shots of example medical claim entry user interfaces incorporating a virtual assistant;

FIG. 7 illustrates an example patient likelihood to pay report;

FIG. 8B illustrates an example medical financial information for a patient report card;

FIG. 9 illustrates an example provider score card;

FIG. 10 illustrates an example projected revenue report for a provider;

FIG. 11D and FIG. 12 illustrate flow diagrams of example processes for training machine learning models for automatically identifying likely payers based on subscriber identifiers.

DETAILED DESCRIPTION OF ILLUSTRATIVE EMBODIMENTS

Figure 1A:
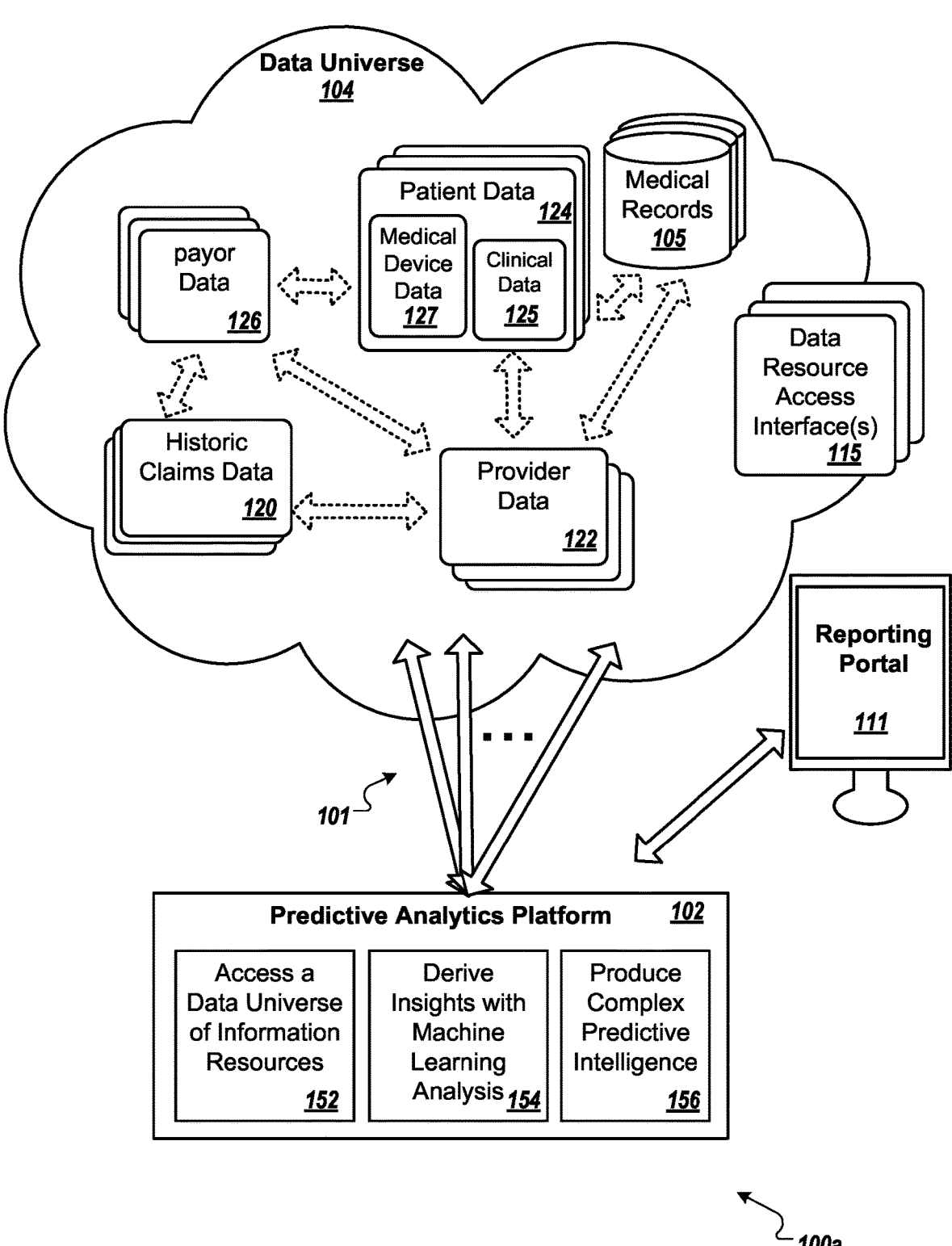
FIG. 1A is a process flow diagram of an example process for obtaining complex predictive intelligence from a predictive analytics platform.

The description set forth below in connection with the appended drawings is intended to be a description of various, illustrative embodiments of the disclosed subject matter. Specific features and functionalities are described in connection with each illustrative embodiment; however, it will be apparent to those skilled in the art that the disclosed embodiments may be practiced without each of those specific features and functionalities.

Reference throughout the specification to "one embodiment" or "an embodiment" means that a particular feature, structure, or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments. Further, it is intended that embodiments of the disclosed subject matter cover modifications and variations thereof.

It must be noted that, as used in the specification and the appended claims, the singular forms "a," "an," and "the" include plural referents unless the context expressly dictates otherwise. That is, unless expressly specified otherwise, as used herein the words "a," "an," "the," and the like carry the meaning of "one or more." Additionally, it is to be understood that terms such as "left," "right," "top," "bottom," "front," "rear," "side," "height," "length," "width," "upper," "lower," "interior," "exterior," "inner," "outer," and the like that may be used herein merely describe points of reference and do not necessarily limit embodiments of the present disclosure to any particular orientation or configuration. Furthermore, terms such as "first," "second," "third," etc., merely identify one of a number of portions, components, steps, operations, functions, and/or points of reference as disclosed herein, and likewise do not necessarily limit embodiments of the present disclosure to any particular configuration or orientation.

Furthermore, the terms "approximately," "about," "proximate," "minor variation," and similar terms generally refer to ranges that include the identified value within a margin of 20%, 10% or preferably 5% in certain embodiments, and any values therebetween. Additionally, a "payer" may be interchangeably referred to as a "payor" in a medical context.

All of the functionalities described in connection with one embodiment are intended to be applicable to the additional embodiments described below except where expressly stated or where the feature or function is incompatible with the additional embodiments. For example, where a given feature or function is expressly described in connection with one embodiment but not expressly mentioned in connection with an alternative embodiment, it should be understood that the inventors intend that that feature or function may be deployed, utilized or implemented in connection with the alternative embodiment unless the feature or function is incompatible with the alternative embodiment.

Aggregation and analysis of the data maintained by a wide range of distributed and independent data sources enables a prediction and estimation of medical claims payments. These data sources include, but are not limited to, medical providers, billing companies, medical provider administration platforms, medical and liability insurance companies, credit and banking institutions, patient health records, and employment databases and are referenced herein as part of a "data universe" of information. When aggregated and analyzed by a predictive analytics platform as described herein, historic trends and patterns within the data available from the data universe enables the prediction and estimation of future medical claims payments. In the absence of the predictive analytics platform described herein, the one or more data sources of the data universe may not be accessible from a single platform outside of the data universe. These data sources may be independent, separated, and/or communicatively uncoupled data resources. The predictive analytics platform described herein provides a capability to access and aggregate data from the disparate data resources of the data universe. Without the predictive analytics platform, these disparate data resources would remain separated and disconnected and the predictive analytic output derived from the resources by virtue of the capability to access and aggregate would not be realized. In some implementations, the predictive analytics platform may enable access and aggregation of the data in the data universe in real-time or in a clinically actionable time (e.g., seconds or minutes).

The systems and methods described herein provide at least several benefits for patient care. As one example, these systems and methods enable a fast and accurate prediction and estimation of future medical claims payments. This enables patients to receive accurate information about their insurance coverage and benefits early in the process of their medical care. For example, the system may be able to anticipate and predict out-of-pocket costs and payment options for elective surgeries. Also, the system may provide a patient report card combining medical history with claims history, upcoming visits, insurance information, and other important features. Thus, the patient is empowered by informed access to a holistic view of medical and payment history (e.g., combining insurance, doctor visit, and lab records in one spot). The systems and methods herein also enable health care providers to devote more of their staff and financial resources to patient care than to billing and collections. Further, more accurate revenue predictions for health care providers enable these providers to make informed decisions on the staffing and medical equipment purchases to better serve the needs of their patients.

The platform as described herein creates a predictive model based on a hybrid of data for a particular patient, data for payers associated with the particular patient, data for providers associated with the particular patient, and data for other patients, payers, and providers. The predictive model derived from this hybrid of data may provide a prediction and estimation for a medical claim for the particular patient. The platform may utilize demographic and insurance coverage discovery to further improve the accuracy and timeliness of the predictions and estimations. Through a discovery process, the platform described herein may find and identify information relevant to a patient and/or a patient's medical claim that may be unknown and/or unavailable to the patient, a payer, and/or a provider prior to the discovery process or information of which the patient, payer, and/or provider was unaware of prior to the discovery process. The data hybrid and the predictive analytics applied to this hybrid data, as described herein, enables accurate, real-time, and interactive payment estimations. As described in examples provided herein, these real-time estimations may enable interactive claims preparation that maximize remittances and minimize collection times, enable interactive claims submissions that maximize remittances, and enable real-time pre-payment calculations. Additionally, the real-time estimations enable medical provider decisions that improve the efficacy and efficiency of that care. For example, the billing, demographic, and coverage information provided by the predictive analytics platform may enable immediate transport to preferred providers within a patient's insurance coverage. The predictive analytics platform enables all of these real-time services at high confidence levels and with financial accuracy because of the hybrid nature of the data universe accessed by this platform. As an additional benefit, the systems and methods described herein improve billing accuracy, completeness, and timeliness of collections, thereby enabling medical providers to capture revenue that has heretofore been missed and to reduce the time and expense spent on performing transactions to obtain information.

The trends uncovered through analysis of historic information in the data universe enable accurate predictions of the likelihood of a patient and a payer to remit medical claims payments. The historic information, in some examples, may include services rendered, products sold, patient demographic information, patient insurance information, and remittance received from various payers to reimburse provision of medical services and products. The data universe may further include information regarding the various payers and the payer plans, such as copayment levels, deductible amounts, reimbursement eligibility requirements, and reimbursement amounts along with information regarding other patients and information regarding particular procedures, patients, and payers according to geographic locations.

The inventors recognized that, by applying machine learning algorithms and data analytics to information across the wide range of data sources included in the data universe, medical providers may be supplied with complex predictive intelligence, such as virtual claims processing assistance, claims analysis services to reduce denials, payer identification based on subscriber identifiers, prior authorization and deductible anticipation intelligence to ensure timely and accurate cost allotments. Thus, systems and methods described herein provide a technical solution to the technical problem of lack of complete information from disparate sources and difficulty in translating and applying claims submission rules for a variety of payers. Further, the inventors recognized that in combining data sources and applying machine learning analysis, the resultant data analytics may support real-time or near-real-time decision making that had not previously been possible, such as rapid patient pre-approval for medical procedures and prescription products. Thus, systems and methods described herein additionally provide a technical solution to the technical problem of overcoming resource availability obstacles and reimbursement obstacles to automatically deploy resources to patients in need in a timely manner, thereby improving patient outcomes while improving the bottom line. Additionally, the systems and methods described herein provide a technical solution to the technical problem of aggregating clinical and financial information for a patient across the scope of medical care (e.g., from a 911 call, to EMS treatment, to hospital treatment, to release and billing) to provide accurate and actionable clinical and financial support for patients. Further the systems and methods described herein provide a technical solution to the technical problem of automatically transferring data between platforms and resources. As described herein, an integration platform can apply a standard data format to data that is otherwise in disparate formats and controlled by entities that lack intercommunications, thereby, in some embodiments, enabling the automatic transfer with an additional benefit of single sign-on procedures. The automatic transfer further improves accuracy of medical data reporting and record keeping and improves the continuity and consistency of this data over a range of medical providers and payers.

In one aspect, the present disclosure relates to a predictive analytics platform developed to harness the intelligence of data records compiled in a data universe to supply claims processing predictive intelligence and financial analytics to medical providers. Turning to FIG. 1A, an example of a system for generating and applying predictive analytics as described herein is shown. The system 100a includes a predictive analytics platform 102 in communication with a data universe 104 and a reporting portal 111, the predictive analytics platform 102 being configured for performing machine learning analysis on the data universe 104 of information resources to produce complex predictive intelligence and apply that predictive intelligence to medical claims. The reporting portal 111 may enable a person to initiate, inspect, receive, or otherwise handle a data output from the predictive analytics platform 102 that may or may not be associated with a medical billing claim. For example, such a report may include a pre-approval report, a deductible report, a subscriber identification report, a patient report card, a provider report card, or other output available from the predictive analytics platform 102. Additionally, although illustrated in FIG. 1A as a monitor or display screen, the reporting portal 111 is not limited to a physical display. Rather, the reporting portal 111 may refer to a physical display, an application enabling access to the predictive analytic output, and/or to the predictive analytic output from software or applications provided by the predictive analytics platform 102. The predictive analytic output may be in various forms including a graphic representation on a display screen, a data file, or a combination thereof.

The predictive analytics platform 102 is configured to access 152 the data universe 104 that includes multiple information resources. The information resources may include, for example, but not limited to one or more sources of historic claims data 120, one or more sources of medical provider data 122, one or more sources of patient data 124, one or more sources of payer data 126, and one or more sources of device data 127 which may include medical device data. The data universe 104 may further include one or more medical records database(s) 105 which may include electronic medical or health records (EMR, EHR) and/or electronic patient care records (ePCR).

The patient data 124 may include clinical data 125 and/or medical device data 127. The clinical data 125 may originate from the medical records 105 and/or may be provided to a patient medical record by a caregiver at the point of care. The medical records 105 may include, for example, electronic healthcare records (EHRs) associated with a hospital or hospital system, a health information exchange (HIE), an electronic patient care record (ePCR) database, a medical insurance database, a pharmacy database, etc. In various implementations, the clinical data 125 may include one or more of the types of information shown in FIG. 8A as discussed in more detail below.

The medical device data 127 may be data from one or more medical devices used to care for a patient. In various implementations, the medical device data 127 may be provided to a patient medical record by a caregiver and/or may be reported to the patient data resource 124 automatically from the one or more medical devices (e.g., the medical devices 847 as shown in FIG. 8C). For example, the one or more medical devices may include external medical devices, implanted medical devices, and/or insertable medical devices. The medical devices may be external wearable devices, either by caregivers or by patients and/or may include non-wearable devices, like a patient monitor/defibrillator, designed to rest on a floor or a table but not supported by the patient's body. The medical device may be a therapy delivery device, a sensor device, a monitoring device, or a combination thereof. For example, the medical devices may include an external defibrillator (e.g., a patient monitor/defibrillator or an automated external defibrillator (AED)), a trauma kit, an automated compression device, a portable ventilation device, a drug delivery device and/or an ultrasound imaging device. Additionally, the one or more medical devices may include sensors such as, but not limited to, a compression sensor, an SpO2 sensor, a CO2 sensor, a non-invasive blood pressure (NIBP) sensor, electrodes (e.g., sensing electrodes and/or therapy electrodes), an airway pressure sensor, a pneumotachometer, an airflow sensor, a temperature sensor, a Doppler blood flow sensor, an invasive blood pressure (IBP) sensor, a continuous blood pressure sensor, an intubation tube, a mask, a nasal cannula, or a spirometer.

The predictive analytics platform 102 is communicatively coupled via multiple networked connections 101 to the disparate resources of the data universe 104. The data resources from the various entities and sources in the data universe 104 may include patient data corresponding to a plurality of patients, payor data corresponding to a plurality of payers, provider data corresponding to a plurality of providers, and/or combinations thereof. These resources may be physically separated (e.g., geographically separated and/or resources associated with physically separated servers) and/or communicatively separated (e.g., associated with different business entities and/or accounts where there communicative couplings are unavailable between entities and/or accounts). For example, the various medical record(s) sources 105 may be associated with different hospital or medical provider systems, the one or more sources of provider data 122 may be associated with different medical service providers, the one or more sources of payor data may be associated with different insurance companies, etc. There may be instances of communications between some of the entities in the data universe 104, as illustrated by the dotted two way arrows shown in FIG. 1A. For example, a medical provider may access patient data for their own patients without access to the patient data for patients associated with a different provider, a medical provider may access insurance payor data, each payor may access their own historic claims data without access to the historic claims data of another payor, etc.

However, none of the entities within the data universe 104 are a single aggregator of the data in these various sources within the data universe 104. Additionally, none of the entities within the data universe 104 have access to every other entity within the data universe 104. The predictive analytics platform 104 as described herein provides the only possible global access to the disparate entities of the data universe 104. As such, the data universe 104 is a networked storage region with limited connections amongst the entities of the data universe 104 but with networked connections available from all of the entities of the data universe 104 to the predictive analytics platform 102.

In addition, one or more resources of the data universe 104 may be associated with one or more data resource access interface(s) 115. A data resource access interface is configured to interact with a respective data resource. The data resource access interface(s) 115 (e.g., access software, hardware, firmware, and combinations thereof) may enable the various entities of the data universe to receive and store data and/or to provide access to previously stored data). In an implementation, the access interface(s) 115 may enable automated computing systems and/or users, which may include providers, patients, and/or payers, to populate the data resources and/or access or create medical records. The access interface(s) may enable data transfer between various data universe entities. For example, an access interface 115 may enable a recorder of patient data 124 to access data from or provide data to the medical records 105. As another example, an access interface 115 may enable a medical claims recorder to access data from or provide data to a payor, provider, or claims and billing platform. Importantly, the data resource access interface(s) provide access to a respective data resource of the data universe 104. However, no single data resource access interface(s) 115 provides access to all of the entities of the data universe 104. Where a first payer, provider, or patient resource of the data universe 104 provides instances of communications with a second payer, provider, or patient resource, a data resource access interface Returning to the predictive analytics platform 102, the accessing 152, in some embodiments, includes accessing a set of records maintained by or related to historic claims made by one or more providers, such as historic claims data 120 for multiple patients and patient data 124. The historic claims data 120, in some examples, may include reference codes as discussed in relation to the procedure codes 114*a,b* above, as well as, in some examples, dates of medical services, location(s) of medical services, patient identifiers, payer identifiers, payer plan and/or group identifiers, payer pre-approval references, invoice amounts, reimbursement amounts, identifiers of responsible parties if not the patient, a portion of patient demographic information such as name, address, date of birth, gender, and/or relationship to responsible party, and/or accident information (e.g., regarding an indemnity claim). The patient data 124, in some examples, may include patient identifiers, geographic regions or address portions (e.g., city, state, and/or zip code), age or age ranges, medical history identifiers (e.g., co-morbidities, prescription data, prior major medical services such as surgeries, etc.), payer identifiers, payer plan identifiers, and/or payer group identifiers.

In some embodiments, the accessing 152 includes accessing a set of records maintained by or provided by a third party, such as a patient financial data portion of the patient data 124, provider data 122, and/or payer data 126. The patient financial data, for example, may be accessed by obtaining a credit score or credit report from a credit reporting agency or financial institution. In particular, the patient financial data may be obtained through requesting a patient financial clearance or risk analysis related to medical debt from a credit reporting agency specializing in healthcare reimbursement data, such as TransUnion LLC of Chicago, Illinois or Experian Health by Experian Information Solutions, Inc. of Costa Mesa, CA. The patient financial data, in some embodiments, includes financial data related to a responsible party, such as a parent or spouse of the patient. The payer data 126, in some implementations, includes coverage details for insurance plans for each of a collection of payers. The payers may include health insurance payers, medical insurance payers, dental insurance payers, vision insurance payers, and/or indemnity insurance payers. The coverage details, for example, may be collected from computer systems of each payer on an as-needed basis (if not already accessed) or on a scheduled basis (e.g., annually or another periodic timeframe when updates are applied to various plans offered by the payer(s)). The provider data 122, in some implementations, includes payer acceptance information, rate information, preferred provider rate information, and address.

In some embodiments, a portion of the data records in the data universe 104 contain de-identified data. The de-identified data may remove information that can be used to link (e.g., "reverse engineer") the data to match the data to a certain individual or small number of individuals. De-identification, in some examples, may include removing patient name, social security number, exact birth date, street address, and/or phone number from records such as the historic claims data 120 and a demographic data portion of the patient data 124.

In some embodiments, the predictive analytics platform 102 derives insights 154 from the data accessed from the data universe 104, for example using machine learning analysis and or other statistic data analysis techniques. The predictive analytics platform 102, for example, may include machine learning classifiers trained using historic data records to identify patterns in the data records of the data universe 104 based upon claims information such as the information supplied in the medical claim information 108, 109. In another example, the predictive analytics platform 102 may derive insights 154 from the data universe 104 through cluster analysis of data records by applying techniques such as, in some examples, centroid-based clustering, density-based clustering, and/or multi-dimensional clustering. The information accessed from the data universe 104 may be arranged in a variety of manners to apply the machine learning analysis and/or cluster analysis such as, in some examples, a convolutional neural network (CNN), deep neural network (DNN), clustering tree, and/or synaptic learning network. The arrangement of data and/or type of learning analysis applied may be based in part upon the type and depth of information accessed, the desired insights to draw from the data, storage limitations, and/or underlying hardware functionality of the predictive analytics platform 102.

The predictive analytics platform 102, in some embodiments, produces complex predictive intelligence 156, (e.g., predictive analytic output) for example by deriving metrics and/or calculating estimates using the derived insights 154. For example, the predictive analytics platform 102, in response to the inquiry 112a regarding a remaining patient deductible, may calculate, from derived insights 154 related to timing of deductible updates in the payer system according as demonstrated by payer data 126, predictive intelligence 156 including a number of days to suspend claim submission to await an update in the deductible amount. In another example, responsive to the revenue inquiry 112b regarding avoiding claim denial, the predictive intelligence 156 may include confirming the procedure codes 114a,114b are ones historically accepted by the payer. In a third example, responsive to the inquiry 112c regarding prior authorization, the predictive intelligence 156 may include, based on an indication from the machine learning analysis 154, that prior authorization is likely needed. In various implementations, the predictive analytics platform 102 may automatically issue a request for authorization from the payer, may automatically notify a third party to request authorization from the payer, and/or may provide a notice to the user of the platform 102 that the prior authorization is required. The notice to the user may include an identification of the third party from which to request this authorization.

In some embodiments, the predictive analytics platform 102 provides the complex predictive intelligence 156 (e.g., predictive analytic output) to the reporting portal 111, for example in the form of clinical and/or financial reports such as a patient report card or provider score card, described below. The complex predictive intelligence 156 may be rendered in a graphical user interface in the form of short textual and/or numerical answers, charts, graphs, interactive spreadsheets, and/or interactive reports, in some examples.

Figure 1B:
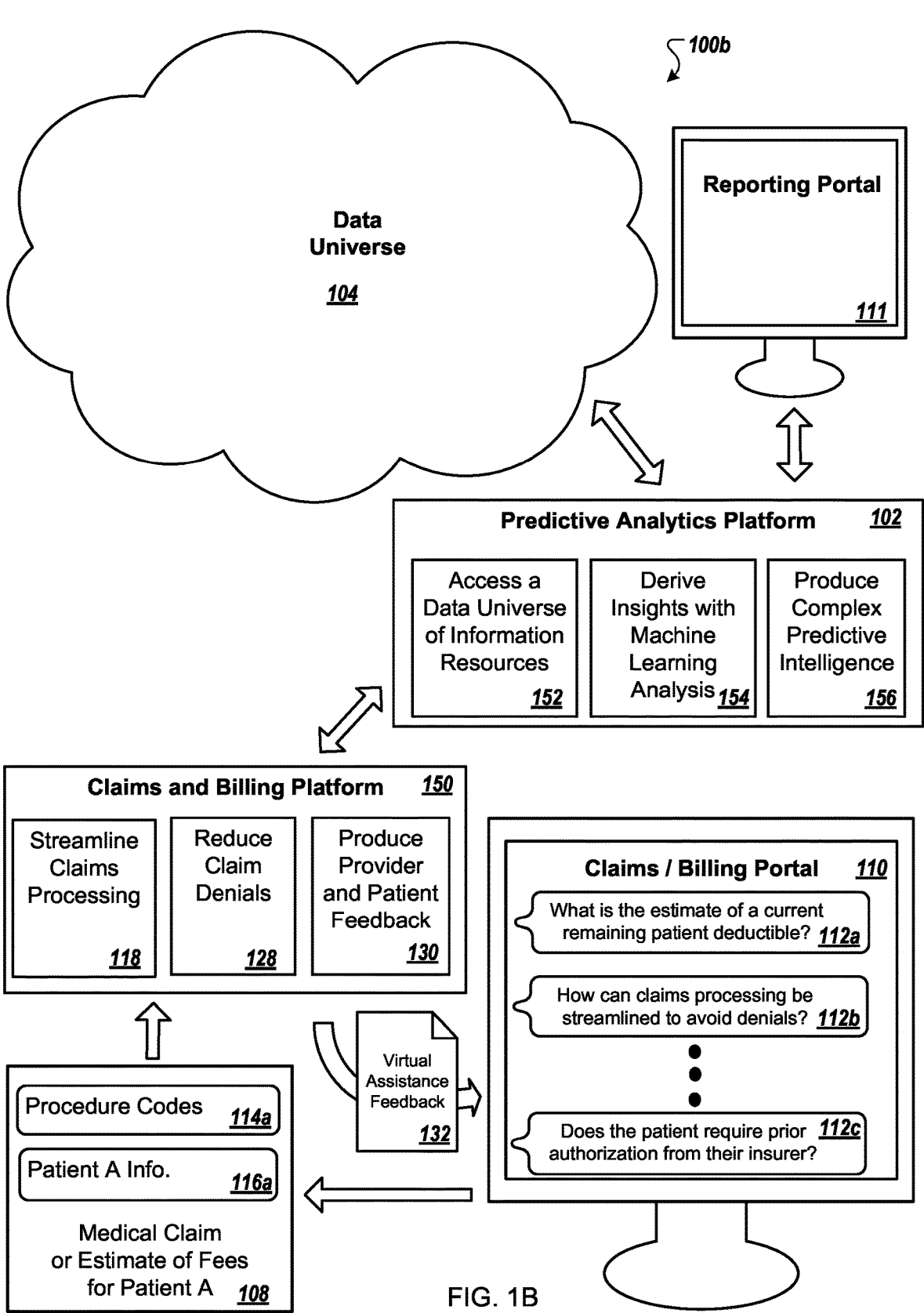
FIG. 1B is a process flow diagram of an example process obtaining complex predictive intelligence from a predictive analytics platform to enhance claims processing as well as patient and payer feedback.

Turning to FIG. 1B, in some implementations, the predictive analytics platform 102 provides the complex predictive intelligence 156 (e.g., predictive analytic output) to a claims and billing platform 150. For example, to streamline claims processing 118, the claims and billing platform 150 may receive automated confirmation of patient information 116a and/or a likelihood of pre-approval requirements for any of the procedure codes 114a. In another example, to reduce claim denials 128, the claims and billing platform may provide the procedure codes 114a to the predictive analytics platform 102 to receive predictive intelligence 156 related to the likelihood of denial based upon the coding applied in the procedure codes 114a and/or other codes or claims information that may be required based upon any of the procedure codes 114a. The predictive intelligence 156, further to this example, may be provided to the claims and billing platform 150 as virtual assistance feedback 132 which is then incorporated into the claims processing at the claims and billing portal 110. In a further example, to produce provider and patient feedback 130, the claims and billing platform 150 may receive predictive intelligence 156 from the predictive analytics platform 102 in the form of financial estimates including non-dollar-amount financial estimates (e.g., estimated deductible level, estimated time to payment, estimated likelihood of payment etc.) and/or comparative analysis metrics (e.g., to peers of a provider). The predictive intelligence (e.g., predictive analytics output) provided to the claims and billing portal 110 and/or the reporting portal 111 may further include identified payers based on subscriber identifiers, deductible information, and/or prior authorization information.

Figure 1C:
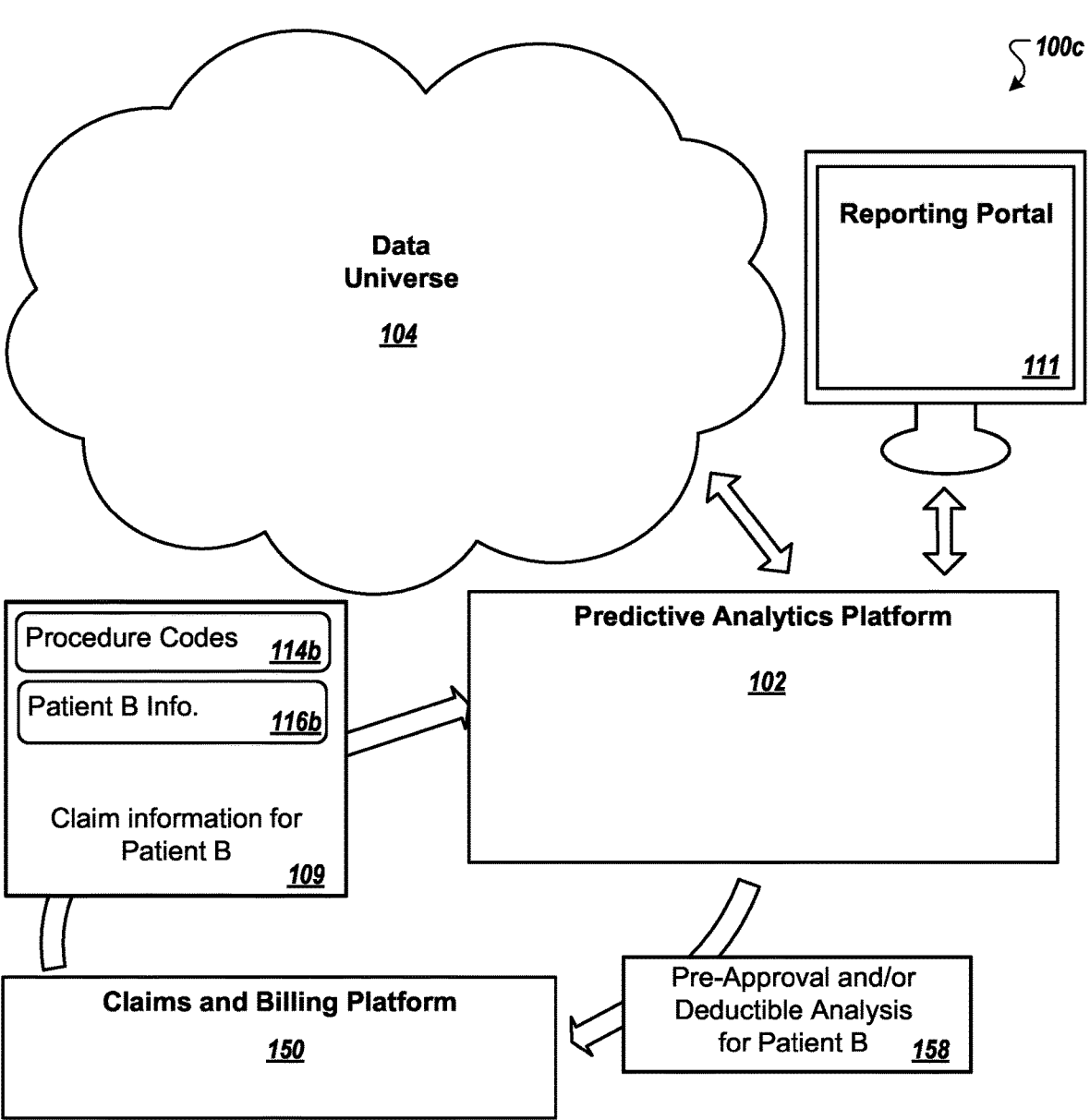
FIG. 1C is a process flow diagram of an example process obtaining complex predictive intelligence from a predictive analytics platform to enhance claims processing as well as patient and payer feedback.

Referring to FIGS. 1B and 1C, examples of systems enabling interaction between the predictive analytics platform and a claims and billing platform are shown (e.g., the systems 100b and 100c). In an implementation, a claims processing agent may interact with the predictive analytics platform 102 via the claims and billing platform 150 and derive predictive intelligence via interactions with the predictive analytics platform 102. Additionally, a patient and/or a provider may interact with the predictive analytics platform 102 to utilize the predictive intelligence and data universe 104 access to generate real-time and interactive patient or provider report cards. The patient report cards may aggregate clinical and financial data.

Claims/billing portal 110, in some embodiments, is designed to interact with the claims and billing platform 150 via input provided by a representative through a graphical user interface. The claims/billing portal 110 may enable a person initiating, inspecting, or otherwise handling a medical billing claim to receive predictive output from and interact with the predictive analytics platform 102. Although shown as two separate portals, in an implementation, the claims and billing portal 110 and the reporting portal 111 may be a single and integrated portal. Additionally, although illustrated in FIG. 1B as a monitor or display screen, the claims and billing portal 110 is not limited to a physical display. Rather, the portal 111 may refer to a physical display, an application enabling access to claims and billing output, the claims and billing data, or combinations thereof.

The claims and billing platform 150, to streamline claims processing 118 and reduce claim denials 128, in one example, may provide virtual assistance feedback 132. The virtual assistance feedback 132, for example, may be responsive to claims or billings inquiries such as, but not limited to, "what is the estimate of a current remaining patient deductible?" 112a, "how can claims processing be streamlined to avoid denials?" 112b, and/or "does the patient require prior authorization from their insurer" 112c. Information discussed herein as being provided at the claims and billing portal 110 in FIG. 1D, may also be provided in various implementations at the reporting portal 111 and may or may not refer to a particular medical claim. In some cases, this information may refer to patient(s), provider(s), payer(s) and/or combinations thereof without particular reference to specific medical claim or claims. The inquiries 112 may include or reference medical claim information 108 such as one or more procedure codes 114a and patient demographic data 116a. As illustrated, the medical claim information 108 presented relates to a medical billing claim or estimate of medical fees regarding a particular patient ("Patient A"). The medical claim information 108 may vary based on the request presented to the claims and billing portal 110. Additionally, in some embodiments, claims information 108 regarding a set of medical claims may be presented to the predictive analytics platform 102, for example for producing payer or patient feedback 130 regarding a financial state.

In some implementations, in addition to or as an alternative to receiving input via the portal 110, the predictive analytics platform 102 receives all or a portion of input through an application programming interface (API) accessed by and/or batch files provided by the source of the input data (e.g., provider or billing service for provider). For example, as shown in FIG. 1C, a representative of a medical provider may interact with the predictive analytics platform 102, for example to obtain pre-approval or deductible analysis 158 regarding a patient. The data, for example, may be provided as medical claim information 109 including procedure codes 114b and patient information 116b (illustrated in FIG. 1C as regarding "Patient B"). In an illustrative example, the portal 111 may include a selectable control in the form of a displayed icon or tab. Activation of this control by the user of the portal 111 may enable the predictive analytics platform 102 to pull data in through the API and/or the batch files.

In some embodiments, for example as illustrated in FIG. 1B and FIG. 1C, the predictive analytics platform 102 applies the claim information 108, 109 in accessing 152 the data universe 104. Data fields contained in the claim information 108, 158, for example, may be used to cross-reference or link with various data records in the data universe 104. The claim information 108, 109 may be obtained, for example, from a claims processing system (e.g., a newly generated claim, in-process claim, or a claim recently submitted for reimbursement). In another example, the claim information 108, 109 may represent data collected prior to claim generation, such as a portion of a patient's electronic chart.

The claim information 108, 109, in some implementations, is obtained from an electronic patient charting file, e.g., an electronic patient care record (ePCR) populated in real-time by emergency medical services (EMS) during an emergency medical event. For example, a mobile device may include an application (e.g., a charting application 832 of FIG. 8C) configured to populate the ePCR via an EMS charting system 840 as shown in FIG. 8C. The EMS charting system 840 may be part of a shared cloud-based platform encompassing both a patient charting service (e.g., the EMS charting system 840) and the predictive analytics platform 102 and providing these as Software-as-a-Service (SaaS). The shared cloud-based platform may also include services such as computer-aided dispatch (e.g., the CAD system 834 of FIG. 8C) and medical transport dispatch and scheduling. Alternatively, servers from separate providers or clouds may service the patient charting service, and the predictive analytics platform 102 and these servers may communicatively couple via a long-range network such as the Internet and/or via an information exchange service 836 as shown in FIG. 8C.

In some embodiments, the claim information 108, 109 originates from an electronic health record (EHR) generated by a physician, hospital caregiver, or other non-EMS service provider. The EHR may be stored on-premises and/or in a cloud database (e.g., a medical record repository 105), and the predictive analytics platform may access the EHR via a communicative coupling (e.g., Internet, cellular network, information exchange service 836 of FIG. 8C, etc.) with the appropriate database.

The procedure codes 114a,b of the claim information 108, 109, in some implementations, includes Current Procedural Terminology (CPT®) codes and/or Healthcare Common Procedure Coding System (HCPCS) codes. Rather than or in addition to procedure codes 114a,b, in some implementations, the claim information 108, 109 includes reference codes or identifiers not included in the CPT® and/or HCPCS listings such as, in some examples, medical equipment and/or supply identifiers, prosthetics and/or orthotics devices and supplies identifiers, home health services identifiers, and/or prescription drug identifiers. The patient demographic data 116a,b, in some examples, may include the patient's name, identification number, address, social security number, height, weight, gender, date of birth, and/or medical history.

FIG. 1D is a block diagram of an example system 160 including the predictive analytics platform 102. In some implementations, the predictive analytics platform 102 is in communication with the claims and billing platform 150 via a network 170. As illustrated, a set of engines of the claims and billing platform 150 access predictive analytics supplied by a set of machine learning classifiers of the predictive analytics platform 102.

In some implementations, the claims and billing platform 150 includes a set of engines (e.g., programs, algorithms, or applications) for performing, alone or in combination, claims and billing functions on behalf of clients, such as service providers. The engines may include software and/or hardware logic for performing the operations of each program, algorithm, or application. For example, in some embodiments, one or more engines include at least a portion of its functionality as hardware logic encoded into a programmable logic chip or reprogrammable processor. In some embodiments, at least portions of one or more engines perform their functions through executing software on processing circuitry, such as a server or multi-processor cloud computing environment.

Each of the engines of the claims and billing platform 150 may derive predictive analytics through calls to the predictive analytics platform 102. The predictive analytics platform 102, in some implementations, includes a set of machine learning classifiers each trained to perform predictive analytics on behalf of the claims and billing platform 150. The machine learning classifiers, for example, may be trained using historic data collected, in part, via the claims and billing platform 150. Further, the machine learning classifiers may be trained using additional information, such as data accessed from third party systems such as service providers, payers, and clearinghouses.

In some implementations, the engines of the claims and billing platform 150 include a claims processing engine 162 managing automated and/or semi-automated claims preparation. The claims processing engine 162, for example, may obtain an electronic medical record including some patient information and procedure codes related to a medical intervention, format the electronic medical record for submission as a medical claim, and analyze the claim information of the medical claim for missing and/or inconsistent information. The electronic medical record, in some examples, can include an electronic patient charting file such as an electronic patient care record (ePCR) or an electronic health record (EHR).

The claims processing engine 162, in some embodiments, provides medical billing codes to the predictive analytics platform 102 for analysis. For example, the claims processing engine 162 may provide procedure codes for analysis by one or more likelihood of pre-approval requirement by payer classifier(s) 172 of the predictive analytics platform 102 to determine if prior authorization may be required for any of the provided billing codes. The likelihood of pre-approval requirement by payer classifier(s) 172, for example, may be trained using historical claims data, service request data, and/or payer data to anticipate whether certain codes typically correspond to pre-approval requirements (or past denials) based on a given payer.

In another example, the claims processing engine 162 may provide patient information to the predictive analytics platform 102 for analysis using one or more likelihood of patient record match classifier(s) 178. The patient record match classifier(s) 178, for example, may match demographic information acquired during patient intake and match the demographic information to a patient record. Partial information, misspellings, and/or old information may be corrected by the predictive analytics platform 102, for example, and updated by the claims and billing platform 150. Further, the predictive analytics platform 102 may provide the claims and billing platform 150 with additional information, for example to fill in the patient data gaps for claims processing.

In some embodiments, the claims processing engine 162 provides claims data to the predictive analytics platform 102, such as procedure codes, for analysis regarding claims data entry requirements and/or likelihood of approval of a medical claim. For example, the claims processing engine 162 may provide claims data entered into a medical claims form (automatically and/or by a claims processing agent) for analysis by one or more required claims fields by player classifier(s) 180 to ensure that information entered into the medical claim form is complete as per requirements by a particular payer. In another example, the claims processing engine 162 may provide procedure codes to one or more likelihood of procedure code approval by payer classifiers 182 to ensure that the procedure codes entered match codes previously accepted by a particular payer. In medical coding, in many circumstances, two or more procedure codes may be applied to a same type of medical service, equipment, or prescription. The likelihood of procedure code approval by payer classifier(s) 182, for example, may provide an alternate option if a given payer is more likely to approve the claim with a related procedure code rather than the originally entered procedure code.

In some embodiments, a services schedule engine 164 of the claims and billing platform 150 provides procedure codes to the predictive analytics platform to obtain a cost estimate for medical equipment, services, and/or prescriptions. For example, the services scheduling engine 162 may provide procedure codes to the predictive analytics platform 102 to determine an estimated cost of procedures based on procedure codes using one or more estimated cost per procedure code classifier(s) 174. The estimated cost per procedure code classifier(s) 174, for example, may be trained using historic remittance data and/or claims data to identify costs typically associated with various procedures. Further, the services scheduling engine 162 may provide payer information to the predictive analytics platform 102 to determine an estimated deductible updating schedule using one or more deductible updating pattern by payer classifiers 176 in an effort to determine a current deductible remaining to the patient. In this manner, for example, the services scheduling engine 164 may provide the patient with a better estimate of out-of-pocket cost for a scheduled procedure. Additionally, the services scheduling engine 164 may provide a provider with an optimized and automated deductible management service that enables the provider to submit bills based on a predicted deductible payment or exhaustion by the patient.

Figure 1E:
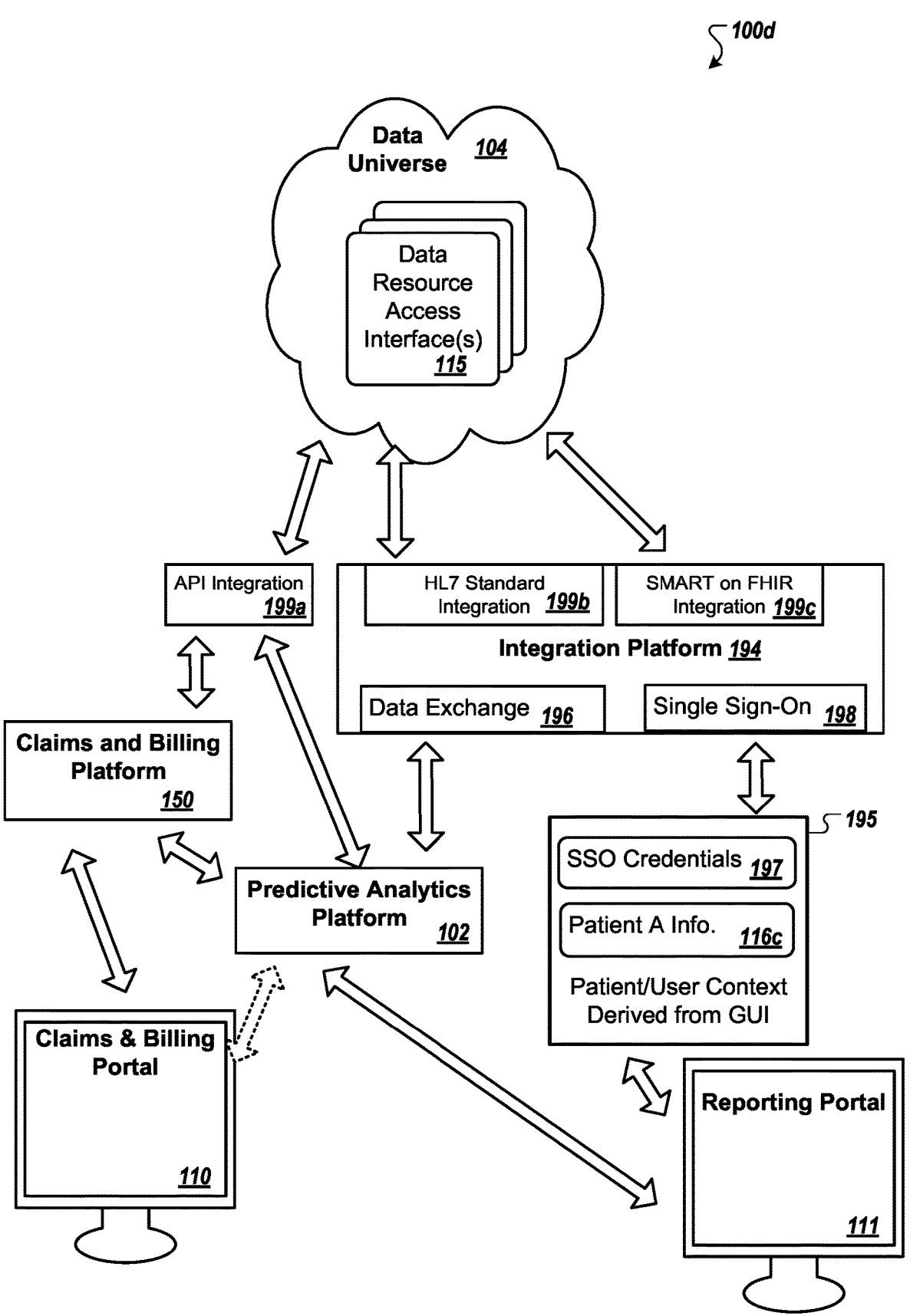
FIG. 1E is a process flow diagram of an example integration architecture for a predictive analytics platform.

Turning to FIG. 1E, an example of a communications architecture 100d including the predictive analytics platform 102, the data universe 104, the claims and billing platform 150, the reporting portal 111, and the claims and billing portal 110 is shown. In this example, the communications structure includes a set of data communications integrations 199 and an integration platform 194.

The data resource access interface 115 may be a software interface to one or more of the data universe resources shown, for example, in FIG. 1A. As such, the access interface 115 is a networked storage access interface that may enable a user and/or a computing system outside of the data universe 104 to interact with the data universe 104 (e.g., provide data to, store data in, access data in, retrieve data from, etc.). As an example, the data resource access interface 115 may be an electronic medical record interface configured to receive information from the user including patient health care information and demographics. As another example, the data resource access interface 115 may be a medical claims and billing interface configured to receive information from the user relating to a medical claim or medical bill. The user of the data resource access interface 115 may be a patient, a provider, a payer, a representative of the patient, provider, or payer, or a combination thereof. Thus, the data resource access interface 115 enables population of data in the data universe 104 as well as access to the data to view, modify, delete, create reports, create files, etc. The integration platform 194 may enable a user of the data resource access interface 115 to interact with predictive analytic output provided to the reporting portal 111 and/or to the claims and billing portal 110 via the data resource access interface 115.

Although shown outside of the data universe 104, in some implementations, the data resource access interface 115 may include the claims and billing portal platform 150 and the claims and billing portal 110. In such an implementation, the integration platform 194 may enable a user of the claims and billing platform 150 and portal 110 to interact with the predictive analytic output provided to the reporting portal 111.

In some implementations, the predictive analytics platform 102 and/or the claims and billing platform 150 are configured to communicate with the data universe 104 using an application programming interface (API) integration 199a. The API integration 199a, in some examples, may allow claim submission software applications, statistical analysis and reporting software applications, and/or billing and invoicing software applications to submit requests for information and/or data uploads to the data universe 104 through the use of a set of standardized API interfaces. Further, as illustrated, the claims and billing platform 150 may include a direct connection to at least a portion of the data universe 104 (e.g., medical records 105 related to patients of a particular user of the claims and billing platform 150).

In some implementations, an integration platform 194 may be configured to exchange data between the various entities of the data universe 104 and the predictive analytics platform 102 using a single standard data format. The single standard data format may be a common data format recognized or used by one or more entities of the data universe 104 and the predictive analytics platform 102. The integration platform 194 may translate or convert data that is stored in, received from, or provided to the data universe 104 and/or the predictive analytics platform 102 in a format other than the single standard data format to the single standard data format. For example, the integration platform 194 may convert a comma separated values (CSV) format, an extensible markup language (XML) or other text file format, or JavaScript® Object Notation (JSON) formatted files to the communication standard. The integration platform 194 may provide the predictive analytics platform 102 and/or the reporting portal 111 with access to the data universe 104 by translating communications from users connecting to the integration platform 194 into one or more communications standards recognized and/or utilized by the data universe 104. The communications standards may include, in some examples, but not limited to, a Health Level Seven (HL7®) standard provided by an HL7® standard integration 199b and/or a Substitutable Medical Applications and Reusable Technologies (SMART®) on Fast Healthcare Interoperability Resources (FHIR®) standard provided by a SMART® on FHIR® integration 199c. Optionally, the integration platform 194 may provide the claims and billing portal 110 with access to the data universe 104. The integration platform 194 may be configured to recognize a variety of communications standards adopted by users of the data universe 104 such as, in some examples, HL7® version 2.x, HL7® version 3, Clinical Document Architecture (CDA), Continuity of Care Document (CCD), Fast Healthcare Interoperability Resources (FHIR®), and/or file transfer protocol (FTP). As such, the integration platform 194 may be considered to be an aggregator that aggregates communications presented in a variety of forms, such as a variety of HL7® standard formats, into a single format (e.g., HL7® version 3, FHIR®) or a set of formats (e.g., one version of the HL7® standard plus SMART® on FHIR®). Users (e.g., of the predictive analytics platform 102 and/or the reporting portal 111) may communicate with the integration platform 194 via a data exchange interface 196 and/or a single sign-on (SSO) interface 198.

In some implementations, the data exchange interface 196 provides a set of APIs for users to communicate via one of a collection of supported standards, such as the various standards listed above. Similar to the API integration 188a, the data exchange interface 196 may allow users to submit requests for information and/or data uploads to the data universe 104 through the use of a set of standardized API interfaces.

In some implementations, a user, such as a user of the reporting portal 111, accesses the single sign-on interface 198 using a set of SSO credentials 197. The SSO credentials 197, for example, may include a username, password, and/or other authentication data (e.g., biometric data, pin code, email address, etc.). The SSO interface 198, for example, may provide the user of the reporting portal 111 with access to features of the predictive analytics platform 102, the claims and platform 150, and/or the data universe 104 through authenticating the user with the SSO credentials

197. The SSO interface 198, for example, may supply an authentication token to the reporting portal 111 for use during a session with the predictive analytics platform 102, claims and billing platform 150, and/or data universe 104.

The SSO credentials 197, in some implementations, are provided as part of a set of patient and/or user context information 195 derived via a graphical user interface of the reporting portal 111. For example, information entered by the user at the reporting portal 111 may be collected as context for launching an appropriate interface with the predictive analytics platform 102 and/or the claims and billing platform 150. For example, if the user has been reviewing or entering information related to Patient A, the Patient A information 116a may be provided to the integration platform 194 for launching a context-aware session with the predictive analytics platform 102, the claims and billing platform 150, and/or the data universe 104. Further, the context information 195 may be used to initially populate the user session with information anticipated to be of interest to the user (e.g., information regarding Patient A gathered from the data universe 104). In this manner, the context information 195 may form an initial query or request for information from the data universe 104.

In some implementations, the HL7® standard integration 199b is used for connecting to the data universe 104 via a web application, while the SMART® on FHIR® integration 199c is used when accessing the data universe 104 via a portal (e.g., using a browser or uniform resource identifier (URI)-based connection, such as a uniform resource locator (URL)-based connection).

Figure 1F:
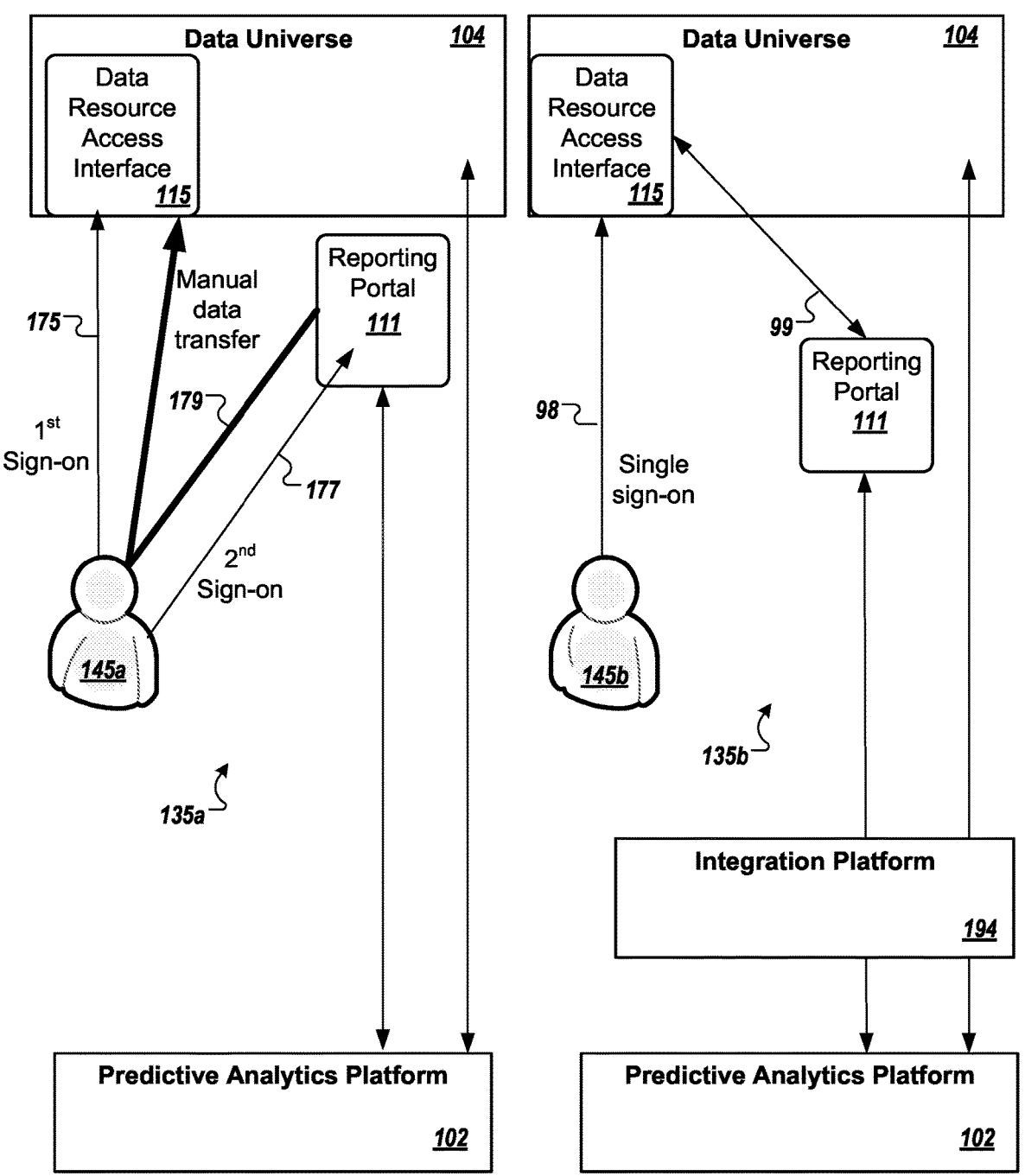
FIGS. 1F and 1G illustrate examples of single sign-on procedures for use of predictive analytic output.
Figure 1G:
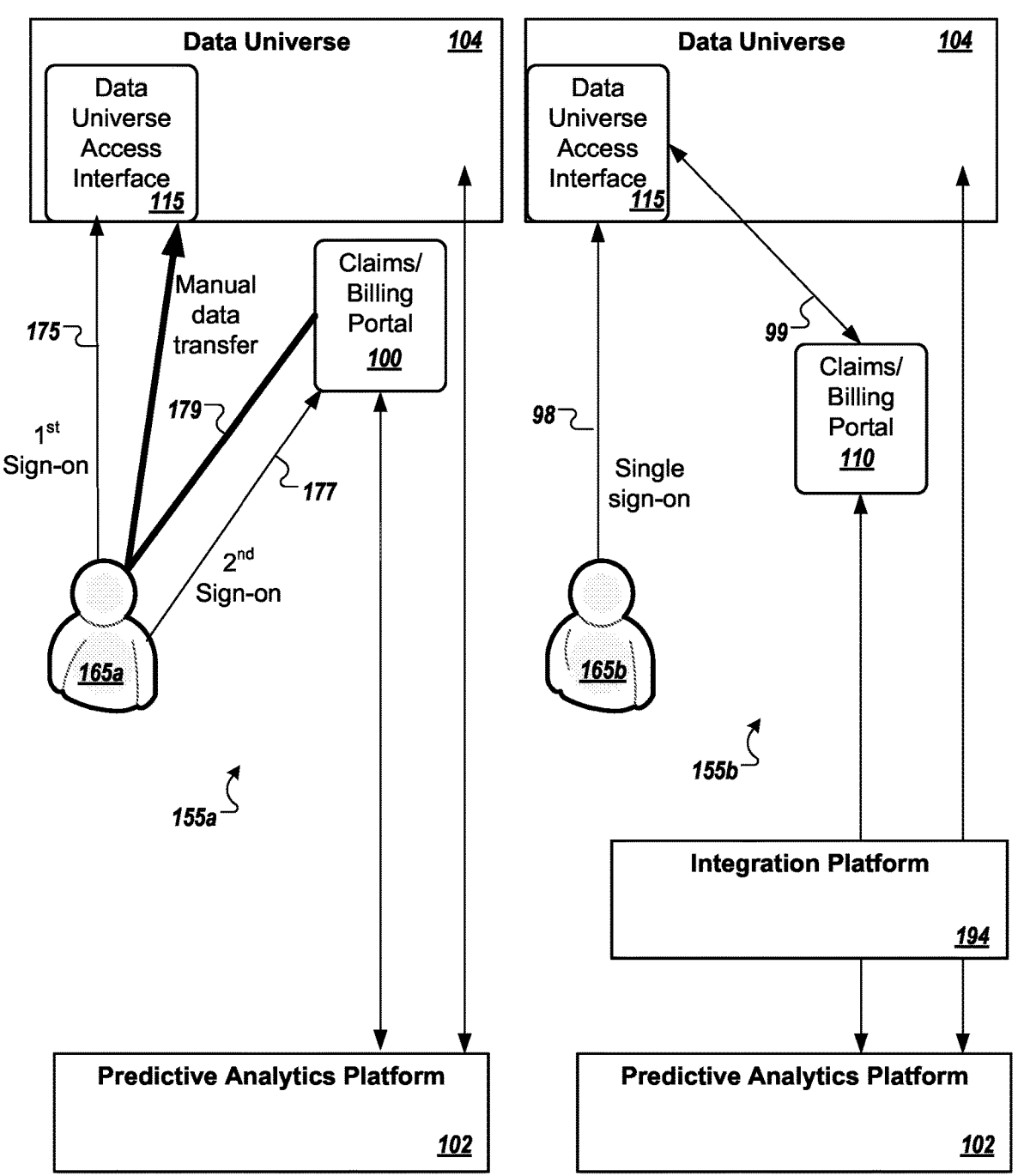

FIG. 1F and FIG. 1G illustrate various sign-on configurations 135 for the predictive analytics platform 102. As illustrated in FIG. 1F, in a configuration 135a, without the integration platform 194, a user 145a of the reporting portal 111 must sign-on to both the data resource access interface 115 and the reporting portal 111. The data resource access interface 115 and the reporting portal 111 are separate from one another. Therefore, in order to transport information between the reporting portal 111 and the data resource access interface 105 without the integration platform 194, the user 135a manually transfers information from the reporting portal 111 to the data resource access interface 115 or vice-versa.

Similarly, in FIG. 1G, the configuration 155a excludes the integration platform 194 and the configuration 155b includes the integration platform 194. Without the integration platform 194, a user 165a of the data resource access interface 115 must sign-on (e.g., log in to a system, provide credentials, implement authorization and/or authentication procedures, etc.) to both the data resource access interface 115 (e.g., via a first sign-on 175) and the claims and billing portal 110 (e.g., via a second sign-on 177). The data resource access interface 115 and the claims and billing portal 110 are separate from one another. Therefore, in order to transport information between the two applications without the integration platform 194, the user 165a manually transfers 179 information from the claims and billing portal 110 to the data resource access interface 115 or vice-versa.

However, with the integration platform 194, and as shown for example in configuration 135b of FIG. 1F and configuration 155b of FIG. 1G, the data resource access interface 115 may be integrated (e.g., based on an integration and interoperability standard such as for example but not limited to the SMART® on FHIR® standard) and only a single sign-on is required for the user 145b or 165b. In such a configuration, the data resource access interface 115 may provide the SSO interface 198. With the integration, the predictive analytics output from the predictive analytics platform 102 is accessible directly from the data resource access interface 115.

For example, the data resource access interface 115 may be an access application for an electronic medical record stored in the medical records database 105. The user 145*b* or the user 165*b* may sign into this portal to interact with the electronic medical record. With the integration, the predictive analytic output provided to the reporting portal 111 and/or the claims and billing portal 110 may be provided at the data resource access interface 115 during the application's workflow. For example, the electronic medical record application may generate HL7® standard messages that are delivered via the integration platform 194 to the predictive analytics platform 102. In response to these messages, the predictive analytics platform 102 may provide an analytic output that is returned directly to the data resource access interface 115 without any disruption in the user's workflow and without any manual transfer operations. Thus, the integration platform 194 may enable access to the predictive analytic output from the predictive analytics platform 102 from the data resource access interface 115.

Figure 2:
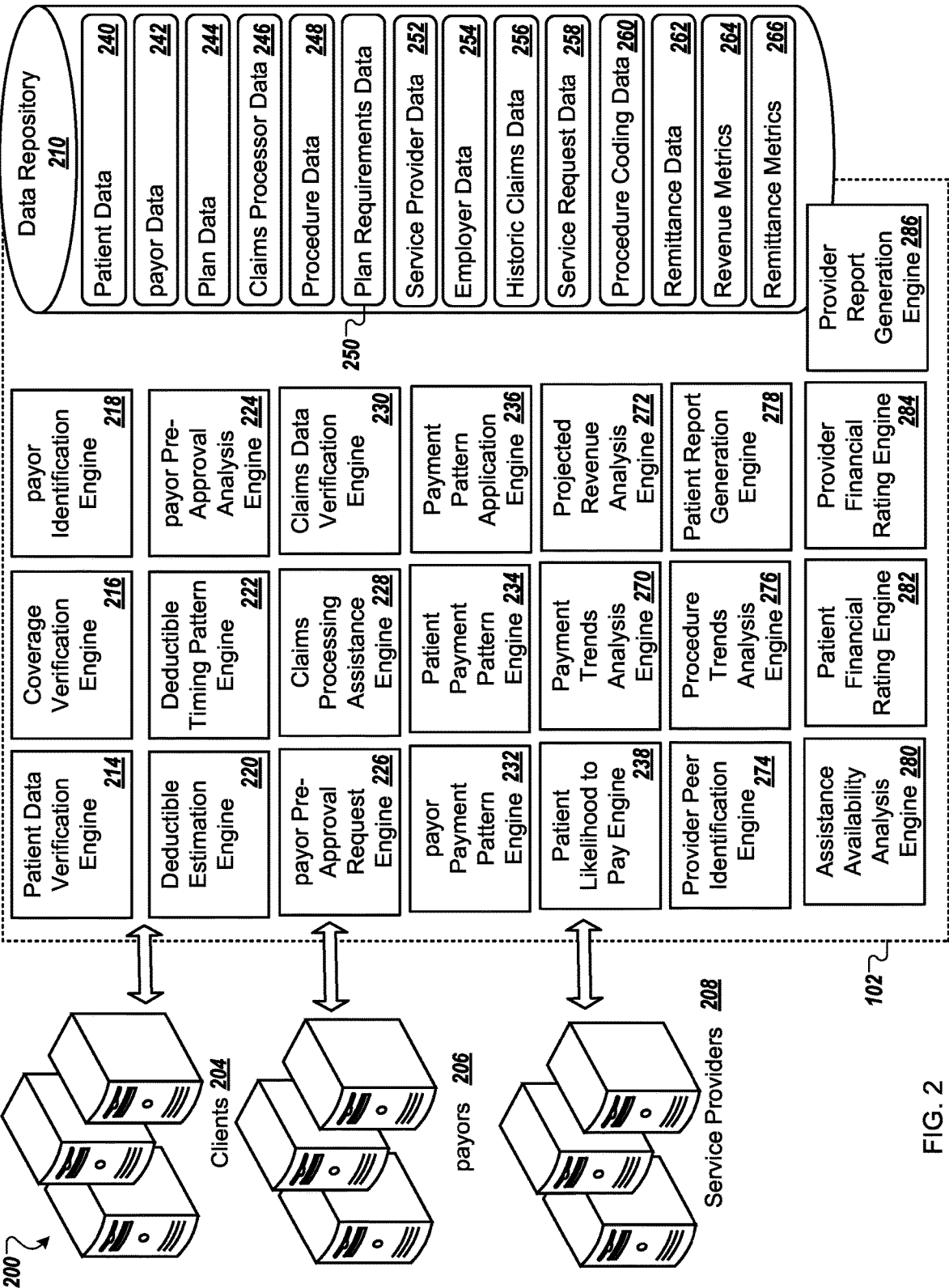
FIG. 2 is a block diagram of an example system and environment for providing predictive intelligence in a medical services environment.

FIG. 2 is a block diagram of an example system including the predictive analytics platform 102 and environment 200 for performing machine learning analysis on portions of a data universe of information resources gathered and/or networked by the predictive analytics platform 102 (e.g., represented by a data repository 210) to produce complex predictive intelligence. The predictive analytics platform 102, for example, may gather and/or network the various information sources, in some examples, from one or more payers 206 and/or service providers 208. The predictive analytics platform 102 may generate, through analyzing the gathered and/or networked information using machine learning classifiers and/or other clustering and pattern identification algorithms, complex predictive intelligence for a set of clients 204. The clients 204 may access the predictive analytics platform 102 via a networked connection. For example, the clients may access the predictive analytics platform 102 through the claims and billing portal 110 described in relation to FIG. 1.

In some implementations, the predictive analytics platform 102 includes a set of engines (e.g., programs, algorithms, or applications) for performing, alone or in combination, predictive analytics on behalf of the clients 204. The engines may include software and/or hardware logic for performing the operations of each program, algorithm, or application. For example, in some embodiments, one or more engines include at least a portion of its functionality as hardware logic encoded into a programmable logic chip or reprogrammable processor. In some embodiments, at least portions of one or more engines perform their functions through executing software on processing circuitry, such as a server or multi-processor cloud computing environment. Each engine may access various sets of data as illustrated in the data repository 210. Although represented as a single repository, the data repository 210 represents a networked or otherwise linked collection of data sources including, in some examples, one or more databases, one or more data warehouses, one or more neural data networks, one or more synaptic data networks, and/or other arrangements of interconnected and stored data. Further, various engines of the predictive analytics platform 102, in some embodiments, are designed to query or otherwise access information in real-time from one or more external data sources.

The predictive analytics platform 102, in some implementations, includes a patient data verification engine 214 for verifying and/or supplementing patient information with demographic information or other patient record information obtained from an external source. The patient data verification engine 214, for example, may compare external information with patient data 240 maintained by the medical provider and update or supplement the information where appropriate. The patient data verification engine 214, for example, may execute the likelihood of patient record match classifier(s) 178 of FIG. 1B.

In some implementations, the predictive analytics platform 102 includes a coverage verification engine 216 configured to automatically submit patient information to a payer system to confirm active coverage of the patient by the payer. The coverage verification engine 216, for example, may be invoked where the coverage for the patient is uncertain or where the most recent coverage verification for the patient was obtained outside a threshold window of time such as, in some examples, over one month, over three months, or longer than six months. To verify coverage, in some embodiments, the coverage verification engine 216 automatically submits identifying demographic information such as, in some examples, name, date of birth, social security number, patient residence, work, or billing address, insurance subscriber number, and/or insurance plan member number to each payer system through an application programming interface (API) or other automated communication means to confirm status of coverage, the goal being to receive a response from at least one payer system confirming active coverage and, thus, positively identifying the payer as a potential medical claim recipient for the service. Some payers will additionally supply patient record information in response to identifying active coverage and/or upon subsequent request, thereby allowing the medical provider to supplement patient information in local records and/or update outdated patient information within local records. In some embodiments, the coverage verification engine 216 coordinates with the demographic verification engine 214 to update and/or supplement demographic information related to a patient.

In some implementations, the predictive analytics platform 102 includes a payer identification engine 218 for automatically matching one or more payers with a patient based on demographic and/or other known information regarding the patient. The payers, for example, may include primary insurance providers, Medicare, and Medicaid. Further, the payers may include liability payers such as automotive liability insurance, homeowner insurance, worker compensation insurance, and/or business liability insurance. In some embodiments, a call to the payer identification engine 218 includes an indication of type of insurance to identify (e.g., primary, liability, all, etc.). The payer identification engine 218 may analyze patient data 240 and payer data 242 to determine trends in payer coverage per demographic grouping (e.g., geographic region, age group, etc.). Further, the payer identification engine 218, in some embodiments, analyzes employer data 254 and/or guarantor data 246 to identify trends in employer-provided payer coverage per demographic grouping (e.g., employees of a national organization residing in a particular state or a particular region of the United States). The payer identification engine 218 may return identification of one or more payers. In some embodiments, the payer identification engine 218 further includes a default set of payers (e.g., the top N payers nationally) to suggest as likely payers covering the patient. In some implementations, the payer identification engine 218 automatically confirms coverage by calling the coverage verification engine 216 for each likely payer candidate. Upon confirming, in some implementations, the response from a particular payer may identify one or more secondary payers. For example, when verifying coverage of a primary payer, the primary payer may confirm active coverage and further identify one or more secondary insurance sources on record as being available to the patient.

In some implementations, the predictive analytics platform 102 includes a deductible estimation engine 220 for calculating a current dollar amount remaining in a patient's deductible for a particular payer. For example, the patient may have multiple outstanding claims for medical services, prescriptions, and/or equipment that may reduce a deductible level reported by the payer. As another example, various patient co-payment amounts may change a deductible amount and/or time to deductible exhaustion. The deductible estimation engine 220 may gather information regarding pending claims and/or invoices to deduct the outstanding amount from the remaining patient deductible.

The predictive analytics platform 102, in some implementations, includes a deductible timing pattern engine 222 for anticipating a deductible updating schedule based upon a payer corresponding to the patient. For example, when submitting a claim to a payer, the service provider may first determine a dollar amount to deduct based upon patient cost responsibility. However, the information provided by a particular payer may not be up-to-date. Further, certain payers may charge for acquiring this information. By anticipating a date or number of days until deductible updating, for example, a claim may be placed on hold intelligently to limit the delay of submission while ensuring the most reliable information regarding deductible amount is available to the claims processor (e.g., the claims processing platform 150 of FIGS. 1B, 1C, 1D, 1E, and 1G). The deductible timing pattern engine 222, for example, may execute the deductible updating pattern by payer classifier(s) 176 of FIG. 1D to anticipate the deductible updating schedule of the payer.

In combination, the deductible estimation engine 220 and the deductible timing pattern engine 222 enable real-time deductible monitoring by the predictive analytics platform 102. The predictive analytics platform 102 may provide information based on this monitoring to other services including the medical claims processing service, for example provided in part by the claims processing engine 162 of the claims and billing platform 150 of FIG. 1B. This real-time deductible monitoring provides an advantage over static and fixed interval deductible monitoring where a system is programmed to check a deductible status on a fixed and predetermined schedule (e.g., every 3-14 days). Additionally, the predictive analytics platform 102 may harness payer pattern information and/or geographical customization information to predict and forecast deductible estimates and/or timing based on data from a larger number of entities than just the patient associated with the deductible. Leveraging the larger dataset of the data universe 104 improves the accuracy of these predictions and forecasts.

The predictive analytics platform 102, in some implementations, includes a payer pre-approval analysis engine 224 for determining likelihood of the payer requiring pre-approval for one or more services and/or products recommended by or scheduled for performance by a medical provider. The payer pre-approval analysis engine, for example, may analyze, for example using the payer payment pattern engine 232, trends in historic claims data 256 corresponding to a payer of the patient's coverage to identify claims rejections related to one or more products and/or services identified to the payer pre-approval analysis engine

224. For example, if a claim for a product or service is commonly rejected, this may be due to the product or service only being covered when pre-approval has been obtained. Further, the payer pre-approval analysis engine 224 may analyze the claims data 256 (e.g., via the payer payment pattern engine) to identify indicators of pre-approval within the claims data records 256 corresponding to approved (e.g., reimbursed) claims by the payer. In some embodiments, the payer pre-approval analysis engine 224 analyzes service request data 258 to identify historic requests for authorization. The payer pre-approval analysis engine 224, for example, may apply pattern analysis to the identified claims data records and/or service request data records. The pattern analysis, in some examples, may be performed using machine learning analysis, cluster analysis, and/or statistical data analysis to identify data patterns within the accessed records. The payer pre-approval analysis engine 224 may return an indication of whether there is evidence that authorization is required (e.g., yes or no). The payer pre-approval analysis engine 224 may return, instead of or in addition to a positive or negative answer, a confidence level and/or confidence rating regarding this assessment.

The predictive analytics platform 102, in some implementations, includes a payer pre-approval request engine 226 for automatically submitting a pre-authorization request in relation to a scheduled service or recommended product. The payer pre-approval request engine 226, for example, may receive indication of a payer, a billing code, and a patient, for example a payer identifier and a patient identifier. Further, the payer pre-approval request engine 226 may receive identification of a payer plan. The payer pre-approval request engine 226 may prepare a pre-authorization request based on this information and, using the payer identification, determine automated contact information, such as an API, for submitting the pre-approval request. The payer pre-approval request engine 226 may also receive indication of a requestor such that, after receiving a response from the payer system, the payer pre-approval request engine 226 may automatically alert the requestor of the outcome of the request (e.g., approved, denied). In various implementations, the platform 102 may automatically issue a request for authorization from the payer, may automatically notify a third party to request authorization from the payer, or may provide a notice to the user of the platform 102 that the prior authorization is required. The notice to the user may include an identification of the third party to request this authorization.

In some implementations, the predictive analytics platform 102 includes a claims processing assistance engine 228 for providing assistance to a claims agent in preparing a medical claim for submission. The claims processing assistance engine 228, for example, may provide the virtual assistance feedback 132, as described in relation to FIG. 1B. In another example, the claims processing assistance engine 228 may execute the required claims fields by payer classifier(s) 180 and/or the likelihood of procedure code approval by payer classifier(s) 182 described in relation to FIG. 1D.

The predictive analytics platform 102, in some implementations, includes a claims data verification engine 230 for verifying completeness and accuracy of claims data entered into a claims form. For example, the claims data verification engine 230 may execute the likelihood of pre-approval requirement by payer classifier(s) 172 to determine whether certain medical codes are associated with a pre-authorization requirement in view of the payer, as described in relation to FIG. 1D.

The predictive analytics platform 102, in some implementations, includes a payer payment pattern engine 232 configured to analyze historic reimbursement data for a payer to identify trends or patterns in amounts, timing, and/or denials. The payer payment pattern engine 232, for example, may access payer data 242, plan data 244, and/or historic claims data 256. Further, the payer payment pattern engine 232, in some embodiments, accesses patient data 240 to identify trends across groups of insured individuals, such as regional trends. The pattern analysis, in some examples, may be performed using machine learning analysis, cluster analysis, and/or statistical data analysis to identify data patterns within the accessed records. The payer payment pattern engine 232 may generate payment pattern data for use by the predictive analytics platform 102 and/or the claims and billing platform 150.

In some implementations, the predictive analytics platform 102 includes a patient payment pattern engine 234 to identify patient payment trends from historic claims (e.g., claims data 256 cross referenced with patient data 240) based upon a patient medical debt score or rating (e.g., as generated by a patient financial rating engine 282). In some embodiments, the patient payment pattern engine 234 further uses patient demographic data or other information to refine analysis of similar patients. The demographic data, in some examples, can include geographic region, age range, gender, employment status, and/or income level. The patient payment pattern engine 234 identifies patient payment outcomes related to patients similar to the payer at least in medical credit score or rating. Pattern analysis may be applied to the identified claims data records. The pattern analysis, in some examples, may be performed using machine learning analysis, cluster analysis, and/or statistical data analysis to identify data patterns within the accessed records. The patient payment pattern engine 234 may generate patient payment pattern data for use by the predictive analytics platform 102 and/or the claims and billing platform 150.

In some implementations, the predictive analytics platform 102 includes a payment pattern application engine 236 configured to apply payer payment patterns produced by the payer payment pattern engine 232 and/or patient payer patterns produced by the patient payment pattern engine 234 to calculate payment estimations. Further, in some embodiments, the payment pattern application engine 236 determines a confidence level or rating associated with the payment estimate. The confidence level or rating, in some examples, can include a percentage confidence, a ranked confidence (e.g., on a scale of 1 to X), and/or a ratings confidence (e.g., low, medium, high).

The predictive analytics platform 102, in some implementations, includes a patient likelihood to pay analysis engine 238 for determining whether a remaining balance is likely to be repaid by the patient. The patient likelihood to pay analysis engine 238, in some embodiments, requests a patient financial clearance or risk analysis related to medical debt from a credit reporting agency specializing in healthcare reimbursement data, such as TransUnion LLC of Chicago, Illinois or Experian Health by Experian Information Solutions, Inc. of Costa Mesa, CA. Further, the predictive analytics platform 102, in circumstances where a responsible party holds the payer coverage (e.g., parent, spouse, guardian, etc.), may identify information regarding the responsible party and request the patient financial clearance or risk analysis related to medical debt regarding the responsible party. In some implementations, the patient likelihood to pay analysis engine 238 analyzes historic patient payment trends identified by the patient payment pattern engine 234. The predictive analytics platform 102 may determine a likelihood of the remaining balance being repaid by the patient, for example, based on the patient financial clearance or risk analysis and, in some embodiments, the historic payment trends.

The predictive analytics platform 102, in some implementations, includes a payment trends analysis engine 270 configured to analyze remittance received from payers and/or patients to identify patterns within the payments. The patterns, in some examples, may include a length of time between claim submission and reimbursement, a relative amount paid compared to amount billed, patterns of payer rejections, and patterns of claims re-filings directed to other sources of payments, such as liability payers. Further, the patterns may be broken down into subsets, such as billing code categories, payer types (e.g., liability, primary insurance, federal medical coverage programs, etc.), and/or locations (e.g., for a service provider with multiple physical locations). In some embodiments, the payment trends analysis engine 270 applies machine learning analysis, cluster analysis, and/or statistical data analysis to the remittance data 262 to identify data patterns within the accessed records. For example, the payment trends analysis engine 270 may include different machine learning classifiers trained to identify patterns related to the various sets and subsets of payment types. The machine learning classifiers, for example, may be trained using de-identified data collected over a period of time (e.g., at least 3 months, from 3 to 6 months, up to 1 year, 2 years, etc.). The scope of the training data, for example, may depend upon an amount of data available related to the different variables (e.g., an amount of data per payer, an amount of data per service type, etc.). The payment trends analysis engine 270 may return one or more sets of data patterns for analysis, for example by a projected revenue analysis engine 272.

In some implementations, the predictive analytics platform 102 includes a projected revenue analysis engine 272 configured to analyze historical payment patterns, for example obtained from the payment trends analysis engine 270, in view of recent claims to estimate revenue metrics. The revenue metrics, in some examples, may include remittance by payer, remittance by upcoming revenue cycle, remittance by service type (e.g., billing codes category), and/or remittance by location. The revenue metrics may be refined, in another example, to provide more detailed metrics such as, in some examples, remittance by payer by location and/or remittance by service type by revenue cycle. The metrics derived by the projected revenue analysis engine 272, in some embodiments, depend upon content requested by an end user (e.g., representative of a medical provider) for organization in a spreadsheet, a table, or a report. In some embodiments, the metrics derived by the projected revenue analysis engine 272 depend in part on a type of end user. For example, an emergency medical transportation service provider may desire different metrics than a surgical center service provider. In some embodiments, the projected revenue analysis engine 272 supplies requested metrics to a provider report generation engine 286 for further processing.

In some implementations, the predictive analytics platform includes a provider peer identification engine 274 for identifying service providers 208 similar to a subject service provider. The provider peer identification engine 274, for example, may filter the service provider data 252 to identify only those service providers 208 sharing one or more common characteristics with the subject service provider.

The characteristics, in some examples, can include a type of service provider (e.g., hospital, outpatient surgical facility, private medical practice, medical transportation provider, etc.), a size of service provider (e.g., by number of employees, number of medical professionals, number of beds for hospital type service providers, size of fleet for medical transportation service provider, and/or by financial metrics such as annual income range), a geographic footprint of service provider (e.g., municipal, regional, national, etc.), and/or a tax classification of service provider (e.g., for-profit or not for-profit). Further, the provider peer identification engine 274 may filter the service provider data 252 based upon availability of information (e.g., to ensure certain metrics will be represented and/or metrics details will be capable of being derived over a desired range of time). The peer identification engine 274, in some embodiments, applies filtering to ensure a collection of at least a threshold number of service providers such that comparison metrics derived using the set of service providers will not be capable of reverse engineering to obtain confidential financial data related to a particular service provider. The provider peer identification engine 274 may identify the peer providers to a requesting application, such as the provider report generation engine 286, by a provider identification number or code.

The predictive analytics platform 102, in some implementations, includes a procedure trends analysis engine 276 configured to analyze historic claims data for patients who underwent major procedures, such as surgical procedures, to identify patterns within the claims data near the time of the procedure and shortly thereafter (e.g., days, 1 week, weeks, 1 month, or up to multiple months) that may be indicative of follow-on services and/or prescription products commonly associated with the major procedure. The patterns, in some examples, may include services commonly paired with each major procedure, common follow-on services to each major procedure, and/or prescriptions commonly paired with each major procedure. Further, the patterns may be broken down into subsets, such as services commonly paired with each major procedure by demographic group (e.g., age range, gender, race), services commonly paired with each major procedure by patient prescription (e.g., certain prescriptions may be indicative of a more serious condition, such as more serious chronic heart failure), common follow-on services to each major procedure by demographic group, services commonly paired with each major procedure by patient co-morbidity (e.g., high blood pressure, diabetes, cancer, congestive heart failure, obesity, etc.), and/or common follow-on services to each major procedure by co-morbidity. In some embodiments, the procedure trends analysis engine 276 applies machine learning analysis, cluster analysis, and/or statistical data analysis to historic claims data (e.g., the historic claims data 256) to identify data patterns within the accessed records. For example, the procedure trends analysis engine 276 may include different machine learning classifiers trained to identify patterns related to the various sets and subsets of procedures and patient demographics and/or medical history. The machine learning classifiers, for example, may be trained using de-identified data collected over a period of time (e.g., at least 3 months, from 3 to 6 months, up to 1 year, 2 years, etc.). The scope of the training data, for example, may depend upon an amount of data available related to the different variables (e.g., an amount of data per major procedure, an amount of data per age range, etc.). The procedure trends analysis engine 276 may return groupings of medical codes and/or identifications (e.g., procedures, prescriptions, equipment, etc.) determined to be likely interrelated based upon a subject patient and a subject procedure.

In some implementations, the predictive analytics platform 102 includes the patient report generation engine 278 configured to generate reports related and/or for use by patients. The reports, in some examples, may include a patient propensity to pay report card, a patient financial assistance report, and/or a patient personal health report. The patient report generation engine 278 may leverage the predictive analytics platform 102 to obtain predictive intelligence related to generate patient-focused reports. For example, the patient report generation engine 278 may obtain predictive analytics regarding a patient's likelihood to pay using one or more patient propensity to pay by medical debt level and/or credit score classifiers 190. The patient propensity to pay by medical debt level and/or credit score classifier(s) 190, for example, may be trained using patient data 124 related to personal finances as well as historic claims data 120 including patient out-of-pocket expenses. In another example, the patient report generation engine 278 may obtain predictive analytics regarding procedure costs based upon comorbidity factors using one or more medical costs by procedure and comorbidit(ies) classifiers 192. The one or more medical costs by procedure and comorbidit(ies) classifier(s) 192, for example, may be trained using patient data 124 related to chronic conditions as well as historic claims data 120.

In some implementations, the predictive analytics platform 102 includes the provider report generation engine 286 configured to organize historic and/or forecast metrics such as revenue metrics 264 and remittance metrics 266 and prepare presentations related to the metrics. The reports prepared via the provider report generation engine 268, in some examples, may be organized for use by providers, such as hospitals, medical facilities, and/or transportation providers. The reports, in some examples, may include reports related to projected revenue and/or provider financial metrics. The provider financial metrics, further, may include comparisons to other similar providers. The provider report generation engine 286 may leverage the predictive analytics platform 102 obtain predictive intelligence related to the revenue streams and other financial metrics of providers, for example based on the provider data 122 component of the data universe 104 (see, for example, FIG. 1A). As illustrated in FIG. 1D, for example, the predictive analytics platform 102 includes one or more reimbursement rate trends by plan and procedure type classifiers 184, one or more time from invoicing to reimbursement by plan and by procedure type classifiers 186, and one or more payment patterns by revenue cycle and/or by billing code category classifiers 188. The reimbursement rate trends by plan and procedure type classifier(s) 184 and the time from invoicing to reimbursement by plan and by procedure type classifier(s) 186, for example, may be trained using plan data such as a plan data set 244 of FIG. 2, procedure data such as a procedure data set 248 of FIG. 2, and remittance data such as a remittance data set 262 of FIG. 2. The payment patterns by revenue cycle and/or by category classifier(s) 188, for example, may be trained using medical coding data such as a procedure coding data set 260 of FIG. 2 and the remittance data set 262 of FIG. 2. The provider report generation engine 286, for example, may combine forecast metrics with historic metrics (e.g., past revenue quarters plus one or more future revenue quarters) to visually present revenue trends over time. Further, the provider report generation engine 286 may generate tables, charts, bar graphs, line graphs, and/or other graphical displays to visually represent comparisons in the forecast metrics and/or between the historic metrics and the forecast metrics.

In some implementations, the predictive analytics platform 102 includes an assistance availability analysis engine 280 configured to automatically investigate potential additional sources of medical debt coverage for uninsured or underinsured patients. The assistance availability analysis engine 280, for example, may analyze patient demographic data to identify additional funding sources such as, in some examples, any federal programs, state programs, charitable foundation programs, and/or foundation discount programs. The additional funding sources may vary by location, type of service provider, income level, age, and/or employment status of the patient. Upon identifying eligibility for at least certain programs, such as the federal Medicare and Medicaid programs, the assistance availability analysis engine 280 may automatically initiate enrollment in the programs by filling out online form(s) or other eligibility paperwork using the demographic data stored by the predictive analytics platform 102 in the patient data 240. Further, the assistance availability analysis engine 280, in some embodiments, accesses additional information regarding the payer, such as credit history or debt information, from third party sources to determine eligibility and/or to provide a larger percentage of required information to the eligibility form(s)/paperwork.

In some implementations, the predictive analytics platform 102 includes a patient financial rating engine 282 for scoring or grading the ability of the patient to cover out-of-pocket medical expenses. The patient financial rating engine 282, in some embodiments, gathers current financial data regarding a subject patient such as, in some examples, outstanding medical invoices, pending medical claims, and/or scheduled procedures to determine a current medical debt status of the patient. Further, in some embodiments, the patient financial rating engine 282 gathers historic invoice information to determine a payment pattern of the subject patient (e.g., timeliness of paying past medical invoices).

The patient financial rating engine 282 may additionally, in some embodiments, access a general credit score or credit report related to the patient, for example from a credit reporting agency or financial institution. The financial data regarding the subject patient, in some implementations, is applied by the patient financial rating engine 282 to the patient payment pattern engine 234 to generate a relative comparison of payment estimates in relation to a patient population of data captured in the patient data 240 of the data repository 210.

In some embodiments, the patient financial rating engine 282 generates a numeric score. The numeric score, in some examples, may be similar to a general credit score (e.g., on a numeric scale of 300 to 850), a scaled ranking (e.g., 1 to 5, 1 to 10, etc.), or a quantile ranking (e.g., percentile, quartile, quintile, etc.). In other embodiments, the patient financial rating engine 282 generates a characterization of the patient's financial rating such as, in some examples: poor, fair, good, very good, or excellent; below average, average, or above average; or low risk, acceptable risk, or high risk. In further embodiments, the patient financial rating engine 282 generates a letter grade characterizing the patient's financial rating (e.g., A through F).

The predictive analytics platform 102, in some implementations, includes a provider financial rating engine 284 for determining a comparative financial rating of a subject service provider. The provider financial rating engine 284, in some embodiments, gathers current financial data regarding a subject service provider such as, in some examples, accounts receivables data, payments data, adjustments data, account balance data, and/or average days of revenue outstanding. Further, in some embodiments, the provider financial rating engine 284 gathers historic financial data over at least a threshold period of time (e.g., one year, three years, five years, etc.). The financial data, for example, may be collected by the predictive analytics platform 102 in the service provider data 252. Further, financial data collected over time may be stored as revenue metrics 264 and/or remittance metrics 266. The provider financial rating engine 284 may additionally, in some embodiments, access a business rating such as a credit rating or bond rating. The business rating, for example, may be provided by Fitch Ratings Inc. of New York, NY, Moody's Corporation of New York, NY, or S&P Global Inc. of New York, NY. Further, the provider financial rating engine 284 may take into consideration a business dealings rating such as a Better Business Bureau (BBB) rating by the Better Business Bureau of Arlington County, VA.

The provider financial rating engine 284, in some implementations, benchmarks the subject service provider based upon financial data metrics for a plurality of other service providers. The service providers, in some examples, may include all service providers having data accessible to the predictive analytics platform 102, all service providers within a same geographic region (e.g., country, state, county, etc.), all service providers of a same type as the subject service provider, and/or all service providers of a same income range as the subject service provider. In some embodiments, the other service providers used for benchmarking are identified by the provider peer identification engine 274.

In some embodiments, the provider financial rating engine 284 generates a numeric score. The numeric score, in some examples, may be similar to a general credit score (e.g., on a numeric scale of 300 to 850), a scaled ranking (e.g., 1 to 5, 1 to 10, etc.), or a quantile ranking (e.g., percentile, quartile, quintile, etc.). In other embodiments, the provider financial rating engine 284 generates a characterization of the service provider's financial rating such as, in some examples: poor, fair, good, very good, or excellent; below average, average, or above average; or low risk, acceptable risk, or high risk. In further embodiments, the provider financial rating engine 284 generates a letter grade characterizing the service provider's financial rating (e.g., A through F).

Figure 3A:
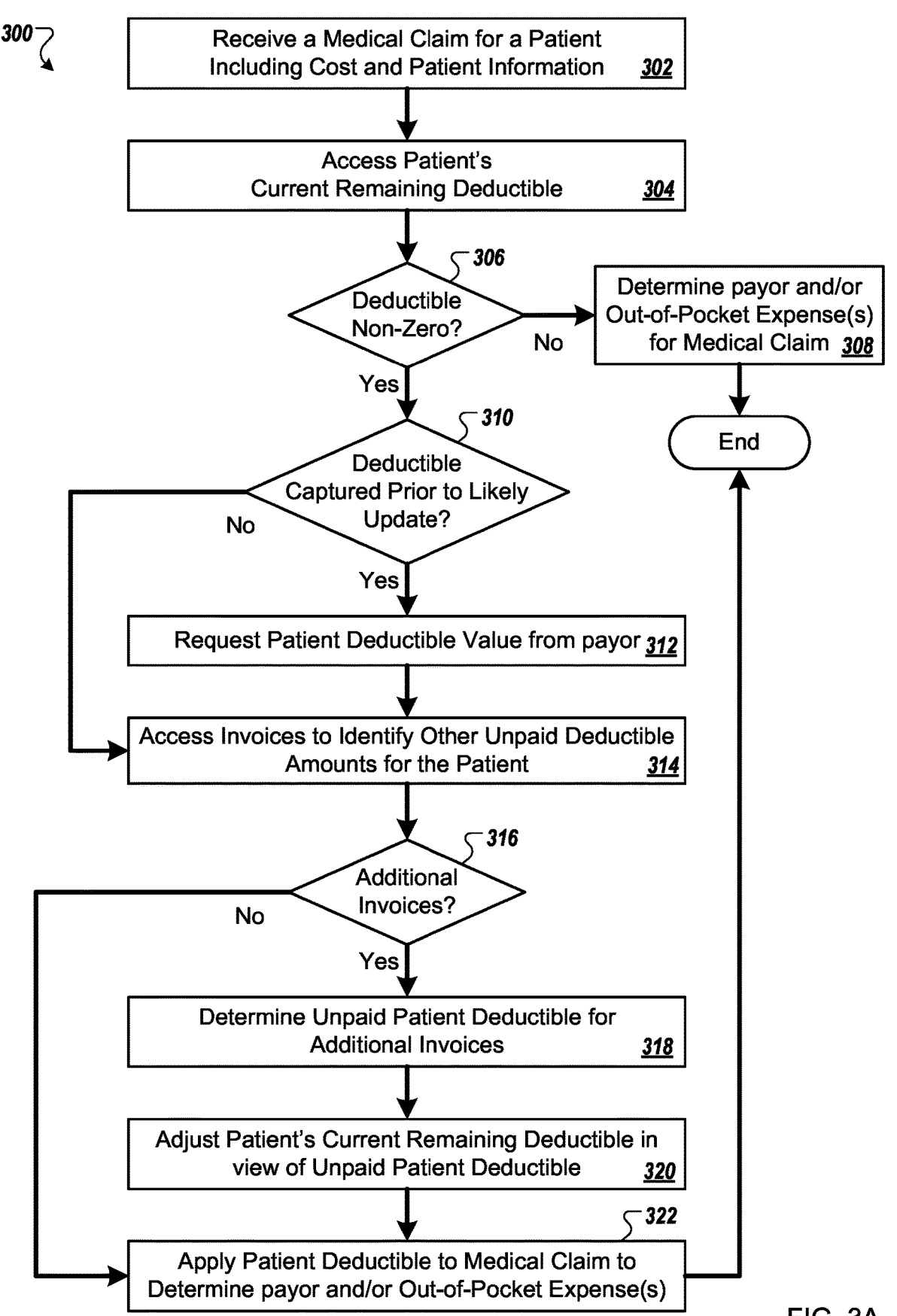
FIG. 3A illustrates a flow chart of an example method for estimating a patient's current deductible amount.

FIG. 3A illustrates a flow chart of an example method 300 for estimating a patient's current deductible amount. At least portions of the method 300, for example, may be executed by the deductible estimation engine 220 of the predictive analytics platform 102, as described in relation to FIG. 2. Portions of the method 300 may be enabled by the deductible updating pattern by payer classifier(s) 176 described in relation to FIG. 1D.

In some implementations, the method 300 begins with receiving a medical claim for a patient including cost and patient information (302). The medical claim, for example, may be medical claim data provided by the claims and billing platform 150 to the predictive analytics platform 102 while executing the claims processing engine 162 or services scheduling engine 164, discussed in relation to FIG. 1D. The medical claim data may include information identifying a patient, one or more procedure or other medical codes, and/or information identifying a payer.

In some implementations, a patient's current remaining deductible is accessed (304). The remaining deductible, for example, may a stored value (e.g., in the data universe 104 and/or a storage region associated with the claims and billing platform 150) accessed previously from a payer to which the medical claim is directed. The patient's current remaining deductible, in another example, may be a deductible retrieved from a payer's system, for example by issuing an automated request for a computing system of the payer.

In some implementations, if the current remaining deductible (306) is zero, payer and/or out-of-pocket expenses for the medical claim are determined (308) and the method 300 ends. Determining the expenses, for example, may include identifying any co-pay value to the patient and/or a residual out-of-pocket expense after a maximum benefits level is reached. Determining the payer expenses, for example, may include determining an in-network or out-of-network charge level accepted by the payer for the services identified by the procedure codes of the medical claim.

If, instead, the patient's current remaining deductible (306) is non-zero, in some implementations, it is determined whether the deductible captured as the current remaining deductible has been captured prior to a likely update of the deductible amount (310). For example, the deductible updating pattern by payer classifier(s) 176 may be applied to determine if a locally stored current remaining deductible is likely to have been updated and/or if the remaining deductible value as reported by the payer is likely to be updated based upon the payer's pattern of adjusting deductible amounts.

If the deductible amount is likely to not reflect an actual current value, in some implementations, an updated patient deductible value is requested from the payer (312). A request for the current deductible amount, for example, may be requested immediately. In another example, the system may schedule a request for the current deductible amount from the payer for a later date or time at which it is anticipated that the deductible will have been updated (e.g., in 12 hours, up to 24 hours, 1-3 days, or up to a week).

In some implementations, invoices are accessed to identify other pending deductible payments for the patient (314). The patient, for example, may have accrued a number of claims for related services such as, in some examples, an emergency transportation service in addition to hospital services. Further, multiple days of testing, hospital stay, or other medical procedures may have accrued in multiple claims for various services. Invoices, pending claims, and/or submitted claims for the same patient may be reviewed to identify other unpaid amounts that can affect the current deductible amount.

In some implementations, if additional invoices are identified (316), an unpaid patient deductible is determined for the additional invoices (318) and the patient's current remaining deductible is adjusted in view of the unpaid patient deductible (320).

Whether or not additional invoices were located (316), in some implementations, the patient deductible is applied to the medical claim to determine payer and/or out-of-pocket expenses (322).

Although described as a particular series of operations, in some embodiments, more or fewer steps may be included in the method 300. For example, in addition to accessing invoices (314), in some implementations, other claims pending submission may be reviewed. In further embodiments, certain steps of the method 300 may be performed in a different order or in parallel. For example, the additional invoices (316) may be reviewed prior to determining whether the deductible was captured prior to likely update (310). For example, if the amount of the deductible associated with unpaid invoices would leave the current remaining deductible at zero, the up-to-date deductible information would never need to be requested from the payer. Other modifications of the method 300 are possible while remaining within the scope and purpose of the method 300.

Figure 3B:
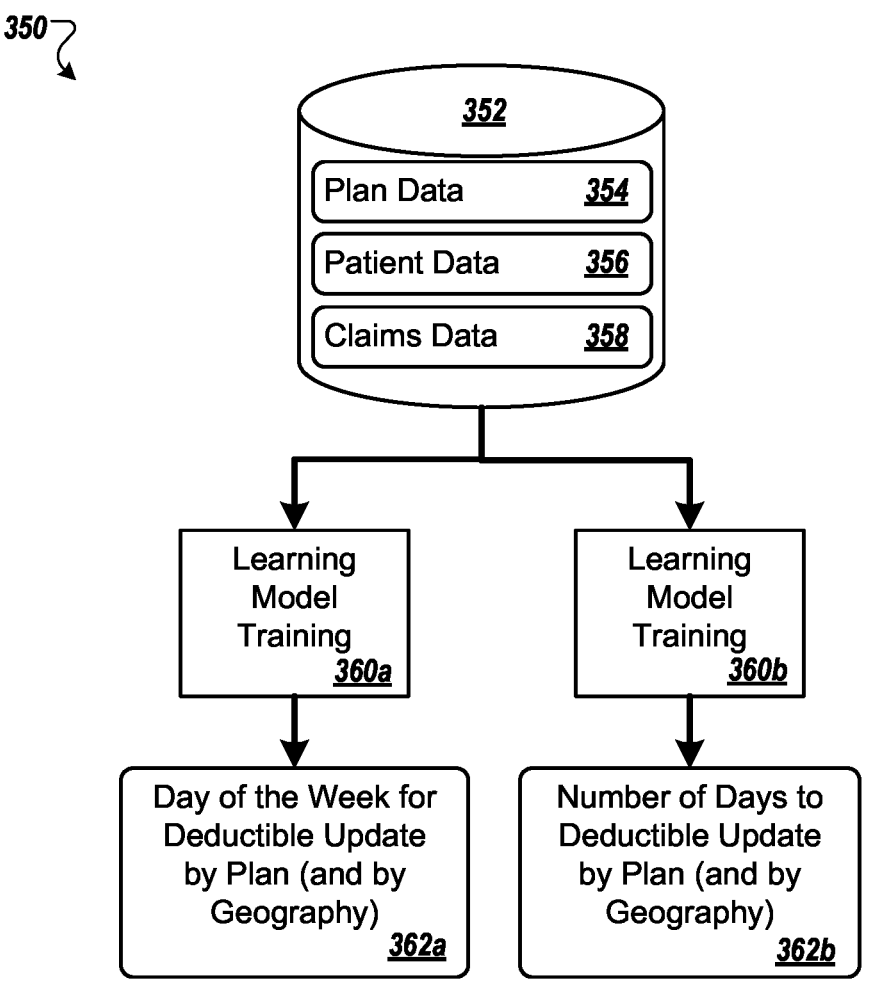
FIG. 3B illustrates a flow diagram of an example process for training machine learning classifiers for anticipating deductible updates.

FIG. 3B illustrates a flow diagram of an example process 350 for training machine learning classifiers for anticipating deductible updates. The machine learning classifiers generated by the process 350, for example, may be used by the method 300 of FIG. 3A for determining whether the patient's current remaining deductible was captured prior to a likely update to its value (310). In another example, the deductible timing pattern engine 222 of FIG. 2 may apply the machine learning classifiers generated by the process 350 to determine deductible update patterns. The output of the process 350, in an example, may result in the deductible updating pattern by payer classifier(s) 176 of FIG. 1D.

In some implementations, the process 350 begins with accessing plan data 354 and/or patient data 356 as well as claims data 358 from a storage region 352. The plan data 354, for example, may correspond to the plan data 244 as described in relation to FIG. 2. The patient data 356 may correspond to the patient data 240 as described in relation to FIG. 2, and the claims data 358 may correspond to the historic claims data 256 as described in relation to FIG. 2. The plan data 354, patient data 356, and claims data 358 may be linked through a particular subscriber (e.g., by subscriber identifier). In some implementations, the plan data 354, patient data 356, and/or claims data 358 are collected from the data universe 104 (e.g., patient data 124, payer data 126, and historic claims data 120) described in relation to FIG. 1A.

In some implementations, the plan data 354, patient data 356, and/or claims data 358 are provided to a first learning model training engine 360*a* to train a set of day of the week for deductible update by plan and/or a day of the week for deductible update by plan and by geography classifiers 362*a* to recognize patterns ("trends") in differences in deductible values from one day to the next or from one portion of a week to a next portion of a week. This may be inferred, in some examples, through repeated claim submissions within a short timespan and each associated with a certain patient (or set of patients covered by a same plan, such as a family plan).

The first learning model training engine 360*a*, in some embodiments, includes a neural network-based analysis, such as a recurrent neural network (RNN). The RNN, for example, may consider additional claims information, such as a geographical region of the patient's address, identification of the patient's employer, and/or geographic region of the patient's employer to analyze trends in deductible updating. Other learning model algorithms and/or neural network-based analysis tools may be applied to train the day of the week for deductible update classifiers 362*a*.

In some implementations, plan data 354, patient data 356, and/or claims data 358 are provided to a second learning model training engine 360*b* to train a learning model 362*b* to predict a number of days to deductible update by plan and/or by plan and further by geography 362*b*. As described in relation to the learning model training engine 360*a*, a variety of machine learning algorithms and/or deep learning analysis networks may be used to train the number of days to deductible update machine learning classifiers 362*b*.

Figure 4A:
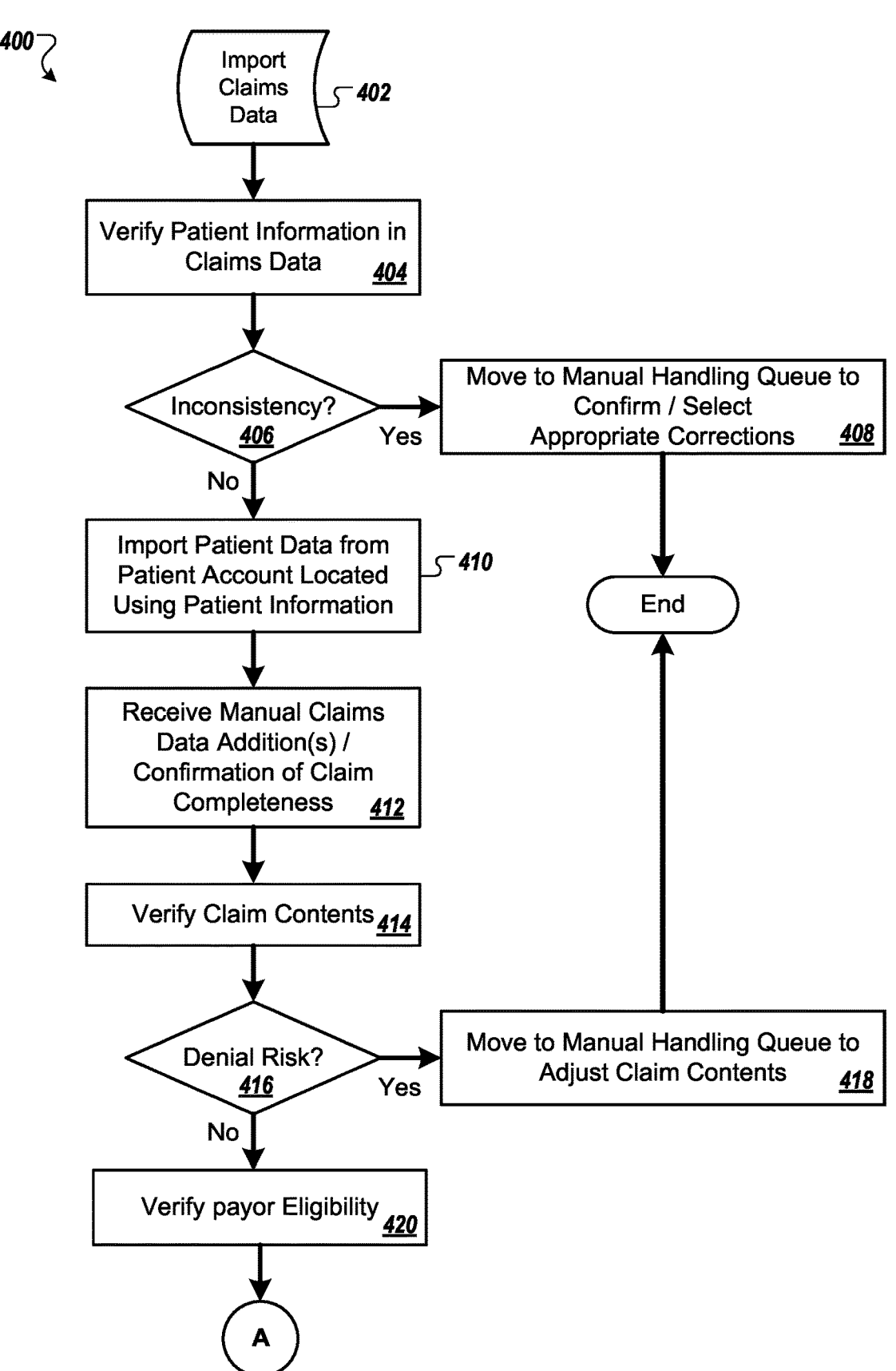
FIG. 4A and FIG. 4B present a flow chart of an example method for automating claims processing.
Figure 4B:
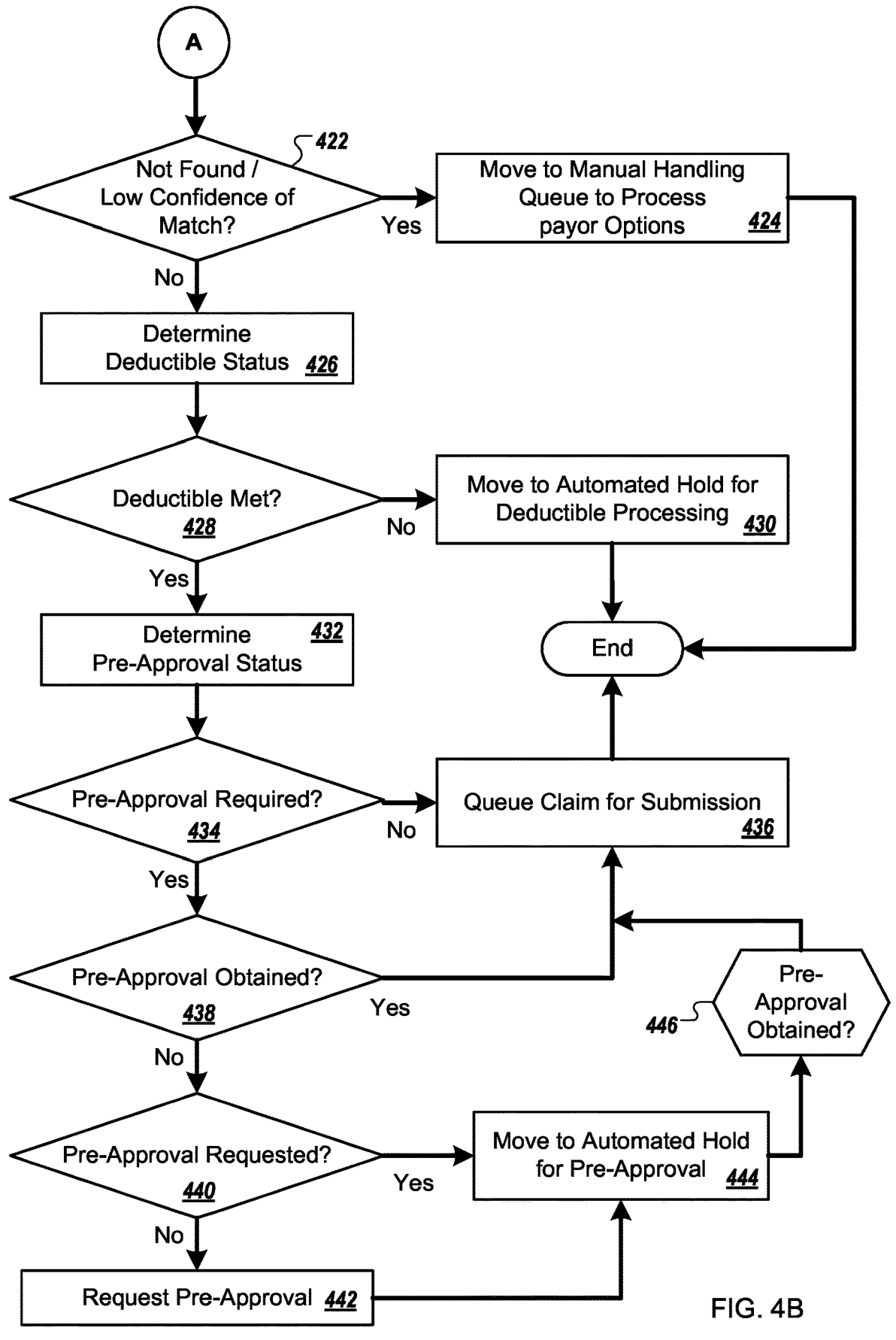

FIG. 4A and FIG. 4B present a flow chart of an example method 400 for automating claims processing. The method, for example, may be performed by the claims and billing platform 150 in coordination with the predictive analytics platform 102, as described in relation to FIG. 1A-1G. For example, portions of the method may be performed by the claims processing engine 162 of FIG. 1D.

Turning to FIG. 4A, in some implementations, the method 400 begins with importing claims data (402). The claims data 402 may be imported, for example, from an electronic medical record or other procedure code entry system or service.

In some implementations, patient information in the claims data is verified (404). The patient information may be verified, for example, using the patient data verification engine 214 of the predictive analytics platform 102, as described in relation to FIG. 2. The verification, for example, may be performed in part by executing the likelihood of patient record match classifier(s) 178 of FIG. 1D.

In some implementations, if an inconsistency between the patient information and patient records is discovered (406), the claim is moved to a manual handling queue to confirm proposed change(s) and/or to select appropriate corrections to the patient information (408) and the method 400 ends. For example, a claims agent may be provided with two or more potential patient records identified as partial matches to the patient information. In another example, the claims agent may be provided with an updated address, variation of first name spelling, or other inconsistency for approval.

In some implementations, if no inconsistency is discovered (406), patient data is imported from the patient account located using the patient information (410). For example, additional information not contained in the patient information, such as current address, payer identifier(s), middle name, etc. may be imported to fill in missing information in the claims data.

Figure 6A:
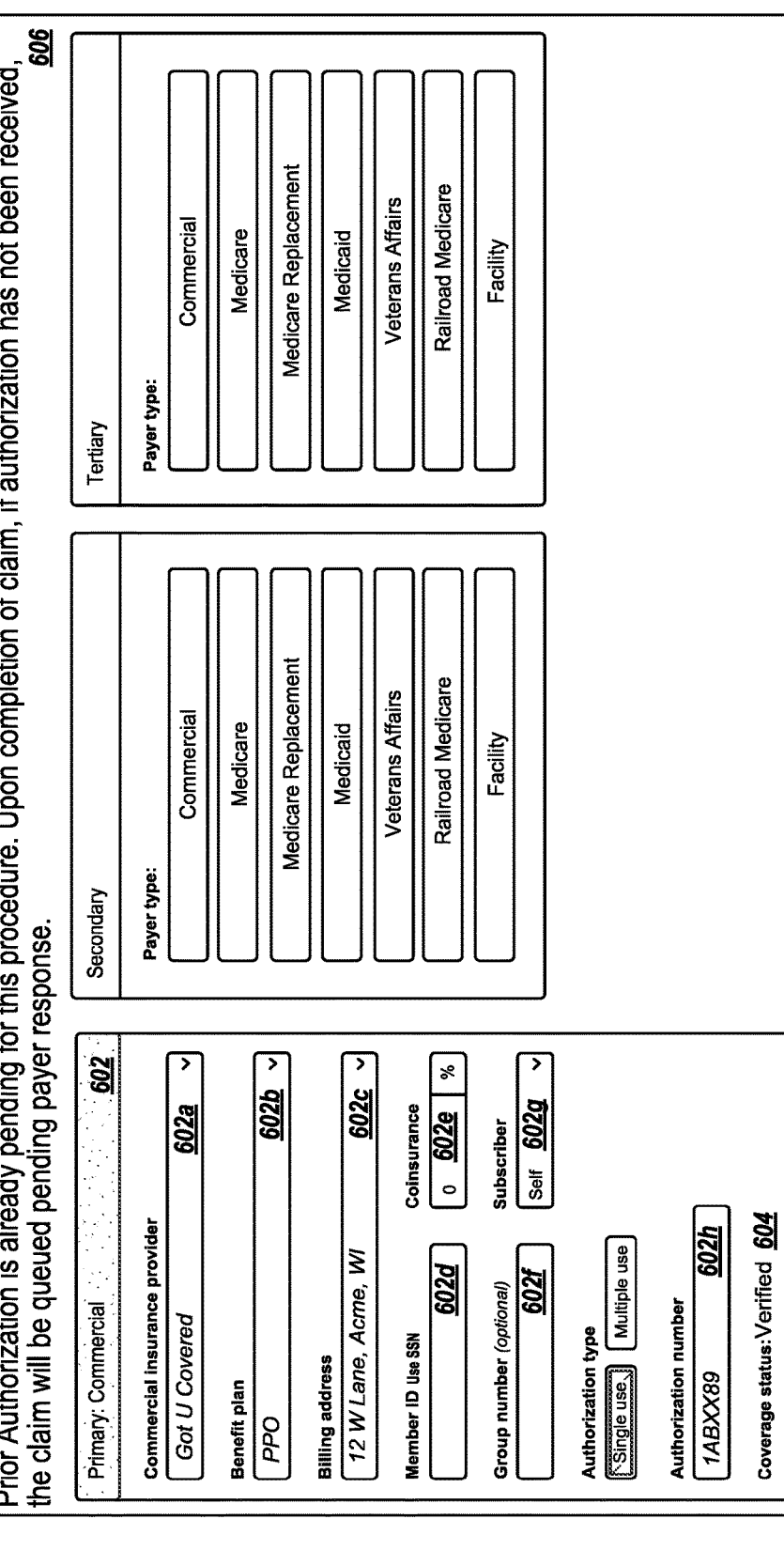

In some implementations, manual claims data additions and/or a confirmation of claim completeness is received from a claims processing agent (412). The manual claims data additions and/or confirmation of claim completeness, for example, may be received by the predictive analytics platform 102 from the claims processing engine 162, illustrated in FIG. 1D. Turning to FIG. 6A, in some implementations, an example claims processing data entry screen 600 includes data population fields, such as a set of data population fields 602 related to primary insurance information. As illustrated, the data population fields 602 include drop-down menu fields for commercial insurance provider 602a, benefit plan 602b, billing address 602c, and subscriber 602g as well as data entry fields for member identifier 602d, co-insurance percentage 602e, group number 602f, and authorization number 602h. Upon receipt of information through one of the set of data population fields 602, for example, the claims data addition may be received for verification. In some implementations, a data entry screen 600 such as the example claims processing data entry screen 600 includes a control that, when selected, indicates that the claims agent has confirmed that the contents of the medical claim are complete and ready for submission.

In some implementations, claims contents are verified (414). For example, the predictive analytics platform 102 may verify entry into the set of data fields 602 of FIG. 6A using the required claims fields by payer classifier(s) 180 of FIG. 1D to confirm that all required fields include information. If some information is missing, in some embodiments, the missing information may be provided for automatic population. For example, if the member identifier field 604d is required and not populated, the member identifier may be accessed by the predictive analytics platform 102 from the patient data 124 of the data universe 104 (e.g., as shown in FIG. 1A). Further, in the circumstance of procedure codes or other billing codes being included in the claims data provided to the predictive analytics platform 102, the likelihood of procedure code approval by payer classifier(s) 182 may be executed to confirm that the billing codes entered into the medical claim are not likely to invoke denial by the payer. The claims data verification engine 230 of FIG. 2, for example, may invoke the required claims fields by payer classifier(s) 180 and/or the likelihood of procedure code approval by payer classifier(s) 182 of FIG. 1D.

In some implementations, if substantial risk of denial is determined through the verification (416), the claim is moved to a manual handling queue to adjust contents of the claim 418) and the method 400 ends. For example, turning to FIG. 6C, the in-process medical claim may be queued to a set of incomplete claims 642 of a screen shot of an example claims status user interface 640. The in-process medical claim, for example, may be assigned to one of the users 648 for review. The review process, for example, may include reviewing recommended additions and/or substitutions to the data fields of the medical claim provided by the claims processing assistance engine 228 of FIG. 2. For example, the virtual assistance feedback 132 may be presented to one of the users 648 via the claims and billing portal 110, as described in relation to FIG. 1B.

If, instead, no substantial risk of denial is determined (416), in some implementations, the patient's eligibility with the payer is verified (420). For example, patient-provided insurance information may be confirmed against information in the data universe 104 and/or confirmed via issuing a request to the payer for insurance confirmation. For example, the data universe 104 may first be invoked to compare the patient-provided insurance information to likely insurance information (e.g., via the payer identification engine 218 of FIG. 2). The patient's eligibility, in another example, may be confirmed through submitting patient account information, such as the member identifier in the member identifier field 602d of FIG. 6A to the payer 206 identified in the insurance provider data field 602a. As illustrated in FIG. 6A, for example, the coverage status 604 for the primary insurance information in the data fields 602 is verified.

Turning to FIG. 4B, in some implementations, if an active payer account for the listed payer is not found using the patient information and/or there is a low confidence of match between the patient information and the identified payer, the medical claim is moved to a manual handling queue to process payer options 424 and the method 400 ends. For example, turning to FIG. 6C, the in-process medical claim may be queued to a subset of incomplete claims due to account inconsistencies 642a of the example claims status user interface 640. The in-process medical claim, for example, may be assigned to one of the users 648 for review.

Returning to FIG. 4B, if, instead, the patient's insurance is verified, in some implementations, a deductible status is determined (406). For example, as illustrated in FIG. 2, the deductible estimation engine 220 may be invoked to determine a current deductible status. The deductible status, for example, may be determined using the method 300 described in relation to FIG. 3.

Figure 6B:

In some implementations, if the deductible has not been met 428, the medical claim is moved to an automated hold for deductible processing routine (430) and the method 400 ends. Turning to FIG. 6C, for example, the in-process medical claim may be queued to a subset of incomplete claims queued for deductible monitoring 642c of the example claims status user interface 640. FIG. 6B illustrates a screen shot of an example deductible monitoring settings interface 620 for setting values associated with deductible monitoring. Turning to FIG. 6B, for example, the medical claim may be queued for automated deductible monitoring 622 for a maximum number of days 624, illustrated as 90 days. In some implementations, the queuing further depends on a dollar value threshold 626 of the potential patient responsibility for the medical claim and/or a patient's annual deductible amount 628 being greater than a threshold deductible value. As stated in a user notice 630 of the example deductible monitoring settings interface 620, "periodic deductible monitoring is based on payer and plan information to streamline claims processing." The periodic deductible monitoring, for example, may be established using the deductible timing pattern engine 222 of FIG. 2, based on predictive intelligence derived using the deductible updating pattern by payer classifier(s) 176 of FIG. 1D.

Returning to FIG. 4B, in some implementations, if the deductible has been met (428), a pre-approval status is determined (432). The pre-approval status, for example, may be determined for one or more medical codes of the medical claim by the payer pre-approval analysis engine 224 of FIG. 2.

If pre-approval is not required (434), in some implementations, the claim is queued for submission (436) and the method 400 ends. Turning to FIG. 6C, for example, the medical claim may be queued for manual submission 644a or automated submission. Manual submission, for example, may include preparing a paper copy and/or faxing information to the payer. Manual submission, conversely, may include electronically submitting the medical claim to a computing system of the payer, for example using an API provided by the payer. In the circumstance of manual submission, in some implementations, a queued for submission status 652h may automatically update to a submitted status 652i once a confirmation from the payer has been received via automated submission.

Returning to FIG. 4B, in some implementations, if pre-approval is required (434), it is determined if pre-approval has been obtained (438). The pre-approval request may have been submitted by the payer pre-approval request engine 226, described in relation to FIG. 2. For example, turning to FIG. 6A, the user interface 600 includes a user message 606 stating "prior authorization is already pending for this procedure. Upon completion of the claim, if authorization has not been received, the claim will be queued pending payer response." The pre-approval request, for example, may have been automatically submitted as part of the electronic medical record process, prior to being imported (402) by the method 400. In another example, pre-approval may have been obtained via the services scheduling engine 164 of FIG. 1D while scheduling the medical procedure for the patient.

Returning to FIG. 4B, in some implementations, if pre-approval has been obtained (438), in some implementations, the medical claim is queued for submission (436) and the method 400 ends.

If, instead, pre-approval has not been obtained (438), if pre-approval has already been requested (440), the medical claim is moved to an automated hold for pre-approval queue (444). For example, turning to FIG. 6C, the medical claim may be moved to a pending prior authorization queue 642 of the incomplete claims 642. An automated routine, for example, may move the medical claim from queued to submitted based upon receipt of prior authorization approval. If, instead, the prior authorization request is denied, the automated routine may move the medical claim to a denied queue 644c, where a denied status 652e is applied until manual intervention by one of the users 648 resolves the issue.

Returning to FIG. 4B, in some implementations, if pre-approval has not been requested (440), a request for pre-approval is submitted (442), and the medical claim is moved to the automated hold queue for pre-approval (444).

Once pre-approval has been obtained (446), the claim is queued for submission (436) and the method 400 ends.

Although described as a particular series of operations, in some embodiments, more or fewer steps may be included in the method 400. For example, in some embodiments, the manual claims data addition receipt (412) and claim content verification (414) may be iterative to ensure accuracy and completeness of information as it is being entered by a claims processing agent (e.g., via the claims processing assistance engine 228 of FIG. 2). In another example, in addition to determining whether a denial risk is present (416), the method 400 may determine whether an inconsistency in claims data, beyond the patient data, exists. In further embodiments, certain steps of the method 400 may be performed in a different order or in parallel. For example, payer eligibility may be verified (420) prior to verifying the claim contents (414). This may be useful, for example, in circumstances where the medical codes are confirmed based upon the payer (e.g., by the claims data verification engine 230 of FIG. 2 using the likelihood of procedure code approval by payer classifier(s) 182. Other modifications of the method 400 are possible.

Figure 5:
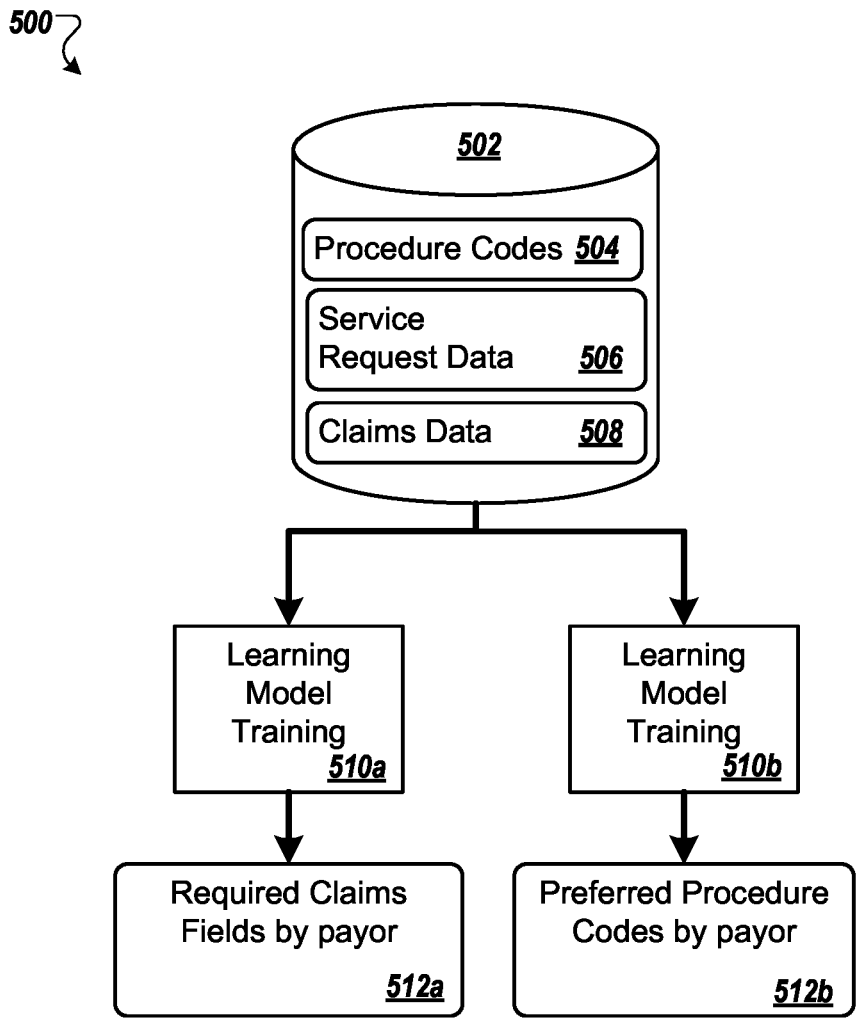
FIG. 5 illustrates a flow diagram of an example process for training machine learning classifiers for determining claim fields required by a payer and preferred procedure codes accepted by a payer.

FIG. 5 illustrates a flow diagram of an example process 500 for training machine learning classifiers for determining claim fields required by a payer and preferred procedure codes accepted by a payer. The machine learning classifiers generated by the process 500, for example, may be used by the method 400 of FIG. 4A for verifying claim contents (414). In another example, the claims data verification engine 230 of FIG. 2 may apply the machine learning classifiers generated by the process 500 to determine approval patterns for procedure codes. A portion of the information gleaned by the process 500, in some embodiments, may be stored as procedure coding data 260, described in relation to FIG. 2. The output of the process 500, in an example, may result in the likelihood of procedure code approval by payer classifier(s) 182 of FIG. 1D.

In some implementations, the process 500 begins with accessing procedure codes 504, service request data 506, and claims data 508 from a storage region 502. The procedure codes 504, for example, may correspond to the plan requirements data for claims processing 250 as described in relation to FIG. 2. The service request data 506 may correspond to the service request data 258 as described in relation to FIG. 2, and the claims data 358 may correspond to the historic claims data 256 as described in relation to FIG. 2. The procedure codes 504, service request data 506, and claims data 508 may be linked through a particular patient (e.g., by subscriber identifier). In some implementations, at least a portion of the procedure codes 504, service request data 506, and claims data 508 are collected from the data universe 104 (e.g., including historic claims data 120) described in relation to FIG. 1A.

In some implementations, the service request data 506 and claims data 508 are provided to a first learning model training engine 510a to train a set of required claims fields by payer classifiers 512a to recognize patterns ("trends") in claims denials based on lack of required information. The lack of required information may include data information fields such as, in some examples, payer address, subscriber group number, and/or provider address. In some embodiments, the procedure codes 504 may further be provided to the first learning model training engine 510a to identify, for example, sets of procedure codes that commonly are used together such that including one without the other may lead to claim denial.

The first learning model training engine 510a, in some embodiments, includes a decision tree learning model algorithm such as a random forest model algorithm to classify data information fields of medical claims as required or optional. The decision tree learning model algorithms, for example, provide strong accuracy on data sets appropriate to supervised learning (e.g., pre-matched known truth data). In some embodiments, the first learning model training engine 510a includes neural network-based analysis for categorizing data information fields of medical claims based on patterns within denied claims, such as a recurrent neural network (RNN). The RNN, for example, may receive additional patient information, such as geographical region, employer, etc. to identify payer patterns in denial based on procedure code. Other learning model algorithms and/or neural network-based analysis tools may be applied to train the required claims fields by payer classifiers 512a.

In some implementations, the procedure codes 504, service request data 506, and claims data 508 are provided to a second learning model training engine 510b to train a set of preferred procedure codes by payer learning models 512b to predict denial or approval based on medical code usage. For example, in medical coding, in many circumstances, two or more procedure codes may be applied to a same type of medical service, equipment, or prescription. Thus, certain payers may prefer certain alternatives corresponding to a same general service, equipment, or prescription. As described in relation to the learning model training engine 510a, a variety of machine learning algorithms and/or deep learning analysis networks may be used to train the preferred procedure codes by payer classifiers 512a.

Figure 8A:
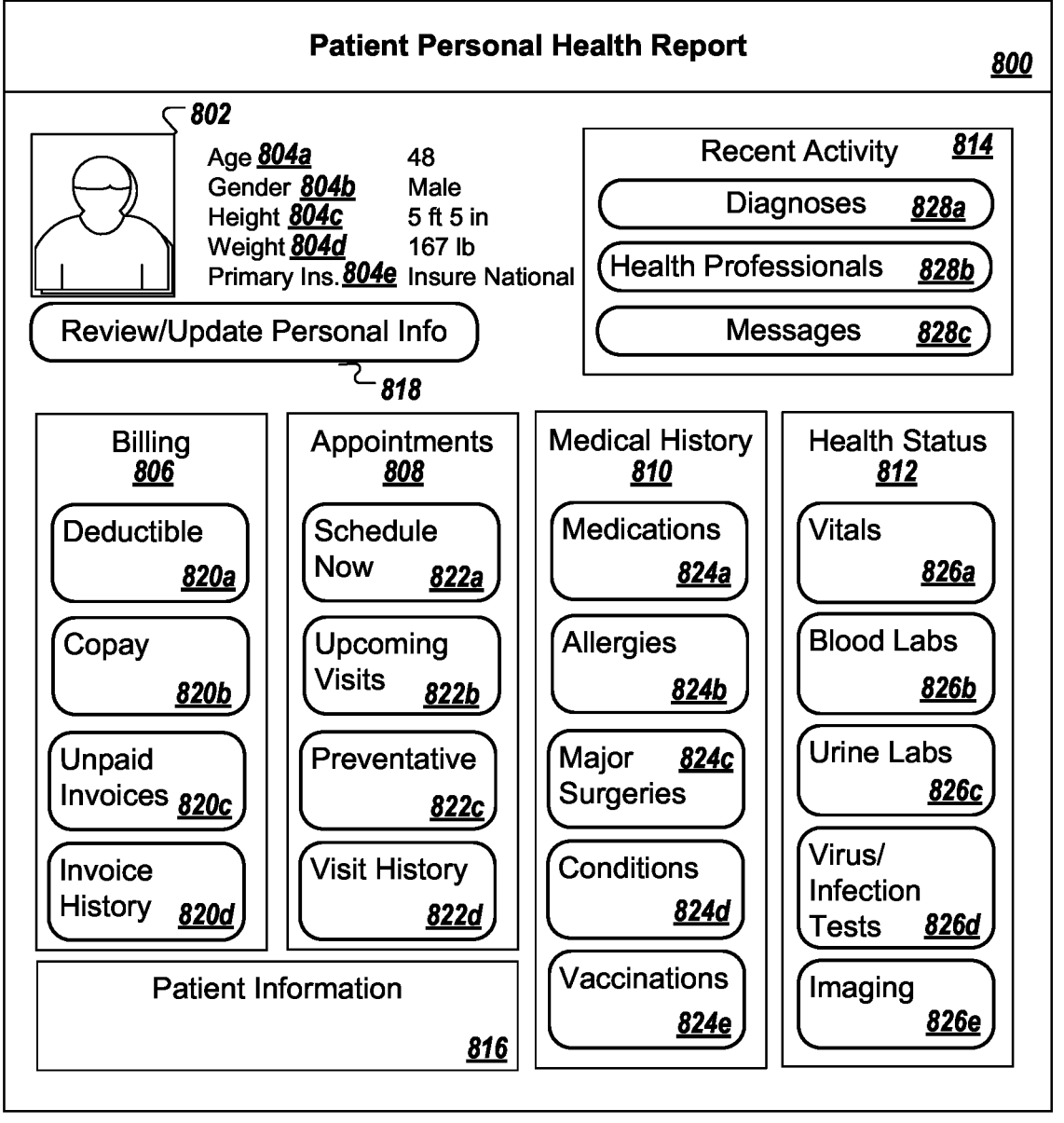
FIG. 8A illustrates an example of a patient report card for personal health information and medical financial information.
Figure 8C:
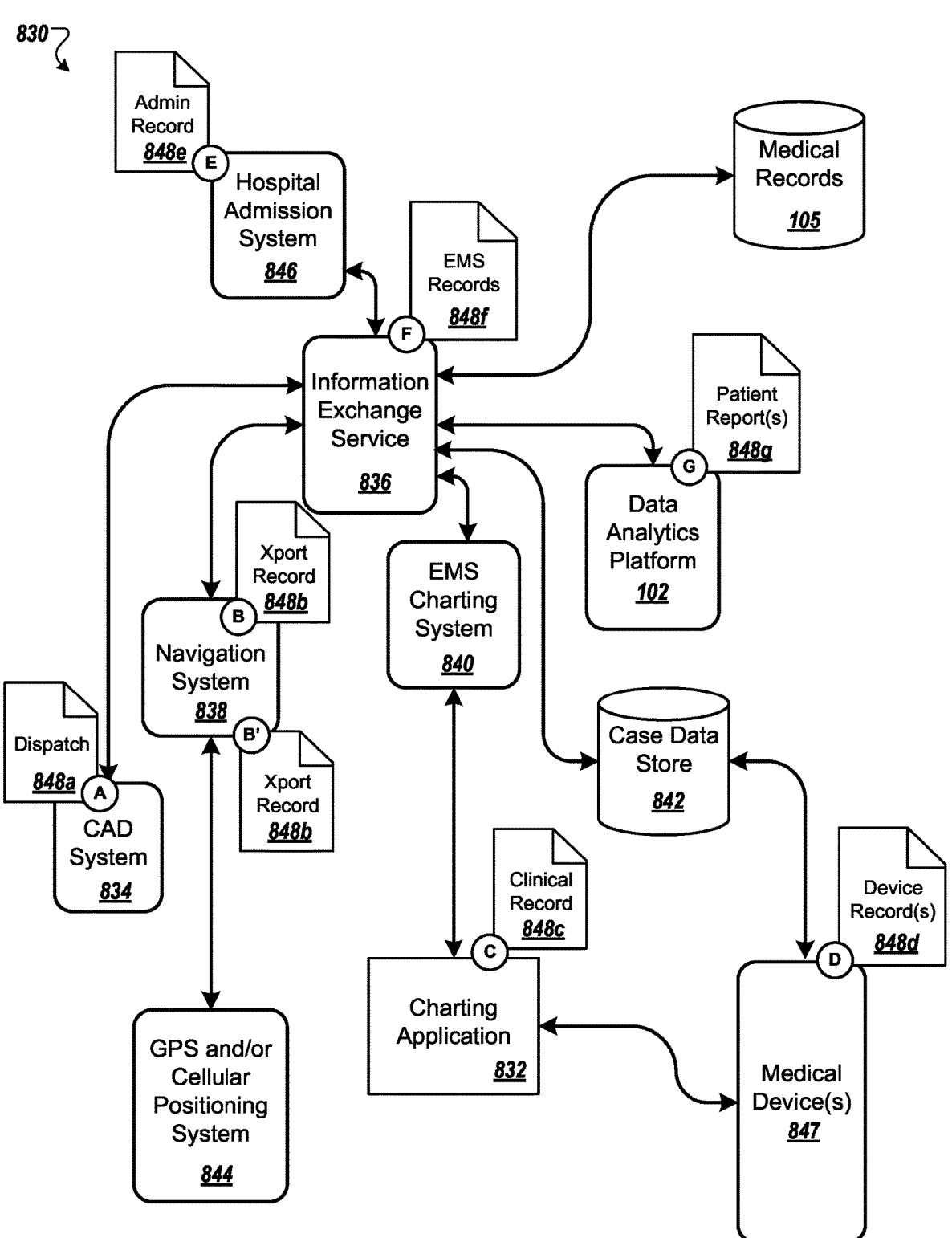
FIG. 8C is a block diagram of an example environment of medical systems accessible to the predictive analytics platform.

FIG. 7, FIG. 8A, and FIG. 8B present example patient reports. The reports, for example, may be generated by the patient report generation engine 278 of the predictive analytics platform 102, described in relation to FIG. 2. The reports of FIG. 7, FIG. 8A, and/or FIG. 8B, in some embodiments, are provided for review at a user portal, such as the claims and billing portal 110 and/or the reporting portal 111, e.g., as shown in FIGS. 1A and 1B.

Turning to FIG. 7, an example patient likelihood to pay report 700 presents a set of metrics 702a-c related to a patient likelihood to pay 704, an estimate of patient responsibility section 706, and a snapshot of recent patient statements 708. The patient likelihood to pay report 700 or portions thereof may be presented to a member of a service provider, in some examples, for use in making collections decisions and/or for use in assisting financial decisions when scheduling an elective procedure.

As illustrated in a top right region of the report 700, the patient likelihood to pay 704 has been deemed as high. The likelihood to pay, for example, may be characterized in two or more classifications such as, in some examples: high and low; high, medium, and low; or very likely, likely, somewhat likely, somewhat unlikely, unlikely, and very unlikely. In other embodiments, the likelihood to pay may be identified by a percentage likelihood or other quantile likelihood. The determination, for example, may have been made based at least in part on a credit score 702a (e.g., score value of "708") of the patient (or the responsible party, such as a parent or guardian), available credit to the patient or responsible party (e.g., $1,500), and/or the income of the patient or responsible party in comparison to the federal poverty level (FPL) 702c (e.g., 160%). The likelihood to pay 704 may be determined at least in part by the patient likelihood to pay engine 238, described in relation to FIG. 2. For example, the patient propensity to pay by medical debt level and/or credit score classifier(s) 190 may be invoked in determining the likelihood to pay 704.

Below the likelihood to pay and related metrics 702a-c, the estimate of patient responsibility section 706 includes a claim identifier 710, total charges 712 (e.g., $27,746.75), insurance/facility payments 714 (e.g., $350.00), adjustments 716 (e.g., $10,408.30), patient payments 718 (e.g., $0), and an amount of patient responsibility 720 (e.g., $16,988.45). The amount of patient responsibility, for example, may be applied by the patient likelihood to pay engine 238 of FIG. 2 in determining the likelihood to pay 704.

Turning to the set of patient statements 708 below the estimate of patient responsibility section 706, a statement balance 724a-c representing historic patient responsibility is associated with each statement 722a-c. In some embodiments, the unpaid balances 724a-c are applied by the patient likelihood to pay engine 238 of FIG. 2 in determining the likelihood to pay 704.

FIG. 8A illustrates an example of a patient report card 800 for personal health information and/or medical financial information. The report 800, for example, may be provided for access by a patient 802 for reviewing a history of financial, diagnostic, and procedural information related to the patient's medical history. The report 800, further, may provide the patient 802 with the ability to manage ongoing care. Thus, the patient report card 800 may provide a combination of payment, insurance, and clinical information in one aggregated report. In some implementations, the patient accesses the patient report card via a patient subscription service to the predictive analytics platform 102.

In various implementations, access to the patient report card is not limited to the patient such that and one or more of the patient, a healthcare administrator, or a healthcare provider may view the report card 800. The predictive analytics platform 102 may tailor the information in the patient report card 800 to the particular viewer. For example, a healthcare provider such as an emergency medical technician (EMT) in an ambulance crew may view the medical history for a patient but lack access to the financial information, including, for example, the patient's propensity to pay. However, as another example, a patient administrator at a hospital that is assisting a patient in selecting elective procedures may have access to this financial information to receive guidance from the platform 102 regarding patient financial support and various alternative treatments. By combining the clinical and the financial information, proposed alternative treatments may represent actionable data based on patient clinical history. In other words, the predictive analytics platform 102, in some embodiments, enables the patient to pick from clinically viable treatments with the benefit of financial information associated with those treatments. The predictive analytics platform 102, for example, may implement viewing restrictions via authentication procedures in an application programming interface (API) for the report card service. These authentication procedures may include authentication tokens that enable role-based permissions for various aspects of the patient report card 800.

The patient report card 800 may be useful in various scenarios. For example, one application may include selection of treatment options as described above. In another example, during pre-registration for various hospital procedures, deductible management, patient financial information as relevant, in some examples, for deductible payments, co-payments and other out-of-pocket expenses, as well as insurance coverage and clinical history, may enable a real-time and accurate customization of procedures and total costs. The clinical history or patient profile, in some embodiments, enables a prediction of which treatments or procedures may be the most effective based on the patient's medical history, which treatments or procedures may not be viable for the patient (e.g., eliminate possible treatments or procedures based on the patient's clinical history), and/or which treatments or procedures are optimal based both on financial information and the patient's clinical history. For example, in considering an elective procedure, a patient may be able to make an informed decision based both on medical financial information and their personal clinical situation. As yet another example, caregivers from an EMS crew or hospital emergency room may have a patient that is unconscious. The caregivers may find an identification like a driver's license or other identification in the patient's pocket or bag, allowing the caregivers to provide basic information such as name, date of birth, and possibly a driver's license number to the predictive analytics platform 102. The platform 102 may access the data universe 104 and generate, in real-time, a complete clinical history and financial profile for the patient including insurance coverage information. For example, in a clinically actionable time period (e.g., seconds or minutes), the caregivers may know that in the last ten years the patient has had two heart attacks, is currently taking a statin medication, has diabetes, has ABC health insurance with a primary physician Dr. Jones, and is able to pay for insured procedures but will be unlikely to afford an elective but not necessary procedure. With this real-time information, the caregivers can provide effective care to the patient without waiting for lengthy and expensive diagnostic tests that would merely reiterate information in the medical history. Additionally, the caregivers can avoid elective and costly procedures until the patient is able to make an informed decision. This provides an advantage of timely and effective treatment without undue financial burdens imposed on the patient.

In some implementations, the report 800 includes a personal information section 804 detailing basic personal information such as, in some examples, an age 804a (e.g., 48), a gender 804b (e.g., male), a height 804c (e.g., 5 feet 5 inches), a weight 804d (e.g., 167 pounds), and a primary insurance 804e (e.g., Insure National). In further examples, other personal information may include a billing address, a nationality/race, and/or a sexual identity. A review/update personal information control 818, when selected, may provide the patient 802 with the opportunity to update at least some of the personal information.

The report 800, in some implementations, includes a billing section 806 presenting information related to medical billing such as a deductible amount 820a, a copay amount 820b, an unpaid invoices control 820c, and an invoice history control 820d. The deductible amount 820a, in some embodiments, is a remaining deductible amount, for example generated in the manner described in relation to the remaining deductible 870 of FIG. 8B. In other embodiments, the deductible amount 820a is a deductible amount associated with the primary insurance 804e. The copay amount 820b, similarly, may be determined in a manner described in relation to the copay 872 of FIG. 8B. The unpaid invoices 820c, further, may be determined in a manner described in relation to the outstanding out-of-pocket expenses 884 described in relation to FIG. 8B, and the invoice history 820d may be derived in a manner similar to that described in relation to the paid claim expenses 882 of FIG. 8B.

The report 800, in some implementations, includes an appointments section 808 including a schedule now control 822a for scheduling an upcoming appointment (e.g., with one of the patient's health professionals 828b), an upcoming visits control 822b for accessing a list or calendar of scheduled medical appointments, a preventative treatments control 822c for reviewing vaccine appointments or other preventative medical appointments which may be performed out of office and/or without visiting a doctor or nurse practitioner, and a visit history control 822d for reviewing past visits with health professionals 828b. The information presented in the appointments section 808, for example, may have been collected from various service providers 208 of FIG. 2 by the predictive analytics platform 102.

In some implementations, the report 800 includes a medical history section 810 for reviewing medical history information regarding the patient 802. The medical history section 810, for example, may include various information commonly requested via health professional intake forms. At least a portion of the information accessible to the patient 802 via the medical history section 810, for example, may have been received by the predictive analytics platform 102 via one or more service providers 208 in response to the patient 802 filling out an intake form. In some implementations, at least a portion of the medical history section 810 was provided by the patient 802, for example through editing capabilities in the report 800.

In some implementations, the medical history section 810 includes a medications control 824a for accessing a list of current and/or past medications. Other prescribed and/or habitually ingested substances, in some embodiments, are included in the medications 824a such as, for example, vitamin and mineral supplements or other nutraceuticals.

The medical history section 810, in some implementations, includes an allergies control 824b for accessing a list of patient allergies. In addition to allergies, in some embodiments, the allergies control 824b may include one or more patient sensitivities, such as a sensitivity to artificial sweeteners.

A major surgeries control 824c of the medical history section 810, in some implementations, presents, upon selection, dates and information on various surgeries performed on the patient 802.

A conditions control 824d of the medical history section 810, in some implementations, presents, upon selection, chronic and/or current medical conditions of the patient 802. In some examples, chronic conditions can include lifetime conditions such as asthma, diabetes, a heart murmur, and/or blindness. The conditions, in some examples, can include birth defects such as, in some examples, deformities or blood disorders. In further examples, the conditions may include temporary conditions such as pregnancy.

The medical history section 810, in some implementations, includes a vaccinations control 824e for reviewing a listing of received preventatives (e.g., vaccines received, preventative medications, etc.) and/or preventative schedules (e.g., due dates for boosters or other vaccinations, recommended preventative vaccines or medications due to lifestyle or other considerations, such as antimalarials for travel, etc.).

In some implementations, the report 800 includes a health status section 812 for reviewing various metrics, levels, results, and/or other physiological measurements related to the patient 802. The health status section 812 may provide both current information as well as, in some embodiments, information regarding physiological data over time such that trends in physiological measurements may be monitored by the patient 802 and/or other users having access to the report 800 or portions thereof. The information in the health status section 812, for example, may have been received by the predictive analytics platform 102 via one or more service providers 208.

The health status section 812, in some implementations, includes a vitals control 826a for reviewing various vital physiological measurements such as, in some examples, blood pressure, blood oxygen level, body temperature, body mass index (BMI), heart rate, and/or respiration rate.

In some implementations, the health status section 812 includes a blood labs control 826b for reviewing various blood test measurements generated through laboratory testing. The blood labs control 826b, in some examples, may present information related to platelets, metabolic panels, lipid panels, and other blood screenings.

The health status section 812, in some implementations, includes a urine labs control 826c for reviewing various urine test measurements generated through laboratory testing. The urine labs control 826c, in some examples, may present information related to bacteria, microscopy, pH, glucose, protein, blood cell, and other urinalysis screenings.

Further, the health status section 812, in some implementations, includes a virus and/or infection tests control 826d for presenting results related to testing for viruses and/or infections. The virus and/or infection tests control 826d, in some examples, may present results related to influenza, SARS, covid, and other cold and flu testing, *streptococcus* testing, sexually transmitted disease testing, and/or intestinal parasite testing.

In some implementations, the health status section 812 includes an imaging control 826e selectable for reviewing imaging results such as, in some examples, x-ray, MRI, ultrasound, mammogram, and/or other medical imaging documents. Further, the imaging control 826e may include clinical summaries related to review and analysis of the contents of the images.

In some implementations, the report 800 includes a recent activity section 814, presenting recent additions and/or currently active information regarding the patient's medical care. The recent activity section 814, for example, may include a diagnoses control 828a configured to present to the reviewer information regarding any recent diagnostic results and/or diagnoses entered by one or more health professionals 828b. Further, the recent activity section 814 may include a health professionals control 828b to access information regarding the patient's current medical care (e.g., primary physician, preferred pharmacy, and/or specialty professionals such as, in some examples, oncologists, chiropractors, midwives, etc.). The recent activity section 814 may further include a messages control 828c configured, upon selection, to present messages related to the patient's health care, such as, in some examples, reminders of an upcoming appointment, an indication of pre-approval for a treatment requiring prior authorization, or access to recent documents (e.g., laboratory results, imaging, etc.).

Finally, in some implementations, the report 800 includes patient financial information 816. The patient financial information 816 may include all or a portion of the patient report card 850 for financial assistance and planning as shown in FIG. 8B.

The report 800, in some embodiments, may be provided in whole or in part to service providers, for example upon authorization of the patient 802. The authorization may be specific (e.g., on one occasion or at any time for a particular service provider) or general (e.g., to be provided to any of the health professionals 828b as needed). For example, upon being picked up by an emergency transport provider, the report 800 may be issued to emergency medical personnel to immediately recognize conditions, allergies, medications, and/or test results that may provide insight into the patient's present health concern and/or guide the emergency medical personnel in appropriately treating the patient 802 in the short term without inadvertently causing further complications, for example by supplying a medication listed in the allergies 824b. Further, the patient 802 may have access to the information in the report 800 to ensure completeness and accuracy of the information contained therein. For example, the patient 802 may have the opportunity to correct certain information in the report 800, such as when a value has been mistakenly entered into the health status 812 (e.g., height listed as 4 inches shorter than accurate, leading to an inaccurate BMI). Portions of the report 800, further, may be shared by the patient 802 or the health professionals 828b upon approval by the patient 802 with other organizations, such as a life insurance company in preparing a life insurance quote, an educational or day camp facility in accepting a new student/camper, and/or an assisted living facility accepting a new resident.

FIG. 8B illustrates an example patient report card 850 for patient financial assistance and planning. The patient report card 850, for example, may be utilized by a representative of a service provider while scheduling services for the patient. A portion of the information in the patient report card 850 may be generated responsive to the services scheduling engine 164 of the claims and billing platform 150 (see FIG. 1D).

The information presented in the patient report card 850 provides an overview of medical costs recently incurred and to-be-incurred by the patient. For example, as illustrated, the patient report 850 includes an insurance information section 852 detailing the patient's responsibilities under the listed insurance plan, a paid claim expenses section 854 listing claims amounts previously paid by the patient, an outstanding out-of-pocket expenses section 856 listing due and/or past due amounts owed by the patient for prior services, a treatment cost estimate section 858 providing costs and responsibility breakdown for the treatment being scheduled, an alternative treatment options section 860 listing other treatment options and associated costs.

Turning to the insurance information section 852, an insurance company 868 (e.g., "Smart Healthcare") is listed, along with a remaining deductible amount 870 (e.g., $300) and a copay amount 872 (e.g., $0.00). In some embodiments, the remaining deductible amount 870 is determined using the deductible estimation engine 220. For example, the remaining deductible amount 870 may be calculated in part through executing the method 300 of FIG. 3A. In further embodiments, the insurance information section 872 may include an indication of insurance plan, secondary insurance information, a renewal date, and/or a date the patient first became covered by the insurance company 868.

The paid claim expenses section 854 of the patient report card 850 includes a listing of historic claims amounts 882a-b remitted by the patient. The historic claims amounts 882a-b, for example, may be derived from the historic claims data 256 of FIG. 2 or the historic claims data 120 of the data universe 104. In some examples, the paid claims expenses section 854 may identify claims paid within a current calendar year, a current fiscal year, or the past X months (e.g., 1, 3, 6, 9, 16, etc.).

The outstanding out-of-pocket expenses 856 includes a listing of not yet paid claim amounts 884*a-b* as well as a total unpaid amount 886 ($620.51). The not yet paid claim amounts 884*a-b*, for example, may have been invoiced by the claims and billing platform 150. For example, the claim amount 884*a* indicates that an amount of $116.98 is overdue, while the claim amount 884*b* indicates that $503.53 is coming due for payment on February 16. The outstanding out-of-pocket expenses 856, in some embodiments, includes pending claims, for example derived from the incomplete claims 642 as discussed in relation to FIG. 6C. For example, the claims and billing platform 150 may store and have access to in-process claims, and the patient report generation engine 168 may access the pending claims data to determine other expenses for which the patient will be responsible in an upcoming invoice.

The treatment cost estimate section 858 includes an inpatient stay cost 874 for the treatment (e.g., $12,354.38), a patient responsibility portion 876 (e.g., $450.72) of the inpatient stay cost 874, an insurance responsibility portion 878 (e.g., $3,851.29) of the inpatient stay cost 874, and an estimated payment 880 (e.g., $4,302.01) anticipated to be remitted to the service provider. The patient responsibility portion 876 may take into consideration the remaining deductible 870 of $300 and/or the copay 872 of $0. In some embodiments, the estimated payment 880 is determined at least in part through invoking the payer payment pattern engine 232 and/or the patient payment pattern engine 234 of FIG. 2. For example, the payment pattern application engine 236 of FIG. 2 may apply output of the payer payment pattern engine 232 and/or the patient payment pattern engine 234 to calculate the estimated payment 880. Further, in some embodiments, a confidence level or rating 863 associated with the estimated payment and provided by the patient payment pattern engine 234 may be noted in the patient report card 850.

The alternative treatment options section 860 lists cost and a responsibility breakdown for payment for alternative treatment options 888*a-b*. The alternative treatment options 860, in some examples, may include alternative procedures, alternative equipment, and/or alternative post procedure care. In some embodiments, each of the options 888*a*, 888*b* are selectable via the patient report card 850 to review a detailed synopsis of the alternative to the presented treatment as illustrated in the treatment cost estimate section 858 and the treatment parameters section 862.

Turning to the treatment parameters section 862, in some implementations, the treatment may include certain pre-requisites, post-requisites, or other influencing factors related to the procedure. For example, as illustrated, the proposed treatment involves a pre-authorization prerequisite 890, a length of stay 892 (e.g., inpatient, overnight, number of days, etc.), and a pre-qualification prerequisite 894 (e.g., blood screening, urine screening, fasting, pre-operation prescription, pre-operation procedure, etc.). The treatment parameters section 862, while not necessarily touching upon financial matters, will give the patient an idea of the scope of the treatment, which may impact the patient's ability to attend work and/or perform other activities. Regarding the pre-authorization prerequisite 890, "obtained" is listed. For example, during scheduling, the services scheduling engine 164 of the claims and billing platform 150 may automatically request pre-approval, for example through the payer pre-approval request engine 226 of the predictive analytics platform 102, as discussed in relation to FIG. 2.

In some implementations, the report 850 includes the patient financial rating 864, representing an overall financial score related to the ability of the patient to cover the out-of-pocket expenses 886 as well as the patient responsibility 876. The patient financial rating 864, in some embodiments, is calculated using the patient financial rating engine 282, described in relation to FIG. 2. As illustrated, the patient financial rating 864 is a grade "B."

The report 850, in some implementations, includes a financial support options control 866 configured to, when selected, present opportunities for accessing additional financing for the treatment. In some examples, the opportunities may include federal programs, state programs, charitable foundation programs, and/or foundation discount programs. Further, the opportunities may include credit options such as a medical credit card and/or loan opportunity. The assistance availability analysis engine 280 of FIG. 2, for example, may be used to generate at least a portion of the financial support options.

In various implementations, the patient report cards 800 and/or 850 may be available to a patient at a reporting portal 111 (e.g., as shown in FIG. 1A). In some implementations, the reporting portal 111 is presented at a mobile device such as a smartphone or tablet. For example, the patient may access the report cards 800 or 850 via a website or smart device application either on demand or as part of a subscription service.

In some implementations, the patient can monitor the report card 800 or 850 and/or the report card 800 or 850 may flag issues for remediation by the patient. For example, the platform 102 may automatically flag discrepancies in the clinical and/or financial information and may provide a user interface for real-time corrections by the patient and/or for the patient to access (e.g., via a chat or email conference) an appropriate health care advisor to correct patient records. The reporting portal 111 may enable the patient to flag issues in their report card in order to remediate these issues before they pose a problem for the patient either clinically or financially.

In some implementations, the predictive analytics platform 102 provides automated monitoring of report card access to generate an automated alert to a patient that an entity has accessed their patient report card 800 or 850. Additionally or alternatively, the predictive analytics platform 102 may generate an automatic alert that patient information like insurance, demographics, or clinical information has changed. The predictive analytics platform 102 may also automatically update the report card 800 or 850 in response to changes in these types of patient data.

In some implementations, the predictive analytics platform 102 links the patient report card 800 and/or 850 to a communications link. For example, the communications link may enable an automated call or text message to emergency contacts along with an access code for all or a portion of the patient report card 800 or 850 so that the patient report card 800 or 850 may be available to patient contacts or preferred medical personnel in response to a 911 call or an accident, such as a fall detected by a smartphone.

In some implementations, the predictive analytics platform 102 is configured to access medical device data 127 in the data universe 104 to trigger generation of or communication of the patient report card 800 and/or 850. For example, if a patient is connected to a defibrillator or a ventilator, the predictive analytics platform 102 may receive a notification regarding this connection via the medical device data 127 (e.g., data reported by the medical device) and prompt an automated communication of the patient report card 800 and/or 850 to one or more of the patient, caregivers, contacts, etc.

In some implementations, the various means of communications of the patient report card 800 and/or 850 may be automated by the predictive analytics platform 102 responsive to changes in the data universe 104 corresponding to the particular patient. For example, the predictive analytics platform 102 may be trained to recognize categories of events indicated by the data in the data universe 104 that trigger a need for the generation and/or communication of the patient report card 800 and/or 850. Furthermore, the predictive analytics platform 102 may curate the contents of the patient report card 800 and/or 850 based on a predicted relevance of those contents to particular recipients based on the category of event. These changes in the data universe 104 may thus trigger an automated send operation by the predictive analytics platform 102 of the patient report card 800 and/or 850 to a recipient predicted with a threshold level of certainty to need access to the report 800 and/or 850. In this manner, the predictive analytics platform 102 may automatically and dynamically generate and/or trigger the communication of the patient report card 800 and/or 850. The predictive analytics platform 102 may predict the level of importance of a particular event and only trigger these automated activities for certain thresholds of importance. In this manner, the predictive analytics platform 102 may control and trigger the movement of patient information from point to point within the healthcare system to facilitate effective and timely care for the patient.

FIG. 8C illustrates an example environment 830 of medical systems accessible to the predictive analytics platform 102. The medical systems may include a computer aided dispatch system 834, a navigation system 838, an EMS charting system 840, a case data store 842, and the medical record repository 105. The navigation system 838 may be communicatively coupled to a positioning system 844 (e.g., GPS and/or cellular positioning), the charting system 840 may be communicatively couple to a charting application 832, and the case data store may be communicatively coupled to the medical devices 847. The medical devices 847 may also be communicatively coupled to the charting application 832.

In some implementations, an information exchange service 836 (e.g., a health information exchange) enables communications between the various endpoints shown in FIG. 8C. In an example scenario 848, an emergency event occurs, such as a cardiac arrest. The CAD system 834 dispatches 848a an EMS crew to the scene, the navigation system 838 records 848b transport information to the scene and to a patient disposition site like a hospital, and a clinical record 848c for the event is created by the charting application 832 and stored in the charting system 840. Additionally, medical device records 848d are stored in the case data store 842. When the patient is delivered to the hospital, the emergency room creates an administrative record 848e to admit the patient. Upon creation of this record, a hospital admission system 846 generates a call to the exchange service 836 to receive EMS records 848f including the medical device records 848d and the EMS clinical record 848c for the patient. The EMS records 848f may include the dispatch information 848a and/or the transportation record 848b as provided to the charting system 840 from the dispatch 834 and navigation 838 systems through the information exchange service 836. The initial dispatch from the CAD service 834 and/or the call to the exchange service 836 by the hospital may trigger a call to the predictive analytics platform 102 for generation and communication of a patient report card 800 of FIG. 8A and/or report card 850 of FIG. 8B. The predictive analytics platform 102 may provide patient reports 848g including the patient report card 800 and/or the patient report card 850 to one or more of the EMS crew and/or the hospital emergency room via the exchange service 836. Because the predictive analytics platform 102 may access the various entities in FIG. 8C through the exchange service 836, the patient report card 800 and/or 850 may include information from one or more of these entities and/or may be provided to one or more of these entities. This creates a real-time connectivity across the healthcare spectrum that enhances and improves timely care and tracking of outcomes that can improve healthcare delivery.

FIG. 9 illustrates an example provider score card 900 presenting financial metrics corresponding to a provider 902 (e.g., "Neighborhood Medical Center") in comparison with peer providers. Further, the provider 902 is provided with a provider rating 904 related to the results of the comparisons. The provider score card 900, for example, may be shared with the service providers 208 by the predictive analytics platform 102 (e.g., via the patient report generation engine 278 or the provider report generation engine 286 of FIG. 2).

As illustrated, the provider score card 900 includes various metrics categories, such as an accounts receivables section 912, a payments section 914, an adjustments section 916, an estimated payments section 920, an account balance section 922, a days revenue outstanding section 924, and a number of transports section 926. The sections 912 through 924, in some embodiments, are based at least in part on a type of service provider. For example, the number of transports section 926 may be applicable to a medical transport provider or service provider having in-house medical transportation services. Other metrics categories, in some examples, may include quality of care metrics and/or customer satisfaction metrics. Each of the sections 912 through 924, as illustrated, include a set of metrics including subject organization metrics 906 (e.g., the service provider 902), national average metrics 908, and regional average metrics 910. The national average metrics 908 and regional average metrics 910, in some examples, are each based upon a collection of organizations similar to the provider 902. For example, if the provider 902 is a medical transportation provider, then the national average metrics 908 and the regional average metrics 910 are derived from financial details of other medical transportation providers. In some implementations, the national average metrics 908 and regional average metrics 910 are generated based upon sets of peer organizations identified using the provider peer identification engine 274, described in relation to FIG. 2. Further, although the comparison metrics are based upon national and regional groupings of peer service providers, in other embodiments, different breakdowns may be presented such as, in some examples, state average, province average, and/or county average.

In some implementations, at least a portion of the sections 912 through 926 are selectable to expose a greater level of detail. For example, as illustrated in the days revenue outstanding section 924, the days may be broken down by a dimension of payer type 928, illustrated as a commercial payer type 928a, a government payer type 928b, and a self-pay payer type 928c. Additional dimensions, in some examples, may include a date/time dimension (e.g., quarterly, end of year, end of fiscal year, monthly, etc.), an operations base location dimension (e.g., for a multi-site provider 902), a vehicle type dimension and/or a clinical nature of transport dimension (e.g., for the number of transports section 926), a level of service dimension (e.g., in the case of a transport service provider—advanced life support (ALS), basic life support (BLS), special care transport (SCT), etc.), a mode of care dimension, a quality of care dimension, a customer satisfaction dimension, a claims submission type dimension, and/or a contracted vs. non-contracted dimension.

Turning to a bottom section of the report 900, in some implementations, one or more controls 926 may be provided to filter or otherwise manipulate the metrics presented in the report 900. For example, a timeframe drop-down menu 926a, when selected, may provide the user with the opportunity to filter the metrics according to a selected timeframe. An aggregation drop-down menu 926b, when selected, may provide the user with the ability to select an aggregation style for generating the presented metrics. The aggregation styles, in some examples, may include sum, average, count, minimum, and/or maximum. Further, a location drop-down menu 926c, when selected may provide the user with location options for narrowing the results. The location, in some examples, may refer to a delivery location in the circumstance of a transport service provider, an operational location in the circumstance of a multi-site service provider, and/or a service provision location in the circumstance of a mobile service provider.

In some implementations, the metrics presented in the provider report 900 contribute to the overall provider score 904 (e.g., "A+"). The provider score, in some embodiments, is generated at least in part by the provider financial rating engine 284, as described in relation to FIG. 2. In some embodiments, the provider score 904 takes into consideration further metrics dimensions such as, in some examples, compliance, documentation practices, clean claims, closest appropriate facility, prior authorization, payment predictability, timely filing, commercial payer contracts, facility contracts, debt setoff programs, National Emergency Medical Services Information System (NEMSIS) to reimbursement correlation, days revenue outstanding (DRO) rolling average, and/or a claims pipeline. A portion of the above-noted dimensions, in some embodiments, are generated through analysis of historic service provider data 122 by the predictive analytics platform 102 (see, for example, FIG. 1A).

The service provider 902 may access the provider report 900 to determine areas in which the organization excels in comparison to peers as well as areas of potential growth. The service provider report 900, for example, may consider adding services and/or shifting focus on particular services (e.g., contracted versus non-contracted) to improve revenue. In another example, the service provider 902 may access the provider report 900 to identify improvements within the organization over time. The improvements, for example, may include quality improvements, increases in revenue stream, and/or overall growth of business. In an illustrative example, the service provider 902 may realize that shortening the days revenue outstanding 924 to be closer in line with peer organizations may improve cash flow and overall revenue in the business.

FIG. 10 illustrates an example projected revenue report 1000 for a provider, such as the service provider 902 of FIG. 9. The projected revenue report 1000, for example, may include metrics derived by the projected revenue analysis engine 272 of FIG. 2 to forecast upcoming income likely to be paid to the service provider based on anticipated claims, pending claims, and/or outstanding invoices and further based upon anticipated timing and portion of the outstanding reimbursements that are likely to be actualized. Further details regarding determining projected revenues are described in U.S. Patent Application Publication No. 2022/0309592 to Zahora et al., incorporated by reference herein in its entirety.

In some implementations, the projected revenue report 1000 includes a total average claim payment section 1002, an average claim payment by payer section 1004, and an average claim payment by payer and by policy 1006. These breakdowns in remittance analysis, for example, may provide the service provider with an understanding of where payments are derived from, both at the payer level and at the policy type level. The metrics presented in the projected revenue report 1000, in some examples, may represent a future timeframe of end of month, within the next 30 days, within the next 60 days, or within the next 90 days.

Turning to the total average claim payment section 1002, an overall claim count to be reimbursed 1008 (e.g., 8), an average claim payment anticipated 1010 (e.g., $1,258.53), and a total payments anticipated 1012 (e.g., $10,068.22) are presented, providing a synopsis of anticipated income for the service provider.

Below the total average claim payment section 1002, the average claim payment by payer section 1004 breaks down the summary provided in the total average claim payment section 1002 by payers 1020a-d. For each of the payers 1020a-d, a claim count 1014, an average anticipated claim payment 1016, and a total payments anticipated 1018 are presented.

Finally, the information is broken down further in the average claim payment by policy description 1022 (e.g., commercial, facility, Medicare, etc.) in the average claim payment by payer and by policy section 1006. The average claim payment by payer and by policy section 1006 additionally includes a breakdown, per payer 1020, by claim count 1024, average claim payment 1026, and total payments 1028.

Figure 11A:
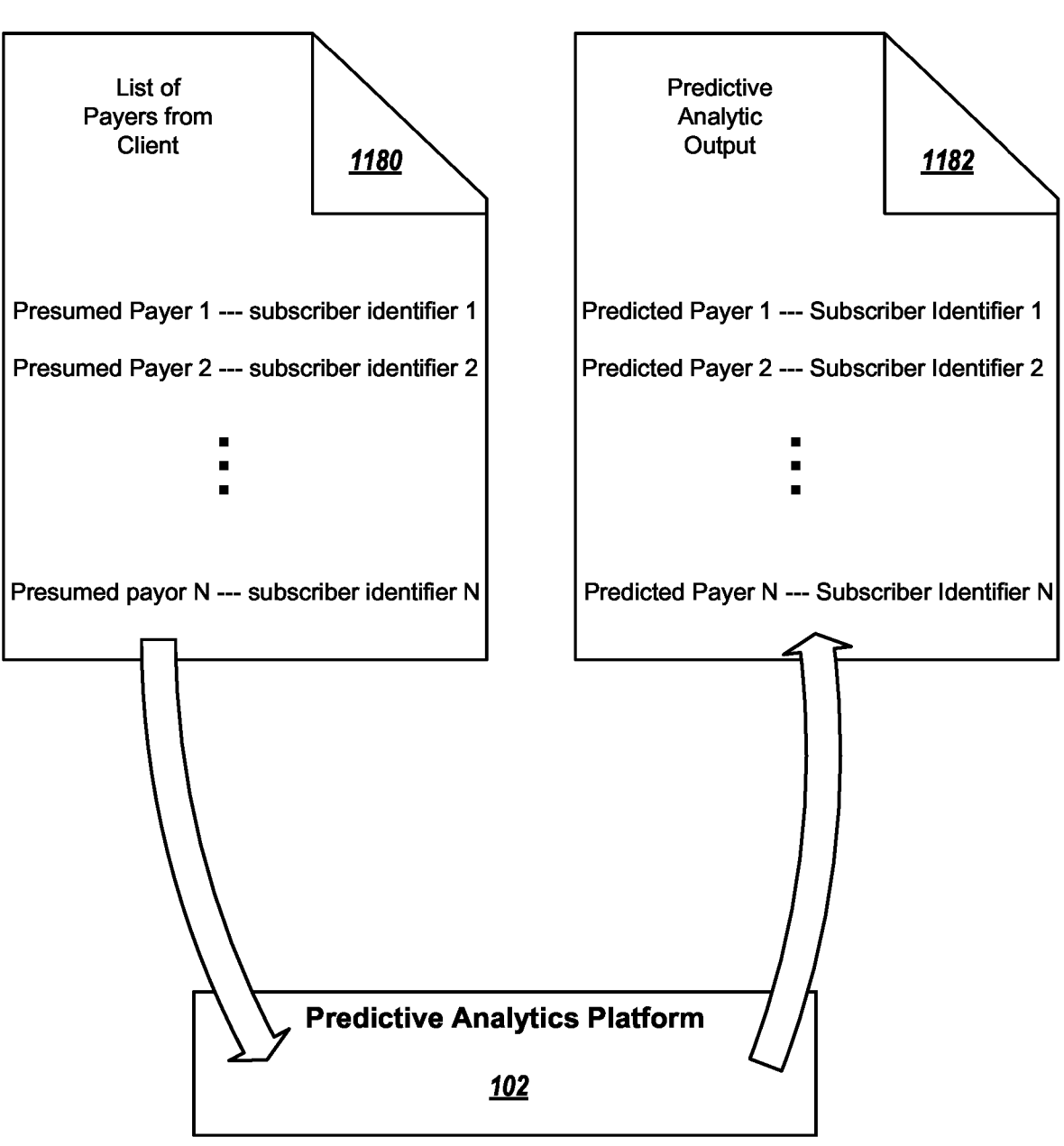
FIG. 11A, FIG. 11B, and FIG. 11C illustrate flow diagrams of example processes for automatically identifying likely payers based on subscriber identifiers.
Figure 11B:
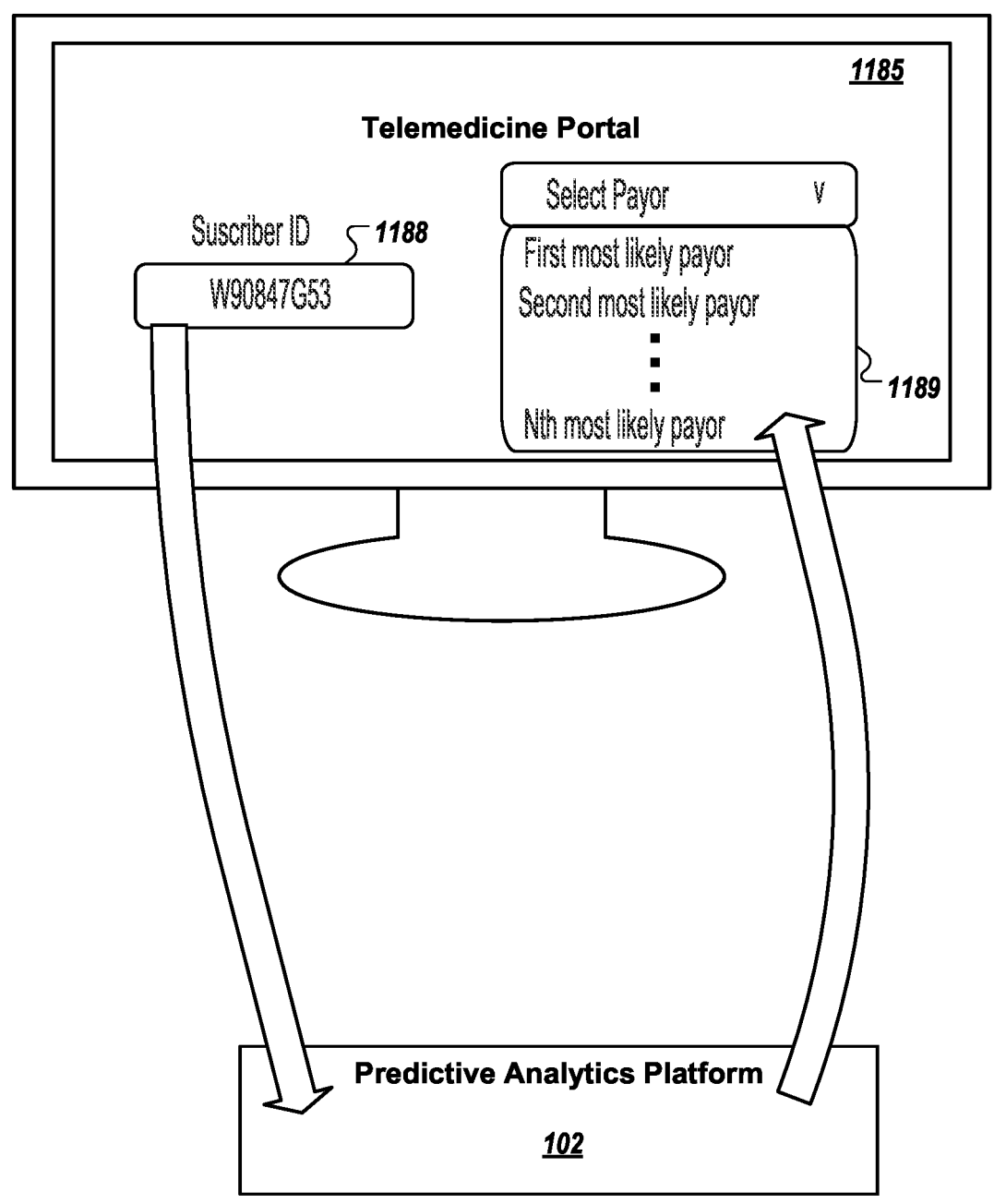
Figure 11C:
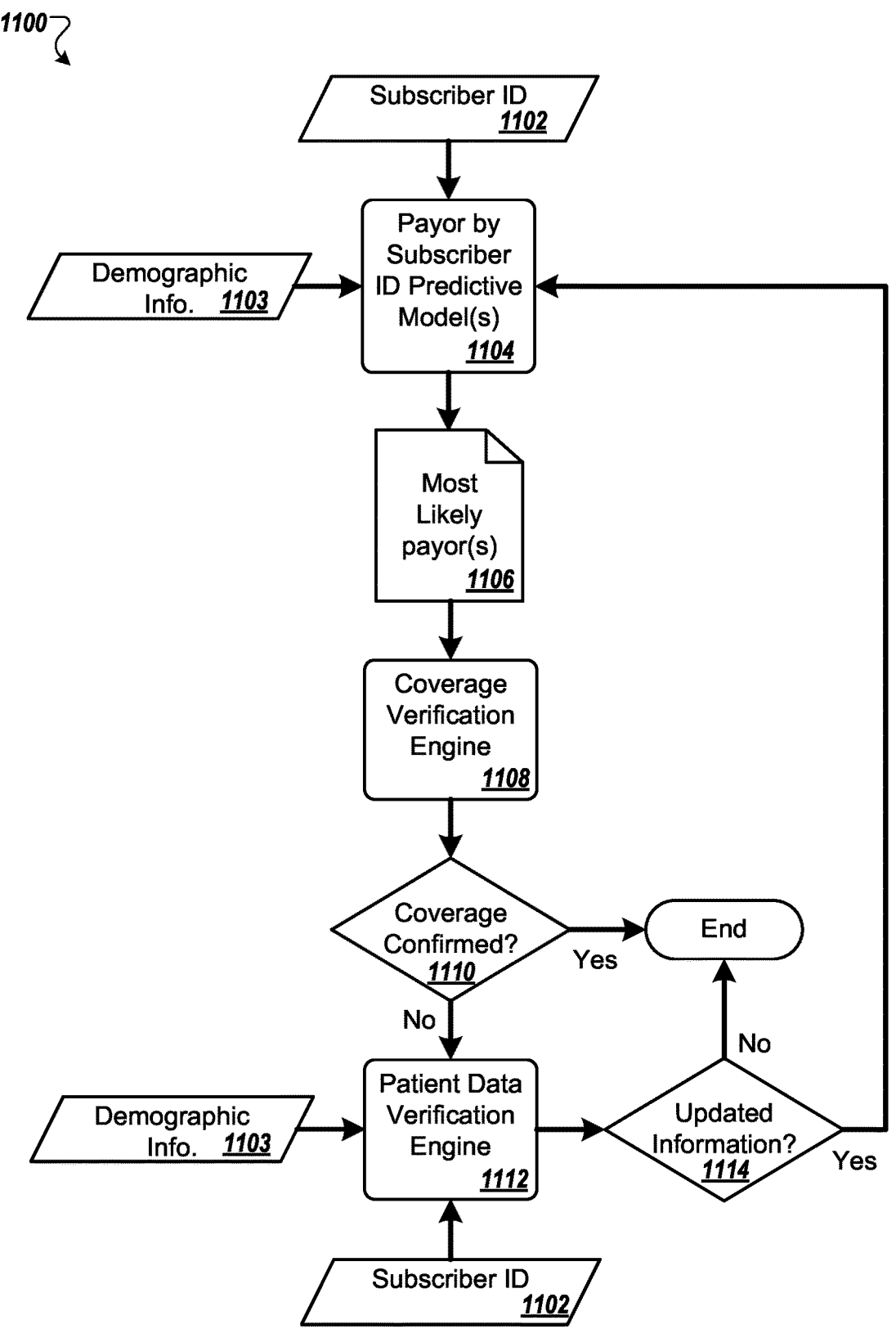

Turning to FIGS. 11A, 11B, and 11C, in some implementations, a process 1100 identifies a most likely payer or set of most likely payers based on a payer subscriber identification number (i.e., a subscriber id or subscriber identifier) using trained machine learning models. For example, the payer identification engine 218 of the predictive analytics platform 102 of FIG. 2 may execute the process 1100. A subscriber to a payer is a person entitled to receive payments from the payer as reimbursement for medical services or have payments disbursed on their behalf from the payer to the provider of medical services. When subscriber information is provided in a medical claim, the information usually includes a subscriber ID and a name of a payer. However, the name of the payer is often inaccurate or in error. For example, a claim may list a payer as "BlueCross" when the actual payer is "BlueCross Ohio." As another example, a claim may list a payer as "BlueCross Ohio" when the actual payer is BlueCross Pennsylvania." As a further example, a claim may list a payer as "Medicaid" when the actual payer is a subsidiary program of Medicaid such as "CareSource." When the payer is listed incorrectly, this may result in a denial or substantial delay in claim reimbursement. Subscriber identification numbers (subscriber IDs) correspond to the payer. However, due at least in part to the non-centralized nature of health insurance and other insurance in the United States, the quantity and variation of subscriber IDs is vast and there is not a centrally coordinated system providing a one-to-one unique correspondence between subscriber ID and the insurance payer. This is particularly problematic when a medical provider deals with hundreds or thousands of different payers and a multitude of associated subscriber IDs. Additionally, the payers and the subscriber IDs are subject to change over time and therefore any correlations need to be periodically rechecked and updated.

The process 1100 may apply to a variety of situations. For example, as illustrated in FIG. 11A the predictive analytics platform 102 may obtain a list of payers 1180 (e.g., a first list of payers). For example, the list may include up to 100, 200, 500, 1000, 2000, 5000, 10,000, or 20,000 payers, from a client, i.e., a recipient of services from the predictive analytics platform 102 (e.g., a medical practice, a hospital, a clinic, an EMS agency, or other patient services provider). The list 1180 may also include subscriber IDs for each of the presumed payers on the client list. The presumed payers may be those identified by a patient or by office personnel at the client but may or may not be accurate. Based on the data universe 104, the predictive analytics platform 102 may generate a list of payers (e.g., a second list of payers 1182) predicted to correspond to the subscriber identifiers provided by the client. The list 1182, in some embodiments, includes a confidence level or rating associated with each payer of the one or more payers. For example, a percentage confidence level may be provided. The payers are ranked, in some embodiments, in relation to likelihood of match. In order to provide payer based data from the predictive analytics platform 102 to the client, the predictive analytics platform 102 may need to reconcile the client list 1180 with the list 1182 generated by the platform 102 and identify the most likely predicted payer based on the subscriber identifier. This reconciliation process may require a mapping operation by the payer identification engine 218 of FIG. 2 in which each subscriber ID and presumed payer in the client list is associated with a predicted payer according to the process 1100 and the predicted payer is automatically mapped to a payer in the list retained by the platform. Thus, the payer identification engine 218, in some embodiments, generates a correlation map between subscriber IDs from a client and payers available to the predictive analytics platform 102. Additionally, the payer identification engine 218, in some embodiments, automatically updates the correlation map when subscriber ID formats change and/or payers are added or dropped.

As another example, the predictive analytics platform 102 may provide the subscriber identification process 1100 as part of a telemedicine registration program. In such an implementation, as illustrated in FIG. 11B, a user of the program may merely enter their subscriber identification code 1188 at a telemedicine registration portal 1185. The subscriber identification process 1100 may provide a drop down menu 1189 of possible payers or assign a payer and request verification where the choices on the drop down menu or the assigned payer are identified by the predictive analytics platform 102. Such a process may replace entry of payer information by the patient or subscriber, for example, by copying or providing an image of an insurance card. Without this, a drop down list of all the possible payers for a telemedicine service with wide geographic reach would include thousands of choices and still be subject to human error in properly selecting a payer.

As an additional example, the predictive analytics platform 102 may execute the process 1100 during a patient registration routine where an entered payer fails confirmation due to incorrect information entered by a patient or medical provider professional. In another example, the process 1100 may be invoked as part of patient intake software to assist the patient or a medical provider professional in selecting the correct corresponding payer by refining selection options (e.g., via a drop-down menu) to a set of most likely matching payers. In a further example, the process

1100 may be invoked during a bulk registration routine, such as the registering of patients of a particular medical practice with a new software package the medical practice is integrating into its medical invoicing and/or claims processes.

In some implementations, the process 1100 begins with at least one subscriber identifier 1102 being obtained by the predictive analytics platform 102 for use in matching the identified subscriber to a corresponding payer. In some implementations, at least one payer by subscriber identifier predictive model 1104 analyzes the subscriber identifier 1102 to determine one or more most likely payers 1106 based at least in part on the subscriber identifier 1102. The one or more most likely payers 1106, in some embodiments, includes a confidence level or rating associated with each payer of the one or more payers. For example, a percentage confidence level may be provided. In some embodiments, the payers are ranked in relation to likelihood of match. A number of payers determined by the payer by subscriber identifier predictive model(s) 1104, in some embodiments, is fixed at a set number or capped at a threshold number of candidate payers (e.g., less than ten, up to five, up to three, two, etc.). In some embodiments, the number of payers determined by the payer by subscriber identifier predictive model(s) 1104 is determined at least in part on a threshold confidence (e.g., at least 85% likelihood, at least 90% likelihood, etc.).

In some implementations, at least a portion of the payer by subscriber identifier predictive model(s) 1104 analyzes the subscriber identifier 1102 further based on demographic information 1103. The demographic information 1103, in some examples, may include a geographic region (e.g., address or portion of an address) of the subscriber and/or a geographic region of an employer of the subscriber. Subscriber identifiers 1102, for example, may vary based on location, so including the geographic region(s) most likely matching the subscriber's insurance plan can assist in narrowing the candidate list and increasing accuracy of results. In another example, the demographic information 1103 may include an age of the subscriber, an employment status of the subscriber, and/or a disability status of the subscriber to determine whether the subscriber identifier 1102 is more likely than not associated with a payer that functions outside of employment coverage, such as Medicaid and/or Medicare. In a further example, the demographic information 1103 may include an employer type of the subscriber. The employer type, in illustration, can be used to match a set of most likely payers associated with local government, federal government, and/or military employees in comparison to most likely payers associated with privately employed subscribers, most likely payers associated with fulltime postsecondary education students, and/or most likely payers associated with self-employed subscribers. It is important to note that, in some embodiments, the subscriber demographics may be indicative of a covered individual (e.g., the employee) rather than the patient being registered (e.g., a family member). Further, the demographic information 1103, in some embodiments, is generic to a batch registration such that it provides information regarding a provider (e.g., address, type of facility that may be indicative of geriatric care and/or military personnel care, etc.) rather than information regarding a particular subscriber.

In some implementations, the list of most likely payers 1106 is obtained by a coverage verification engine 1108. The coverage verification engine 1108, for example, may perform operations described in relation to the coverage verification engine 216 of FIG. 2. In some embodiments, the coverage verification engine 1108 performs operations in real-time such that, as mentioned above, the correct subscriber information is entered into the system at the time of patient registration. If coverage is confirmed (1110), the process 1100 ends. For example, the process 1100 may return payer information (e.g., a confirmed payer identifier) for application by a calling software system and/or its end user.

If coverage fails to be confirmed (1110), in some implementations, the subscriber identifier 1102 and demographic information 1103 are provided to a patient data verification engine 1112. The patient data verification engine 1112, for example, may perform operations described in relation to the patient data verification engine 214 of FIG. 2. The patient data verification engine 1112, for example, may identify an alternative subscriber identifier and/or portion of demographic information for use by the subscriber identifier predictive model(s) 1104. If updated information is available (1114), the process 1100 may be repeated. If not, the process (1100) may end. For example, rather than returning payer information for application by a calling software system and/or its end user, the process 1100 may return an error code.

Although described as a particular series of operations, in some embodiments, more or fewer steps may be included in the process 1100. For example, rather than verifying coverage, the set of most likely payers 1106 may be returned to a calling application, for example for inclusion in a drop-down menu for user selection. In further embodiments, certain steps of the process 1100 may be performed in a different order or in parallel. For example, the incoming subscriber identifier 1102 and demographic information 1103 may be immediately analyzed by the patient data verification engine 1112 to supplement the supplied information with any known information available to the system. Other modifications of the process 1100 are possible.

Figure 11D:
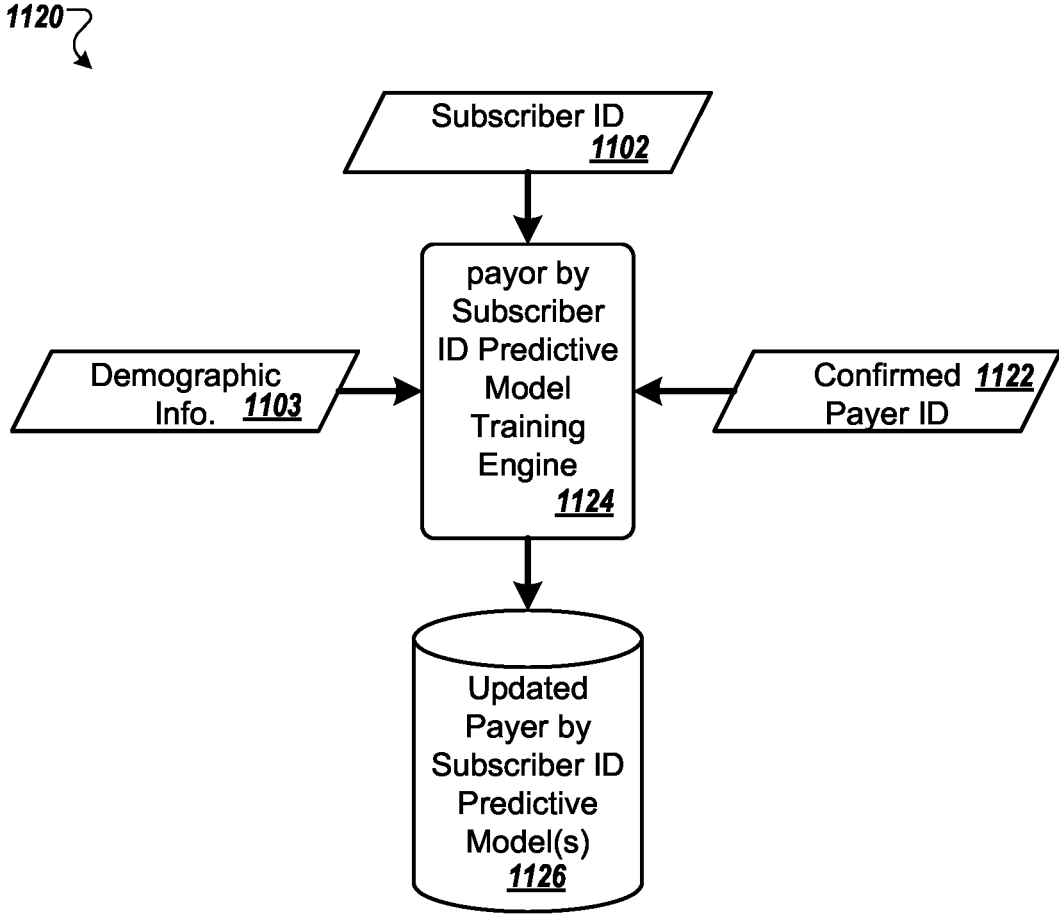

FIG. 11D illustrates a process 1120 for updating the training of the payer by subscriber ID predictive model(s) 1104. New truth data in the form of the subscriber identifier 1102, the demographic information 1103, and a corresponding confirmed payer identifier 1122 may be collected from the process 1100 for use by a payer by subscriber ID predictive model training engine 1124 for updating training models. In this manner, as payers allocate additional sets of subscriber identifiers, the subscriber identifier patterns continue to be recognized by the process 1100. The training, in some embodiments, may include negative truth data as well as positive truth data. For example, subscriber identifiers 1102 that failed to be verified with one or more of the most likely payers 1106 identified by the payer by subscriber ID predictive model(s) 1104 may be provided, along with the failed payer(s), to the process 1120 to make incorrect matches less likely in the future.

In some implementations, the payer by subscriber identifier predictive model training engine 1124 stores one or more updated payer by subscriber identifier predictive models 1126.

The process 1120 may be performed on an ongoing basis to continually train the model(s) 1104 used by the process 1100 of FIG. 11A in near real-time. In other embodiments, truth data sets may be collected from repeated executions of the process 1100 for use on a periodic basis by the process 1120.

Referring to FIG. 12, the machine learning models may be trained using subscriber identifier patterns indicative of a particular payer's allocated subscriber identifiers. A set of truth data used to train the machine learning models, for example, may include known subscriber identifiers and corresponding confirmed payer identifiers. Further, the subscriber identifier patterns may be trained based on demographic information such as a geographic region. For example, certain payers operating over a wide geographic region may have subscriber identifiers including alphanumeric coding indicative of a patient's geographic region. In this circumstance, a patient's geographic area may be used to fine-tune the analysis of the subscriber identifier.

FIG. 12 illustrates a flow diagram of an example process 1200 for training machine learning models and deriving combined data models directed to predicting the identity of payers based on subscriber identification format.

In some implementations, the process 1200 begins with accessing subscriber identifiers 1204a and corresponding payer identifiers 1204b from a storage region 1202. The subscriber identifiers 1204a (e.g., numeric or alphanumeric member identification codes) and corresponding payer identifiers 1204b (e.g., names, identification codes, etc.), for example, may be accessed from the data universe 104 of FIG. 1A. The subscriber identifiers 1204a and corresponding payer identifiers 1204b, for example, may be stored as part of patient records represented by the patient data 240 of FIG. 2 (e.g., in the data repository 210). Although described in relation to a one-to-one relationship between subscriber identifier 1204a and payer identifier 1204b, in some embodiments, the payer identifiers 1204b include hierarchical payer information (e.g., a national parent company identification as well as one or more regional payer identifications for each region (e.g., state, municipality) in which the national parent company provides coverage), such as, in an illustrative example, Acme Insurance of New England, Acme Insurance of California, and Acme Insurance of Ohio.

In some implementations, the subscriber identifiers 1204a and corresponding payer identifiers 1204b are provided to a first learning model training engine 1208a to train a learning model 1210a to recognize patterns of subscriber identifiers 1204a corresponding to each payer represented by the payer identifiers 1204b. The patterns, for example, may include a total number of characters, a position of a series of alphabetic characters in relation to numeric characters within a given subscriber identifier, use of non-alphanumeric characters, and/or other patterns that may be used to characterize a certain payer's subscriber identifiers.

The first learning model training engine 1208a, in some embodiments, includes a decision tree learning model algorithm such as a random forest model algorithm to classify subscriber identifiers as belonging to a given payer among a set of payers. The decision tree learning model algorithms, for example, provide strong accuracy on data sets appropriate to supervised learning (e.g., pre-matched known truth data). In some embodiments, the first learning model training engine 1208a includes neural network-based analysis for categorizing subscriber identifiers by payers based on patterns within the subscriber identifiers, such as a recurrent neural network (RNN). The RNN, for example, may receive additional patient information, such as geographical region, age, sex, employer, etc. to identify subscriber patterns used to code the additional patient data. Other learning model algorithms and/or neural network-based analysis tools may be applied to train the learning model 1210b.

The patient records supplying the subscriber identifiers 1204a and payer identifiers 1204b, in some embodiments, include an unbalanced set of data, including records primarily representative of one to a handful of very large payers with a minority of the data representing smaller insurers. In such a circumstance, in some implementations, a data balancing engine 1206 evens the numbers of records of matched subscriber identifiers 1204a and payer identifiers 1204b to promote the learning of subscriber identifiers 1204a related to less popular payers. The data balancing engine 1206, for example, may undersample the data related to popular payers or oversample data to create copies of records related to the less popular payers.

In some implementations, the balanced set of the subscriber identifiers 1204a and corresponding payer identifiers 1204b are provided to a second learning model training engine 1208b to train a learning model 1210b to recognize patterns of subscriber identifiers 1204a corresponding to each payer represented by the payer identifiers 1204b. As described in relation to the learning model training engine 1208b, a variety of machine learning algorithms and/or deep learning analysis networks may be used to train the balanced learning model 1210b.

In some implementations, the balanced learning model 1210b is combined with the first (e.g., unbalanced) learning model 1210a by a data model combining engine 1208c to create a payer by subscriber ID format predictive model 1210c for matching a given subscriber identifier with a corresponding payer. The predictive model 1210c, in some embodiments, provides one or more likely payers based on a given subscriber identifier, where the payers are identified in reference to relative likelihood. In one example, the payers used to train the predictive model 1210c may be weighted based on likelihood of a given subscriber identifier corresponding to each payer. For example, weightings may be based in accordance with insurance industry statistical information regarding market share of subscribers. In another example, the weightings may be based on the statistical distribution in the training data where the training data is expected to be reasonably representative of the population as a whole.

Aspects of the present disclosure may be implemented by software logic, including machine readable instructions or commands for execution via processing circuitry. The software logic may also be referred to, in some examples, as machine readable code, software code, or programming instructions. The software logic, in certain embodiments, may be coded in runtime-executable commands and/or compiled as a machine-executable program or file. The software logic may be programmed in and/or compiled into a variety of coding languages or formats.

Aspects of the present disclosure may be implemented by hardware logic (where hardware logic naturally also includes any necessary signal wiring, memory elements and such), with such hardware logic able to operate without active software involvement beyond initial system configuration and any subsequent system reconfigurations (e.g., for different object schema dimensions). The hardware logic may be synthesized on a reprogrammable computing chip such as a field programmable gate array (FPGA) or other reconfigurable logic device. In addition, the hardware logic may be hard coded onto a custom microchip, such as an application-specific integrated circuit (ASIC). In other embodiments, software, stored as instructions to a non-transitory computer-readable medium such as a memory device, on-chip integrated memory unit, or other non-transitory computer-readable storage, may be used to perform at least portions of the herein described functionality.

Various aspects of the embodiments disclosed herein are performed on one or more computing devices, such as a laptop computer, tablet computer, mobile phone or other handheld computing device, or one or more servers. Such computing devices include processing circuitry embodied in one or more processors or logic chips, such as a central processing unit (CPU), graphics processing unit (GPU), field programmable gate array (FPGA), application-specific integrated circuit (ASIC), or programmable logic device (PLD). Further, the processing circuitry may be implemented as multiple processors cooperatively working in concert (e.g., in parallel) to perform the instructions of the inventive processes described above.

The process data and instructions used to perform various methods and algorithms derived herein may be stored in non-transitory (i.e., non-volatile) computer-readable medium or memory. The claimed advancements are not limited by the form of the computer-readable media on which the instructions of the inventive processes are stored. For example, the instructions may be stored on CDs, DVDs, in FLASH memory, RAM, ROM, PROM, EPROM, EEPROM, hard disk or any other information processing device with which the computing device communicates, such as a server or computer. The processing circuitry and stored instructions may enable the computing device to perform, in some examples, the process 100a of FIG. 1A, the process 100b of FIG. 1B, the process 100c of FIG. 1C, the process 100d of FIG. 1E, the processes 135a, 135b of FIG. 1F, the processes 155a, 155b of FIG. 1G, the method 300 of FIG. 3A, the process 350 of FIG. 3B, the method 400 of FIG. 4A and FIG. 4B, the process 500 of FIG. 5, and/or the process 1100 of FIG. 11C.

These computer program instructions can direct a computing device or other programmable data processing apparatus to function in a particular manner, such that the instructions stored in the computer-readable medium produce an article of manufacture including instruction means which implement the function/operation specified in the illustrated process flows.

Embodiments of the present description rely on network communications. As can be appreciated, the network can be a public network, such as the Internet, or a private network such as a local area network (LAN) or wide area network (WAN) network, or any combination thereof and can also include PSTN or ISDN sub-networks. The network can also be wired, such as an Ethernet network, and/or can be wireless such as a cellular network including EDGE, 3G, 4G, and 5G wireless cellular systems. The wireless network can also include Wi-Fi®, Bluetooth®, Zigbee®, or another wireless form of communication. The network, in some examples, may support communications between the predictive analytics platform 102 and the data universe 104, the predictive analytics platform 102 and the claims and billing platform 150, the claims and billing platform 150 and the claims and billing portal 110, and/or the predictive analytics platform 102 and the claims and billing portal 110 as discussed in relation to FIGS. 1A-1G, communications between the predictive analytics platform 102 and the claims and billing platform 150 as discussed in relation to FIG. 1D, and/or communications between the predictive analytics platform 102 and the clients 204, payers 206, and/or the service providers 208 as discussed in relation to FIG. 2.

The computing device, in some embodiments, further includes a display controller for interfacing with a display, such as a built-in display or LCD monitor. A general purpose I/O interface of the computing device may interface with a keyboard, a hand-manipulated movement tracked I/O device (e.g., mouse, virtual reality glove, trackball, joystick, etc.), and/or touch screen panel or touch pad on or separate from the display. The display controller and display may enable presentation of the user interfaces illustrated, in some examples, in FIG. 6A, FIG. 6B, FIG. 6C, FIG. 7, FIG. 8A, FIG. 8B, FIG. 9, FIG. 10, and/or FIG. 11B.

Moreover, the present disclosure is not limited to the specific circuit elements described herein, nor is the present disclosure limited to the specific sizing and classification of these elements. For example, the skilled artisan will appreciate that the circuitry described herein may be adapted based on changes in battery sizing and chemistry or based on the requirements of the intended back-up load to be powered.

The functions and features described herein may also be executed by various distributed components of a system. For example, one or more processors may execute these system functions, where the processors are distributed across multiple components communicating in a network. The distributed components may include one or more client and server machines, which may share processing, in addition to various human interface and communication devices (e.g., display monitors, smart phones, tablets, personal digital assistants (PDAs)). The network may be a private network, such as a LAN or WAN, or may be a public network, such as the Internet. Input to the system, in some examples, may be received via direct user input and/or received remotely either in real-time or as a batch process.

Although provided for context, in other implementations, methods and logic flows described herein may be performed on modules or hardware not identical to those described. Accordingly, other implementations are within the scope that may be claimed.

In some implementations, a cloud computing environment, such as Google Cloud Platform™ or Amazon™ Web Services (AWS™), may be used perform at least portions of methods or algorithms detailed above. The processes associated with the methods described herein can be executed on a computation processor of a data center. The data center, for example, can also include an application processor that can be used as the interface with the systems described herein to receive data and output corresponding information. The cloud computing environment may also include one or more databases or other data storage, such as cloud storage and a query database. In some implementations, the cloud storage database, such as the Google™ Cloud Storage or Amazon™ Elastic File System (EFS™), may store processed and unprocessed data supplied by systems described herein. For example, the contents of portions of the data universe 104 of FIGS. 1A-1G, portions of the data repository 210 of FIG. 2, plan data 354, patient data 356, and/or claims data 358 of FIG. 3B, and/or the procedure codes 504, the service request data 506, and/or the claims data 508 of FIG. 5 may be maintained in a database structure.

The systems described herein may communicate with the cloud computing environment through a secure gateway. In some implementations, the secure gateway includes a data querying interface, such as the Google BigQuery™ platform or Amazon RDS™. The data querying interface, for example, may support access to the predictive analytics platform 102 and/or the claims and billing platform 150 by the claims and billing portal 110, to the predictive analytics platform 102 by the claim sand billing platform, and/or to the data universe 104 by the predictive analytics platform 102 of FIGS. 1A-1G. Further, the data querying interface may support access by the predictive analytics platform 102 to data sources maintained by one or more of the clients 204, payers 206, and/or service providers 208 of FIG. 2.

While certain embodiments have been described, these embodiments have been presented by way of example only, and are not intended to limit the scope of the present disclosures. Indeed, the novel methods, apparatuses and systems described herein can be embodied in a variety of other forms; furthermore, various omissions, substitutions and changes in the form of the methods, apparatuses and systems described herein can be made without departing from the spirit of the present disclosures. The accompanying claims and their equivalents are intended to cover such forms or modifications as would fall within the scope and spirit of the present disclosures.

What is claimed is:

1. A computer-implemented method for predicting health insurer identity using machine learning models, the method comprising:

accessing, from a networked storage region including non-transitory computer readable media, electronic records comprising a set of known subscriber identifiers and an unranked list of corresponding confirmed health insurer identifiers;

generating a first training set by combining the set of known subscriber identifiers and the corresponding confirmed health insurer identifiers obtained from the electronic records;

training a first supervised machine learning model in a first training stage with the first training set to recognize patterns in subscriber identifiers as correlated with respective health insurers, wherein the first supervised machine learning model comprises a first decision tree model;

generating a second training set based on a portion of the subscriber identifiers having an alpha-numeric coding that corresponds to a particular geographical region;

training the first supervised machine learning model in a second training stage with the second training set to fine-tune the recognition of patterns in the subscriber identifiers based on geographical region;

generating a third training set by modifying the set of known subscriber identifiers to balance a number of records corresponding to the unranked list of confirmed health insurer identifiers;

training a second supervised machine learning model in a third training stage with the third training set to recognize patterns in subscriber identifiers as correlated with respective health insurers by providing the third training set to a second machine learning model training engine, wherein the second supervised machine learning model comprises a second decision tree model;

combining the first supervised machine learning model with the second supervised machine learning model to generate a predictive model for identifying a ranked list of health insurers associated with a particular subscriber identifier; and outputting, to a calling software system or to an end user interface and using the particular subscriber identifier and an associated geographical region as inputs to the generated predictive model, a ranked list of likely health insurers in association with the particular subscriber identifier, the ranked list being generated using a confidence level for each of the likely health insurers based on probabilities generated by the predictive model, wherein the end user interface is configured to display the ranked list of the likely health insurers in association with the particular subscriber identifier.

2. The method of claim 1, wherein the first supervised machine learning model is weighted based on insurance industry market share data.

3. The method of claim 1, wherein the second supervised machine learning model is weighted based on statistical distribution within the second training set.

4. The method of claim 1, comprising:

collecting new truth data including updated subscriber identifiers, corresponding confirmed health insurer identifiers corresponding to the updated subscriber identifiers, and demographic information;

providing the new truth data to a predictive model training engine; and updating the first and second machine learning models based on the new truth data.

5. The method of claim 4, wherein collecting the new truth data comprises collecting both positive truth data, wherein the subscriber identifiers correspond to confirmed health insurer identifiers, and negative truth data, wherein the subscriber identifiers fail to correspond with one or more likely health insurers, thereby improving an accuracy of the predictive model and reducing a likelihood of incorrect matches in subsequent predictions.

6. The method of claim 4, comprising updating the predictive model on an ongoing basis to maintain near real-time accuracy.

7. The method of claim 4, comprising updating the predictive model on a periodic basis to incorporate aggregated truth data sets from repeated executions of a subscriber identification process.

8. The method of claim 4, wherein the demographic information comprises one or more of subscriber age, a subscriber employer, or a subscriber employment status.

9. The method of claim 8, wherein the subscriber employer comprises at least one of local government, federal government, military, or a private employer.

10. The method of claim 8, wherein the particular geographical region corresponds to location information for a subscriber employer.

11. The method of claim 1, wherein subscriber identifiers and health insurers lack a unique one-to-one correspondence.

12. The method of claim 1, wherein each subscriber identifier and each health insurer identifier comprises a code.

13. The method of claim 12, wherein the patterns in subscriber identifiers comprise a pattern associated with elements of the code.

14. The method of claim 1, wherein an algorithm of at least one of the first or second decision tree models comprises a random forest model algorithm.

15. The method of claim 1, comprising generating a correlation map between subscriber identifiers and health insurers.

16. The method of claim 15, comprising automatically updating the correlation map when subscriber identifier formats change and/or health insurers are added or dropped.

17. The method of claim 1, comprising predicting the likely health insurers subject to a cap.

18. The method of claim 17, wherein the cap is three health insurers.

19. The method of claim 17, wherein the cap is one of ten health insurers, five health insurers, or two health insurers.

20. The method of claim 17, wherein the cap corresponds at least in part to a threshold confidence level applied to the confidence level.

21. The method of claim 1, wherein the particular geographical region corresponds to a subscriber address or a portion of a subscriber address.

22. The method of claim 1, wherein the end user interface comprises a representation of a telemedicine registration portal including a subscriber field and a drop-down list of possible health insurers, wherein drop-down list of possible health insurers comprises the ranked list of health insurers and the subscriber field comprises the particular subscriber identifier.

23. The method of claim 1, comprising:

generating a correlation map between subscriber identifiers and health insurers; and automatically updating the correlation map when subscriber identifier formats change and/or health insurers are added or removed.

24. The method of claim 23 wherein automatically updating the correlation map comprises:

accessing, from the storage region, a second set of known subscriber identifiers and a second unranked list of corresponding confirmed health insurer identifiers;

analyzing subscriber identifier formats of the second set of known subscriber identifiers;

analyzing the second unranked list of corresponding confirmed health insurer identifiers;

based on the analysis, collecting information comprising subscriber identifier format changes and comprising additions and removals of health insurers; and determining an update to the correlation map based on the collected information.

* * * * *